US012649932B2

(12) United States Patent
Brudno et al.

(10) Patent No.: US 12,649,932 B2
(45) Date of Patent: Jun. 9, 2026

(54) ENHANCED VIRAL TRANSDUCTION OF MAMMALIAN CELLS USING MATERIAL SCAFFOLDS

(71) Applicants: North Carolina State University, Raleigh, NC (US); The University of North Carolina at Chapel Hill, Chapel Hill, NC (US)

(72) Inventors: Yevgeny Brudno, Cary, NC (US); Pritha Agarwalla, Raleigh, NC (US); Gianpietro Dotti, Chapel Hill, NC (US)

(73) Assignees: North Carolina State University, Raleigh, NC (US); The University of North Carolina at Chapel Hill, Chapel Hill, NC (US)

( * ) Notice: Subject to any disclaimer, the term of this patent is extended or adjusted under 35 U.S.C. 154(b) by 781 days.

(21) Appl. No.: 17/917,770

(22) PCT Filed: Apr. 12, 2021

(86) PCT No.: PCT/US2021/026805
§ 371 (c)(1),
(2) Date: Oct. 7, 2022

(87) PCT Pub. No.: WO2021/207724
PCT Pub. Date: Oct. 14, 2021

(65) Prior Publication Data
US 2023/0136350 A1     May 4, 2023

Related U.S. Application Data

(60) Provisional application No. 63/008,069, filed on Apr. 10, 2020.

(51) Int. Cl.
| | |
|---|---|
| *C12N 15/87* | (2006.01) |
| *A61K 40/11* | (2025.01) |
| *A61K 40/31* | (2025.01) |
| *A61K 40/42* | (2025.01) |
| *C07K 14/705* | (2006.01) |
| *C07K 14/725* | (2006.01) |
| *C12N 5/00* | (2006.01) |
| *C12N 5/0783* | (2010.01) |

(52) U.S. Cl.
CPC .............. *C12N 15/87* (2013.01); *A61K 40/11* (2025.01); *A61K 40/31* (2025.01); *A61K 40/4211* (2025.01); *C07K 14/7051* (2013.01); *C12N 5/0068* (2013.01); *C12N 5/0636* (2013.01); *A61K 2239/31* (2023.05); *A61K 2239/38* (2023.05); *A61K 2239/48* (2023.05); *C12N 2510/00* (2013.01); *C12N 2533/74* (2013.01); *C12N 2740/16043* (2013.01)

(58) Field of Classification Search
CPC ....... C12N 15/87; C12N 5/0068; C12N 15/86
See application file for complete search history.

(56) References Cited

U.S. PATENT DOCUMENTS

| | | | |
|---|---|---|---|
| 3,610,795 A | 10/1971 | Antoine | |
| 6,261,834 B1 | 7/2001 | Srivastava | |
| 10,702,551 B2 | 7/2020 | Stephan | |
| 10,806,756 B2 | 10/2020 | Stephan | |
| 11,890,303 B2 | 2/2024 | Stephan | |
| 2019/0343879 A1 | 11/2019 | Roy et al. | |
| 2020/0085971 A1 | 3/2020 | Kevlahan et al. | |
| 2022/0339195 A1 | 10/2022 | Kealey | |
| 2022/0354972 A1 | 11/2022 | Brudno et al. | |
| 2024/0033293 A1 | 2/2024 | Stephan | |
| 2024/0122984 A1 | 4/2024 | Stephan | |
| 2024/0409672 A1 | 12/2024 | Brudno et al. | |

FOREIGN PATENT DOCUMENTS

| | | | | |
|---|---|---|---|---|
| JP | 2009-519042 A | 5/2009 | | |
| WO | WO 2007/070660 | 6/2007 | | |
| WO | WO-2017068419 A2 * | 4/2017 | ......... | C07K 14/7051 |
| WO | WO 2018/075940 | 4/2018 | | |
| WO | WO-2018183927 A1 | 10/2018 | | |
| WO | WO-2019014684 A1 | 1/2019 | | |
| WO | 2020014270 A1 | 1/2020 | | |
| WO | WO-2024081898 A1 | 4/2024 | | |

OTHER PUBLICATIONS

Jang et al. Plasmid Delivery in Vivo from Porous Tissue-Engineering Scaffolds: Transgene Expression and Cellular Transfection. Molecular Therapy 2005, 12;3:475-483. (Year: 2005).*
International Search Report and Written Opinion issued in PCT/US2021/026805, dated Sep. 28, 2021, 13 pages.
Brunger, J. M., et al., "Scaffold-mediated lentiviral transduction for functional tissue engineering of cartilage," PNAS, vol. 111, No. 9, 2014, pp. E798-E806.
Acsadi et al., Human dystrophin expression in mdx mice after intramuscular injection of DNA constructs. Nature. Aug. 29, 1991;352(6338):815-8.
Agarwal et al., In vivo generated human CAR T cells eradicate tumor cells. Oncoimmunology. Oct. 10, 2019;8(12):e1671761. 8 pages.
Agarwalla et al., Scaffold-Mediated Static Transduction of T Cells for CAR-T Cell Therapy. Adv Healthc Mater. Jul. 2020;9(14):e2000275. 6 pages.
Andersen et al., 3D Cell Culture in Alginate Hydrogels. Microarrays (Basel). Mar. 24, 2015;4(2):133-61.
Andreadis et al., Kinetics of retrovirus mediated gene transfer: the importance of intracellular half-life of retroviruses. J Theor Biol. Sep. 7, 1996;182(1):1-20.
Bach. National Coverage Analysis of CAR-T Therapies—Policy, Evidence, and Payment. N Engl J Med. Oct. 11, 2018;379(15):1396-1398.

(Continued)

*Primary Examiner* — Christopher M Babic
*Assistant Examiner* — Jennifer S Spence
(74) *Attorney, Agent, or Firm* — Casimir Jones, S.C.; Peter J. Schlueter

(57) ABSTRACT

Disclosed are compositions and methods for a low cost, tunable, macroporous, alginate scaffold that transduces T cells with vectors under static condition.

22 Claims, 28 Drawing Sheets

(56) References Cited

OTHER PUBLICATIONS

Figure 3A:
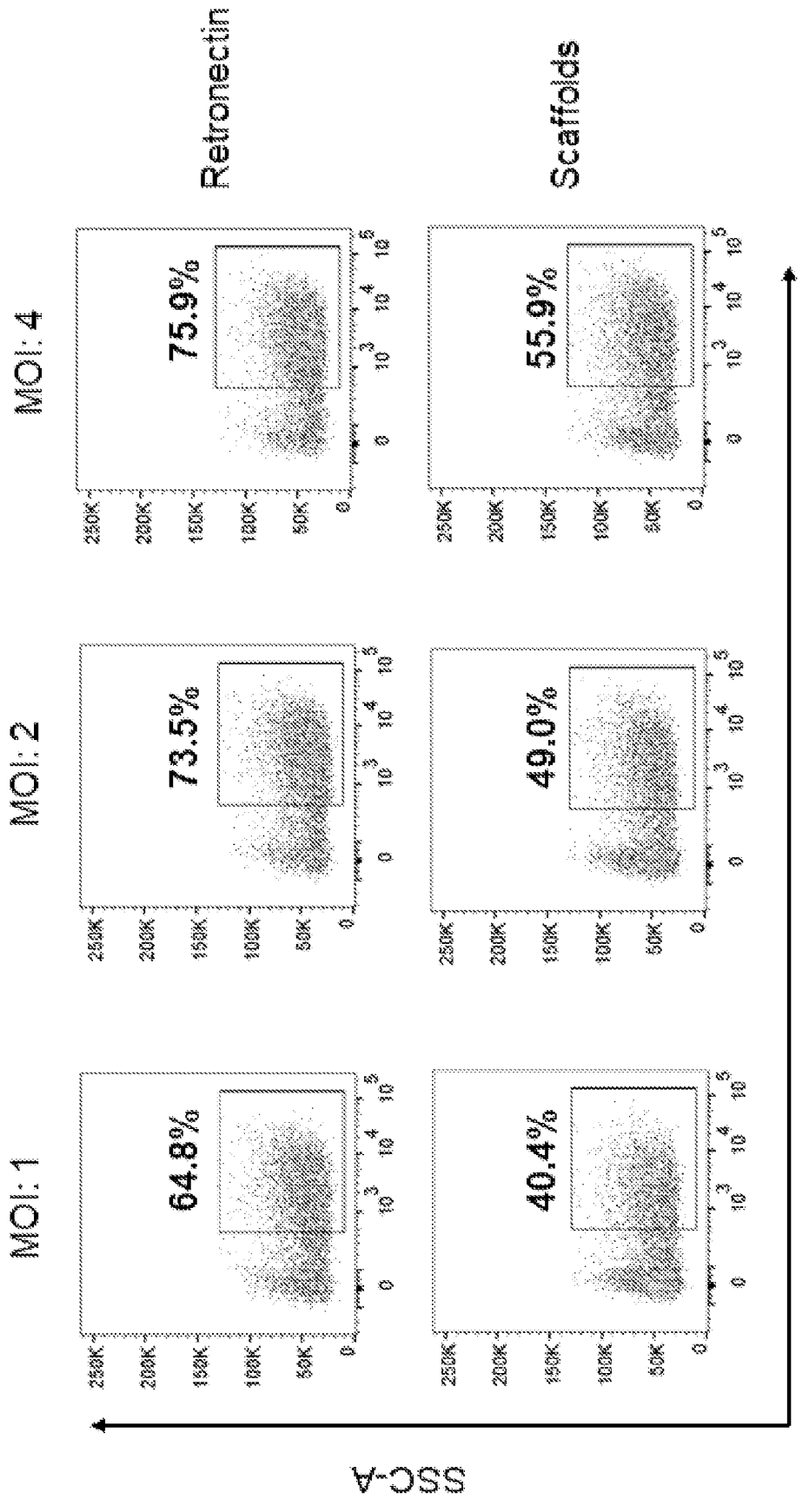

Bagshawe et al., A cytotoxic agent can be generated selectively at cancer sites. Br J Cancer. Dec. 1988;58(6):700-3.

Bagshawe. The First Bagshawe lecture. Towards generating cytotoxic agents at cancer sites. Br J Cancer. Sep. 1989;60(3):275-81.

Baldino et al., Interpenetration of Natural Polymer Aerogels by Supercritical Drying. Polymers (Basel). Mar. 24, 2016;8(4):106. 12 pages.

Banerji et al., A lymphocyte-specific cellular enhancer is located downstream of the joining region in immunoglobulin heavy chain genes. Cell. Jul. 1983;33(3):729-40.

Battelli et al., T lymphocyte killing by a xanthine-oxidase-containing immunotoxin. Cancer Immunol Immunother. 1992;35(6):421-5.

Berkner et al., Abundant expression of polyomavirus middle T antigen and dihydrofolate reductase in an adenovirus recombinant. J Virol. Apr. 1987;61(4):1213-20.

Boehler et al., A PLG/HAp composite scaffold for lentivirus delivery. Biomaterials. Jul. 2013;34(21):5431-8.

Bout et al., Lung gene therapy: in vivo adenovirus-mediated gene transfer to rhesus monkey airway epithelium. Hum Gene Ther. Jan. 1994;5(1):3-10.

Brown et al., Molecular and cellular mechanisms of receptor-mediated endocytosis. DNA Cell Biol. Jul.-Aug. 1991;10(6):399-409.

Brown et al., Penetration of host cell membranes by adenovirus 2. J Virol. Aug. 1973;12(2):386-96.

Brudno et al., In vivo targeting through click chemistry. ChemMedChem. Apr. 2015;10(4):617-20.

Caffrey. With approval of CAR T-cell therapy comes the next challenge: payer coverage. Am. J. Manag. Care 2018, 24, SP35-SP36.

Caillaud et al., Adenoviral vector as a gene delivery system into cultured rat neuronal and glial cells. Eur J Neurosci. Oct. 1, 1993;5(10):1287-91.

Chardonnet et al., Early events in the interaction of adenoviruses with HeLa cells. I. Penetration of type 5 and intracellular release of the DNA genome. Virology. Mar. 1970;40(3):462-77.

Cheung et al., Scaffolds that mimic antigen-presenting cells enable ex vivo expansion of primary T cells. Nat Biotechnol. Feb. 2018;36(2):160-169.

Chuck et al., Membrane adsorption characteristics determine the kinetics of flow-through transductions. Biotechnol Bioeng. Aug. 5, 1996;51(3):260-70.

Coon et al., Nitinol thin films functionalized with CAR-T cells for the treatment of solid tumours. Nat Biomed Eng. Feb. 2020;4(2):195-206.

Cotter et al., Molecular genetic analysis of herpesviruses and their potential use as vectors for gene therapy applications. Curr Opin Mol Ther. Oct. 1999;1(5):633-44.

Davidson et al., Overproduction of polyomavirus middle T antigen in mammalian cells through the use of an adenovirus vector. J Virol. Apr. 1987;61(4):1226-39.

Depil et al., 'Off-the-shelf' allogeneic CAR T cells: development and challenges. Nat Rev Drug Discov. Mar. 2020;19(3):185-199.

Diaconu et al., Inducible Caspase-9 Selectively Modulates the Toxicities of CD19-Specific Chimeric Antigen Receptor-Modified T Cells. Mol Ther. Mar. 1, 2017;25(3):580-592.

Enblad et al., A Phase I/IIa Trial Using CD19-Targeted Third-Generation CAR T Cells for Lymphoma and Leukemia. Clin Cancer Res. Dec. 15, 2018;24(24):6185-6194.

Extended European Search Report for 21785543.6. Mailed Jul. 1, 2024, 23 pages.

Fesnak et al., Engineered T cells: the promise and challenges of cancer immunotherapy. Nat Rev Cancer. Aug. 23, 2016;16(9):566-81.

Fiers et al., Complete nucleotide sequence of SV40 DNA. Nature, 1978, 273, 113-120.

Garcia et al., Modulation of cell proliferation and differentiation through substrate-dependent changes in fibronectin conformation. Mol Biol Cell. Mar. 1999;10(3):785-98.

Gattinoni et al., Paths to stemness: building the ultimate antitumour T cell. Nat Rev Cancer. Oct. 2012;12(10):671-84.

Ghassemi et al., Reducing Ex Vivo Culture Improves the Antileukemic Activity of Chimeric Antigen Receptor (CAR) T Cells. Cancer Immunol Res. Sep. 2018;6(9):1100-1109.

Gomez-Foix et al., Adenovirus-mediated transfer of the muscle glycogen phosphorylase gene into hepatocytes confers altered regulation of glycogen metabolism. J Biol Chem. Dec. 15, 1992;267(35):25129-34.

Greenaway et al., Human cytomegalovirus DNA: BamHI, EcoRI and PstI restriction endonuclease cleavage maps. Gene. Jun. 1982;18(3):355-60.

Grupp et al., Chimeric antigen receptor-modified T cells for acute lymphoid leukemia. N Engl J Med. Apr. 18, 2013;368(16):1509-1518.

Guzman et al., Efficient gene transfer into myocardium by direct injection of adenovirus vectors. Circ Res. Dec. 1993;73(6):1202-7.

Haj-Ahmad et al., Development of a helper-independent human adenovirus vector and its use in the transfer of the herpes simplex virus thymidine kinase gene. J Virol. Jan. 1986;57(1):267-74.

Hanenberg et al., Colocalization of retrovirus and target cells on specific fibronectin fragments increases genetic transduction of mammalian cells. Nat Med. Aug. 1996;2(8):876-82.

Havenga et al., Retroviral stem cell gene therapy. Stem Cells. 1997;15(3):162-79.

Hernandez. Analysis determines true cost for CAR T-cell therapy. Healio-In the Journals Plus. Accessed Oct. 24, 2024. 7 pages.

Hollyman et al., Manufacturing validation of biologically functional T cells targeted to CD19 antigen for autologous adoptive cell therapy. J Immunother. Feb.-Mar. 2009;32(2):169-80.

Hori et al., Modular injectable matrices based on alginate solution/microsphere mixtures that gel in situ and co-deliver immunomodulatory factors. Acta Biomater. May 2009;5(4):969-82.

Hughes et al., Monoclonal antibody targeting of liposomes to mouse lung in vivo. Cancer Res. Nov. 15, 1989;49(22):6214-20.

Hwang et al., Fabrication of three-dimensional porous cell-laden hydrogel for tissue engineering. Biofabrication. Sep. 2010;2(3):035003. 21 pages.

Jackson et al., Driving CAR T-cells forward. Nat Rev Clin Oncol. Jun. 2016;13(6):370-83.

Jena et al., Chimeric antigen receptor (CAR)-specific monoclonal antibody to detect CD19-specific T cells in clinical trials. PLoS One. 2013;8(3):e57838. 12 pages.

June et al., Adoptive cellular therapy: a race to the finish line. Sci Transl Med. Mar. 25, 2015;7(280):280ps7.

Kirshenbaum et al., Highly efficient gene transfer into adult ventricular myocytes by recombinant adenovirus. J Clin Invest. Jul. 1993;92(1):381-7.

Korin et al., Progression to the G1b phase of the cell cycle is required for completion of human immunodeficiency virus type 1 reverse transcription in T cells. J Virol. Apr. 1998;72(4):3161-8.

La Salle et al., An adenovirus vector for gene transfer into neurons and glia in the brain. Science. Feb. 12, 1993;259(5097):988-90.

Laimins et al., Osmotic control of kdp operon expression in *Escherichia coli*. Proc. Natl. Acad. Sci. 1981, 78, 1, 464-468.

Lamers et al., Protocol for gene transduction and expansion of human T lymphocytes for clinical immunogene therapy of cancer. Cancer Gene Ther. Jul. 2002;9(7):613-23.

Lamers et al., Retronectin-assisted retroviral transduction of primary human T lymphocytes under good manufacturing practice conditions: tissue culture bag critically determines cell yield. Cytotherapy. 2008;10(4):406-16.

Lan et al., Myoblast proliferation and differentiation on fibronectin-coated self assembled monolayers presenting different surface chemistries. Biomaterials. Aug. 2005;26(22):4523-31.

Lee et al., Alginate: properties and biomedical applications. Prog Polym Sci. Jan. 2012;37(1):106-126.

(56) References Cited

OTHER PUBLICATIONS

Lee et al., T cells expressing CD19 chimeric antigen receptors for acute lymphoblastic leukaemia in children and young adults: a phase 1 dose-escalation trial. Lancet. Feb. 7, 2015;385(9967):517-528.

Leyfman. Chimeric antigen receptors: unleashing a new age of anti-cancer therapy. Cancer Cell Int. Nov. 14, 2018:18:182. 6 pages.

Lichtman et al., Chimeric antigen receptor T-cells for B-cell malignancies. Transl Res. 2017;187: 59-82.

Lin et al., Polybrene inhibits human mesenchymal stem cell proliferation during lentiviral transduction. PLoS One. 2011;6(8):e23891. 9 pages.

Litzinger et al., Biodistribution and immunotargetability of ganglioside-stabilized dioleoylphosphatidylethanolamine liposomes. Biochim Biophys Acta. Feb. 17, 1992;1104(1):179-87.

Lusky et al., Bovine papilloma virus contains an activator of gene expression at the distal end of the early transcription unit. Mol Cell Biol. Jun. 1983;3(6):1108-22.

Ma et al., Anti-prostate specific membrane antigen designer T cells for prostate cancer therapy. Prostate. Sep. 15, 2004;61(1):12-25.

Maiti et al., Sleeping beauty system to redirect T-cell specificity for human applications. J Immunother. Feb. 2013;36(2):112-23.

Martinsen et al., Alginate as immobilization material: I. Correlation between chemical and physical properties of alginate gel beads. Biotechnol Bioeng. Jan. 5, 1989;33(1):79-89.

Massie et al., Construction of a helper-free recombinant adenovirus that expresses polyomavirus large T antigen. Mol Cell Biol. Aug. 1986;6(8):2872-83.

Maude et al., Chimeric antigen receptor T cells for sustained remissions in leukemia. N Engl J Med. Oct. 16, 2014;371(16):1507-17.

Maude et al., Tisagenlecleucel in Children and Young Adults with B-Cell Lymphoblastic Leukemia. N Engl J Med. Feb. 1, 2018;378(5):439-448.

Maus et al., Making Better Chimeric Antigen Receptors for Adoptive T-cell Therapy. Clin Cancer Res. Apr. 15, 2016;22(8):1875-84.

Mock et al., Automated manufacturing of chimeric antigen receptor T cells for adoptive immunotherapy using CliniMACS prodigy. Cytotherapy. Aug. 2016;18(8):1002-1011.

Morgan et al., Genetic Modification of T Cells. Biomedicines. Apr. 20, 2016;4(2):9.

Morsy et al., Efficient adenoviral-mediated ornithine transcarbamylase expression in deficient mouse and human hepatocytes. J Clin Invest. Sep. 1993;92(3):1580-6.

Moullier et al., Correction of lysosomal storage in the liver and spleen of MPS VII mice by implantation of genetically modified skin fibroblasts. Nat Genet. Jun. 1993;4(2):154-9.

Mulligan et al., Expression of a bacterial gene in mammalian cells. Science. Sep. 19, 1980;209(4463):1422-7.

Nakazawa et al., Evaluation of long-term transgene expression in piggyBac-modified human T lymphocytes. J Immunother. Jan. 2013;36(1):3-10.

Nakazawa et al., Optimization of the PiggyBac transposon system for the sustained genetic modification of human T lymphocytes. J Immunother. Oct. 2009;32(8):826-36.

Neelapu et al., Kte-C19 (anti-CD19 CAR T Cells) Induces Complete Remissions in Patients with Refractory Diffuse Large B-Cell Lymphoma (DLBCL): Results from the Pivotal Phase 2 Zuma-1. Blood. 2016. vol. 128, Iss 22, p. LAB-6.

Newick et al., CAR T Cell Therapy for Solid Tumors. Annu Rev Med. Jan. 14, 2017:68:139-152.

Osborne et al., Transcription control region within the protein-coding portion of adenovirus E1A genes. Mol Cell Biol. Jul. 1984;4(7):1293-305.

Park et al., Long-Term Follow-up of CD19 CAR Therapy in Acute Lymphoblastic Leukemia. N Engl J Med. Feb. 1, 2018;378(5):449-459.

Parker et al., Expansion and characterization of T cells transduced with a chimeric receptor against ovarian cancer. Hum Gene Ther. Nov. 20, 2000;11(17):2377-87.

Patel et al., T-cell therapies for HIV: Preclinical successes and current clinical strategies. Cytotherapy. Aug. 2016;18(8):931-942.

Pettitt et al., CAR-T Cells: A Systematic Review and Mixed Methods Analysis of the Clinical Trial Landscape. Mol Ther. Feb. 7, 2018;26(2):342-353.

Pietersz et al., Antibody conjugates for the treatment of cancer. Immunol Rev. Oct. 1992:129:57-80.

Pollok et al., High-efficiency gene transfer into normal and adenosine deaminase-deficient T lymphocytes is mediated by transduction on recombinant fibronectin fragments. J Virol. Jun. 1998;72(6):4882-92.

Prasad. Immunotherapy: Tisagenlecleucel—the first approved CAR-T-cell therapy: implications for payers and policy makers. Nat Rev Clin Oncol. Jan. 2018;15(1):11-12.

Qin. Gel swelling properties of alginate fibers. J Appl Polym Sci. 2004;91: 1641-1645.

Quintas-Cardama et al., Multifactorial optimization of gammaretroviral gene transfer into human T lymphocytes for clinical application. Hum Gene Ther. Dec. 2007;18(12):1253-60.

Ragot et al., Replication-defective recombinant adenovirus expressing the Epstein-Barr virus (EBV) envelope glycoprotein gp340/220 induces protective immunity against EBV-induced lymphomas in the cottontop tamarin. J Gen Virol. Mar. 1993:74 ( Pt 3):501-7.

Ramanayake et al., Low-cost generation of Good Manufacturing Practice-grade CD19-specific chimeric antigen receptor-expressing T cells using piggyBac gene transfer and patient-derived materials. Cytotherapy. Sep. 2015;17(9):1251-67.

Ramos et al., CD19-CAR trials. Cancer J. Mar.-Apr. 2014;20(2):112-8.

Ramos et al., Clinical and immunological responses after CD30-specific chimeric antigen receptor-redirected lymphocytes. J Clin Invest. Sep. 1, 2017;127(9):3462-3471.

Ramos et al., Clinical responses with T lymphocytes targeting malignancy-associated K light chains. J Clin Invest. Jul. 1, 2016;126(7):2588-96.

Rich et al., Development and analysis of recombinant adenoviruses for gene therapy of cystic fibrosis. Hum Gene Ther. Aug. 1993;4(4):461-76.

Robinet et al., A closed culture system for the ex vivo transduction and expansion of human T lymphocytes. J Hematother. Jun. 1998;7(3):205-15.

Roessler et al., Adenoviral-mediated gene transfer to rabbit synovium in vivo. J Clin Invest. Aug. 1993;92(2):1085-92.

Roffler et al., Anti-neoplastic glucuronide prodrug treatment of human tumor cells targeted with a monoclonal antibody-enzyme conjugate. Biochem Pharmacol. Oct. 24, 1991;42(10):2062-5.

Rosenberg et al., Adoptive cell transfer as personalized immunotherapy for human cancer. Science. Apr. 3, 2015;348(6230):62-8.

Rosenblum et al., Progress and challenges towards targeted delivery of cancer therapeutics. Nat Commun. Apr. 12, 2018;9(1):1410.

Salter et al., Chimeric antigen receptor-modified T cells: CD19 and the road beyond. Blood. Jun. 14, 2018;131(24):2621-2629.

Savina et al., A simple method for the production of large volume 3D macroporous hydrogels for advanced biotechnological, medical and environmental applications. Sci Rep. Feb. 17, 2016:6:21154. 9 pages.

Savoldo et al., CD28 costimulation improves expansion and persistence of chimeric antigen receptor-modified T cells in lymphoma patients. J Clin Invest. May 2011;121(5):1822-6.

Savoldo et al., Chimeric antigen receptors (CARs) from bench-to-bedside. Immunol Lett. Sep.-Oct 2013;155(1-2):40-2.

Senter et al., Generation of 5-fluorouracil from 5-fluorocytosine by monoclonal antibody-cytosine deaminase conjugates. Bioconjug Chem. Nov.-Dec. 1991;2(6):447-51.

Senter et al., Generation of cytotoxic agents by targeted enzymes. Bioconjug Chem. Jan.-Feb. 1993;4(1):3-9.

Seo et al., Adoptive T-cell therapy for pediatric cytomegalovirus-associated retinitis. Blood Adv. Jun. 11, 2019;3(11):1774-1777.

Seth et al., Evidence that the penton base of adenovirus is involved in potentiation of toxicity of Pseudomonas exotoxin conjugated to epidermal growth factor. Mol Cell Biol. Aug. 1984;4(8):1528-33.

(56) References Cited

OTHER PUBLICATIONS

Seth et al., Role of a low-pH environment in adenovirus enhancement of the toxicity of a Pseudomonas exotoxin-epidermal growth factor conjugate. J Virol. Sep. 1984;51(3):650-5.

Shah et al., Mechanisms of resistance to CAR T cell therapy. Nat Rev Clin Oncol. Jun. 2019;16(6):372-385.

Shapiro et al., Novel alginate sponges for cell culture and transplantation. Biomaterials. Apr. 1997;18(8):583-90.

Sharma et al., Axicabtagene ciloleucel for the treatment of relapsed/refractory B-cell non-Hodgkin's lymphomas. Drugs Today (Barc). Mar. 2018;54(3):187-198.

Shin et al., Lentivirus delivery by adsorption to tissue engineering scaffolds. J Biomed Mater Res A. Jun. 15, 2010;93(4):1252-9.

Simmons et al., Retroviral Transduction of T Cells and T Cell Precursors. Methods Mol Biol. 2016:1323:99-108.

Smith et al., Biopolymers codelivering engineered T cells and STING agonists can eliminate heterogeneous tumors. J Clin Invest. Jun. 1, 2017;127(6):2176-2191.

Smith et al., In situ programming of leukaemia-specific T cells using synthetic DNA nanocarriers. Nat Nanotechnol. Aug. 2017;12(8):813-820.

Southern et al., Transformation of mammalian cells to antibiotic resistance with a bacterial gene under control of the SV40 early region promoter. J Mol Appl Genet. 1982;1(4):327-41.

Stephan et al., Biopolymer implants enhance the efficacy of adoptive T-cell therapy. Nat Biotechnol. Jan. 2015;33(1):97-101.

Stock et al., Influence of Retronectin-Mediated T-Cell Activation on Expansion and Phenotype of CD19-Specific Chimeric Antigen Receptor T Cells. Hum Gene Ther. Oct. 2018;29(10):1167-1182.

Sugden et al., A vector that replicates as a plasmid and can be efficiently selected in B-lymphoblasts transformed by Epstein-Barr virus. Mol Cell Biol. Feb. 1985;5(2):410-413.

Sun et al., Human artificial episomal chromosomes for cloning large DNA fragments in human cells. Nat Genet. Sep. 1994;8(1):33-41.

Svensson. Role of vesicles during adenovirus 2 internalization into Hela cells. J Virol. Aug. 1985;55(2):442-9.

Tang et al., The global landscape of cancer cell therapy. Nat Rev Drug Discov. Jul. 2018;17(7):465-466.

Tonks et al., Optimized retroviral transduction protocol which preserves the primitive subpopulation of human hematopoietic cells. Biotechnol Prog. May-Jun. 2005;21(3):953-8.

Turtle et al., CD19 Car-T cells of defined CD4+:CD8+ composition in adult B cell ALL patients. J Clin Invest. Jun. 1, 2016;126(6):2123-38.

Varga et al., Infectious entry pathway of adenovirus type 2. J Virol. Nov. 1991;65(11):6061-70.

Vera et al., T lymphocytes redirected against the kappa light chain of human immunoglobulin efficiently kill mature B lymphocyte-derived malignant cells. Blood. Dec. 1, 2006;108(12):3890-7.

Verhoeyen et al., Lentiviral vector gene transfer into human T cells. Methods Mol Biol. 2009:506:97-114.

Watanabe et al., Expanding the Therapeutic Window for CAR T Cell Therapy in Solid Tumors: The Knowns and Unknowns of CAR T Cell Biology. Front Immunol. Oct. 26, 2018:9:2486. 12 pages.

Wickham et al., Integrins $\alpha v \beta 3$ and $\alpha v \beta 5$ promote adenovirus internalization but not virus attachment. Cell, 1993; 73:309-319.

Wolff et al., Direct gene transfer into mouse muscle in vivo. Science. Mar. 23, 1990;247(4949 Pt 1):1465-8.

Xu et al., Closely related T-memory stem cells correlate with in vivo expansion of CAR.CD19-T cells and are preserved by IL-7 and IL-15. Blood. Jun. 12, 2014;123(24):3750-9.

Xu et al., Selection bias: maintaining less-differentiated T cells for adoptive immunotherapy. J Clin Invest. Jan. 2016;126(1):35-7.

Zabner et al., Adenovirus-mediated gene transfer transiently corrects the chloride transport defect in nasal epithelia of patients with cystic fibrosis. Cell. Oct. 22, 1993;75(2):207-16.

Zabner et al., Safety and efficacy of repetitive adenovirus-mediated transfer of CFTR cDNA to airway epithelia of primates and cotton rats. Nat Genet. Jan. 1994;6(1):75-83.

Zhang et al., Generation and identification of recombinant adenovirus by liposome-mediated transfection and PCR analysis. Biotechniques. Nov. 1993;15(5):868-72.

Zhao et al., Multiple injections of electroporated autologous T cells expressing a chimeric antigen receptor mediate regression of human disseminated tumor. Cancer Res. Nov. 15, 2010;70(22):9053-61.

Zhou et al., High-efficiency gene transfer into rhesus macaque primary T lymphocytes by combining 32 degrees C centrifugation and CH-296-coated plates: effect of gene transfer protocol on T cell homing receptor expression. Hum Gene Ther. Oct. 10, 2001;12(15):1843-55.

* cited by examiner

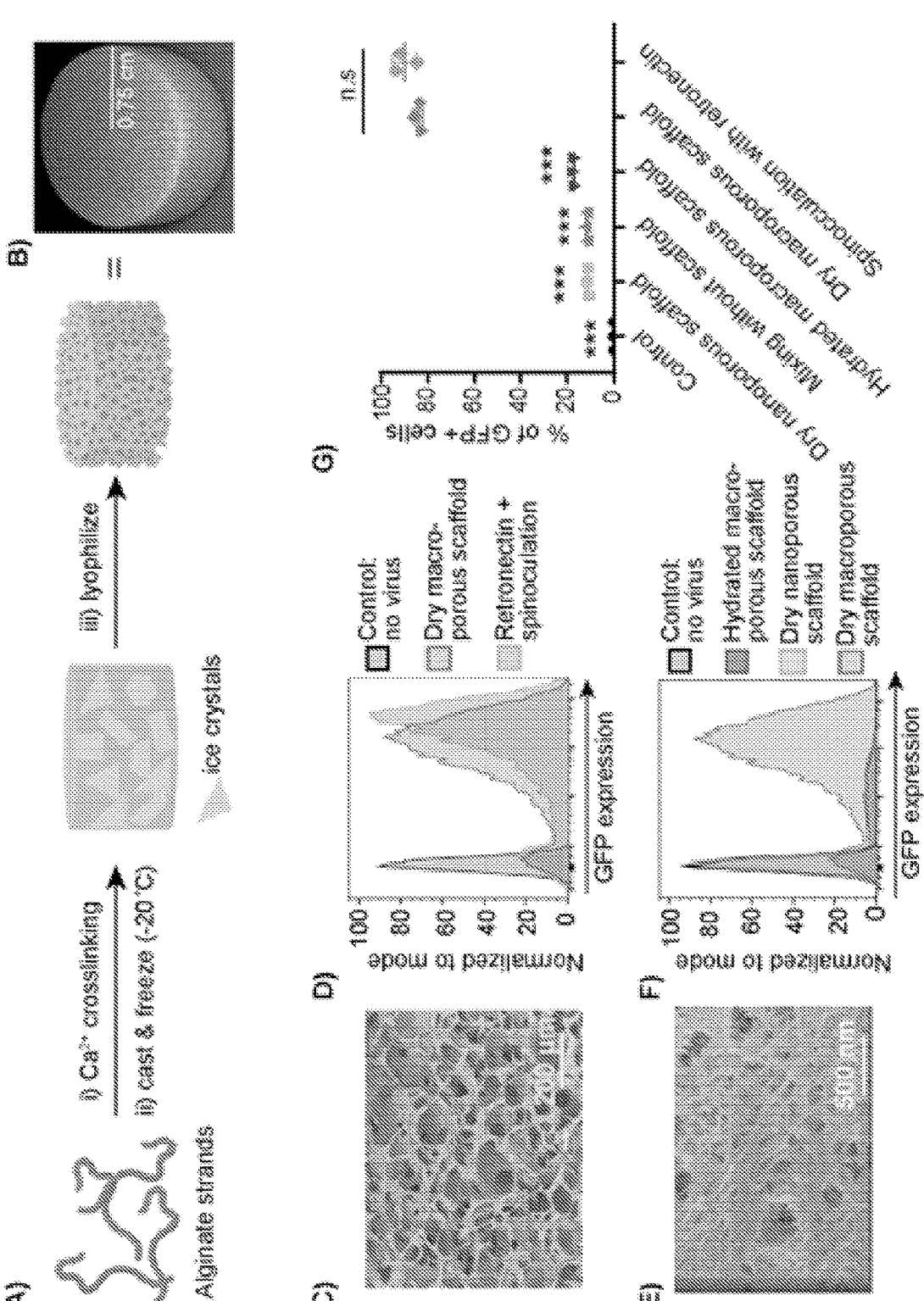
FIG. 1A, FIG. 1B, FIG. 1C, FIG. 1D, FIG. 1E, FIG. 1F, AND FIG. 1G

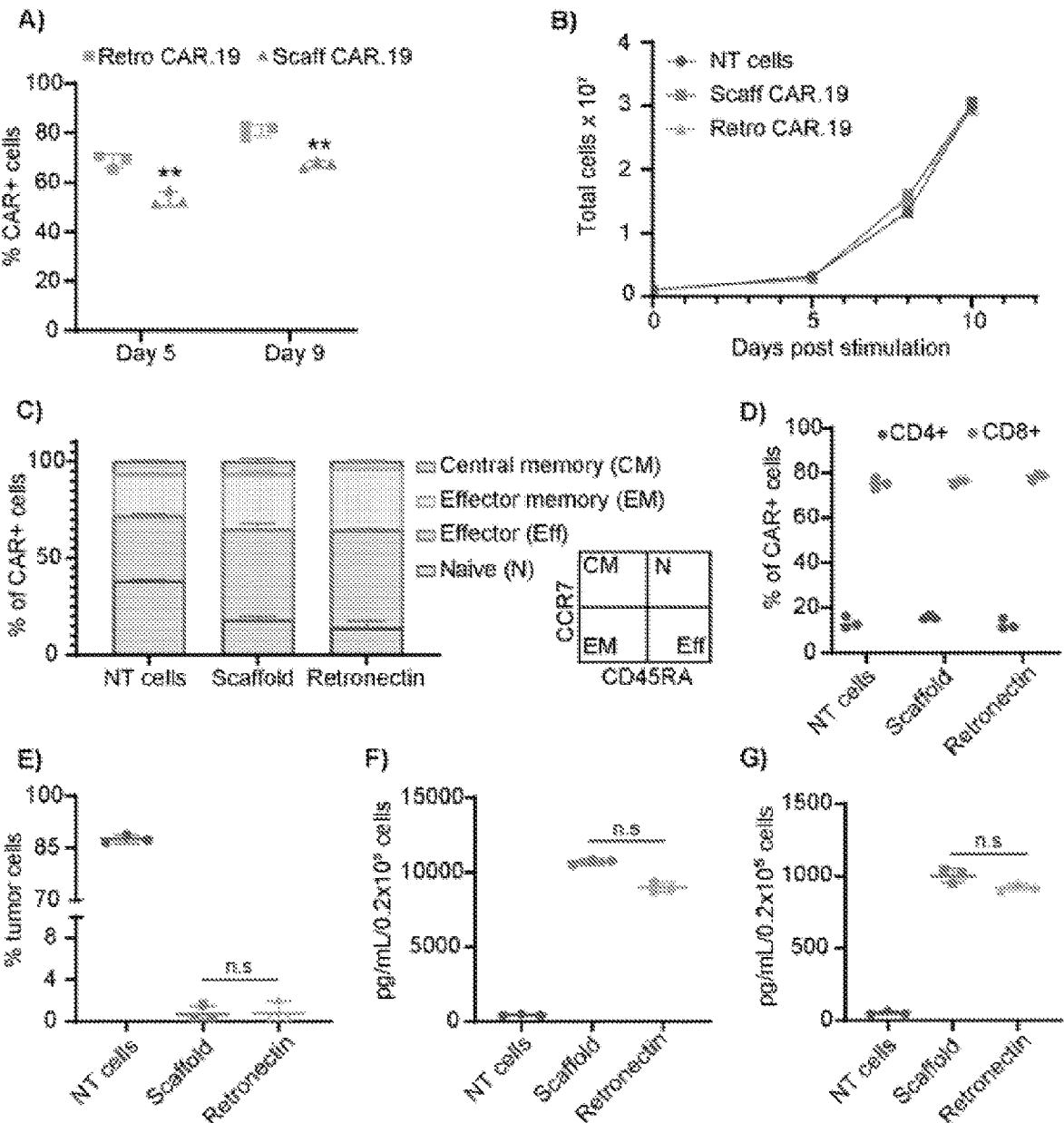
FIG. 2A, FIG. 2B, FIG. 2C, FIG. 2D, FIG. 2E, FIG. 2F, and FIG. 2G

FIG. 8A, FIG. 8B, FIG. 8C, FIG. 8D, and FIG. 8E

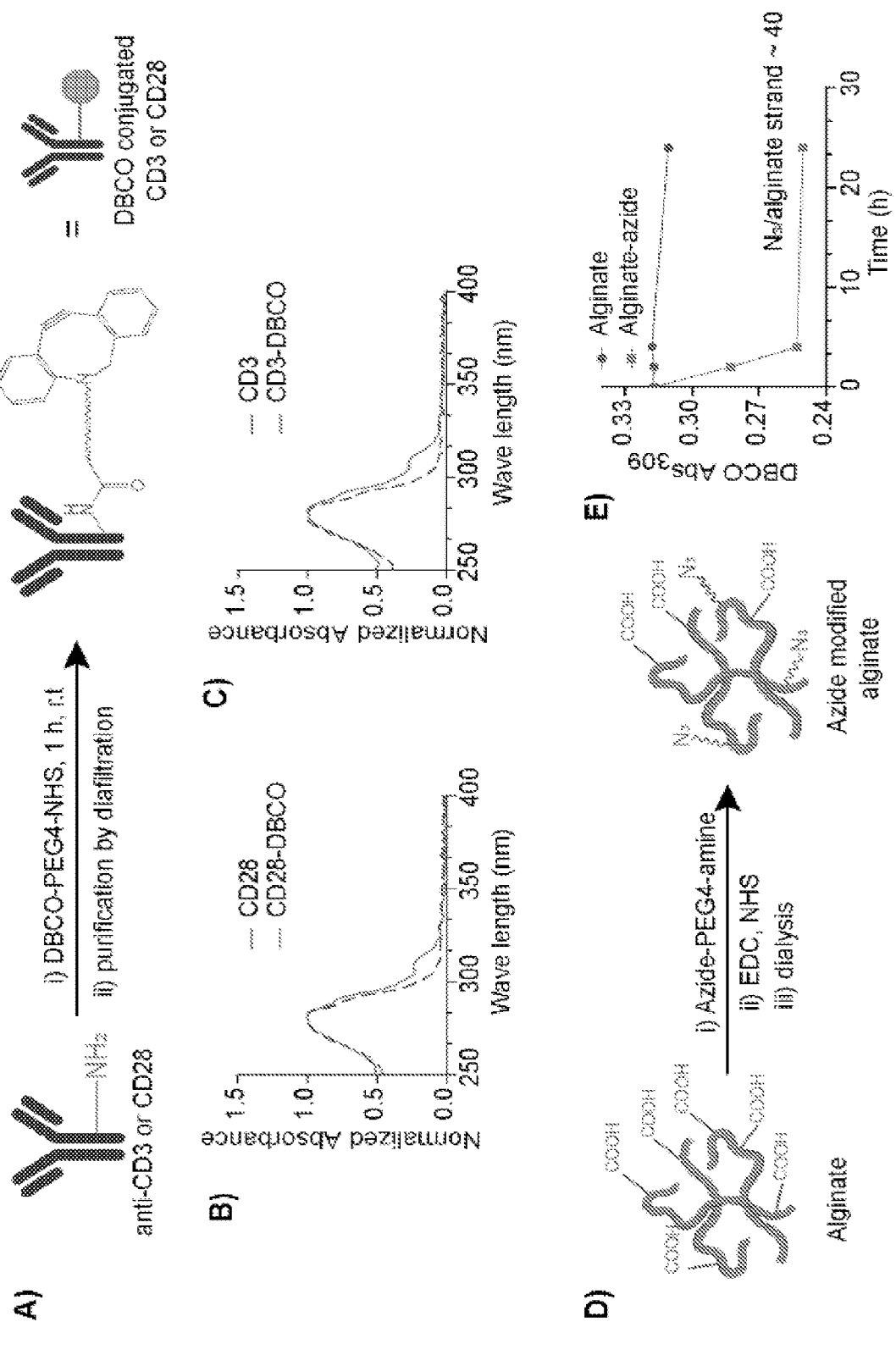
FIG. 10A, FIG. 10B, FIG. 10C, FIG. 10D, and FIG. 10E

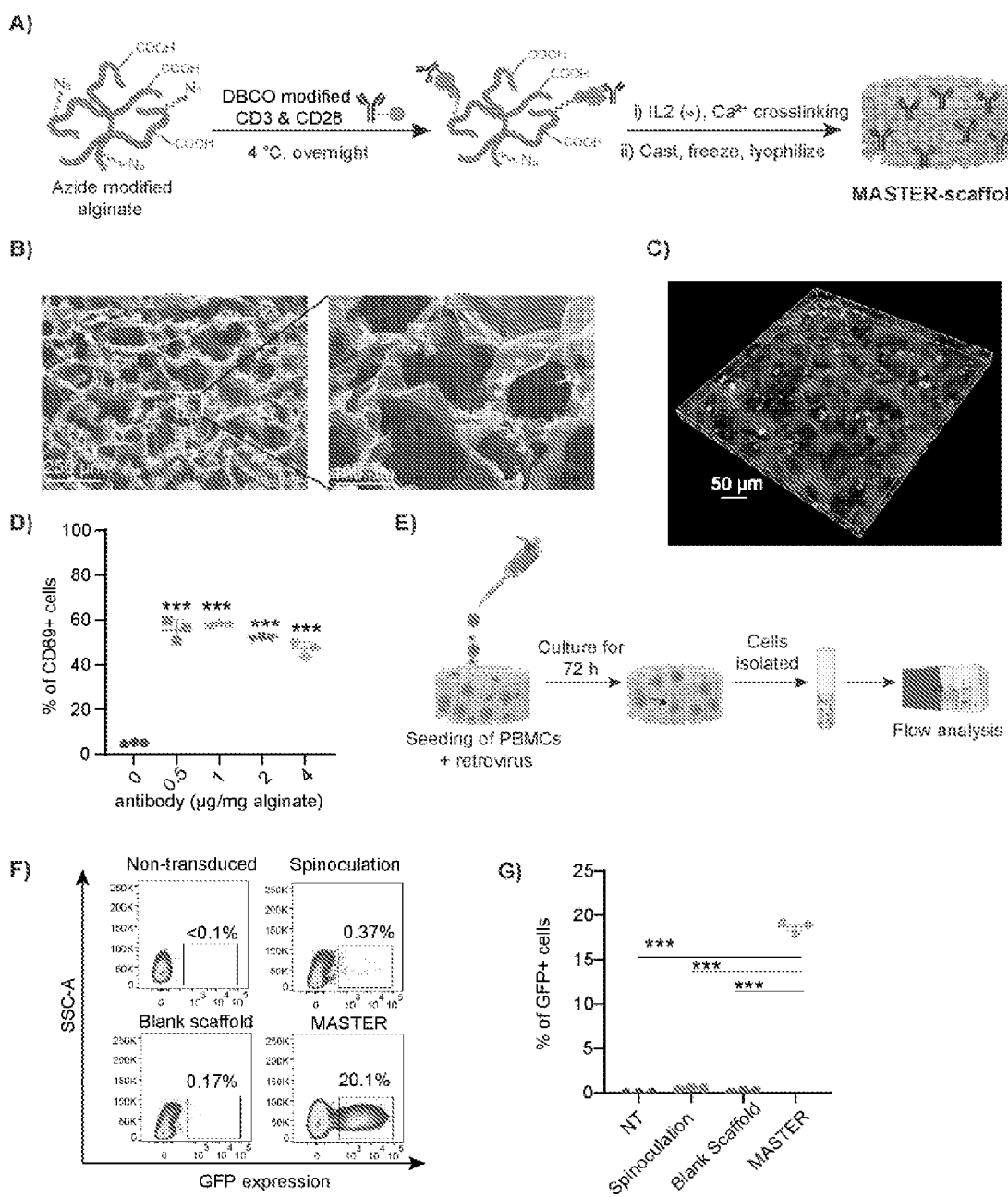
FIG. 11A, FIG, 11B, FIG. 11C, FIG. 11D, FIG. 11E, FIG. 11F, and FIG. 11G

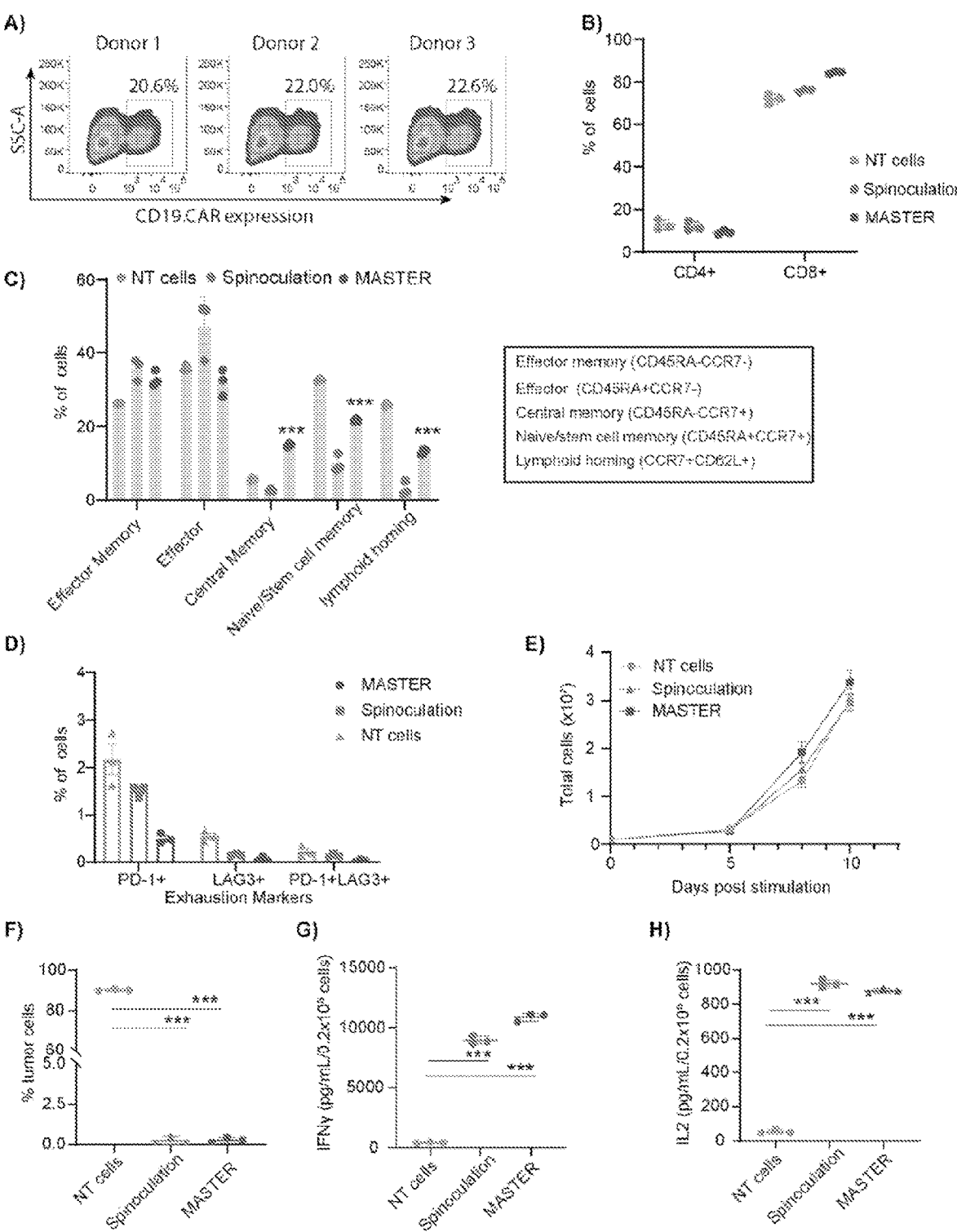
FIG. 13A, FIG, 13B, FIG. 13C, FIG. 13D, FIG. 13E, FIG. 13F, FIG. 13G, and FIG. 13H

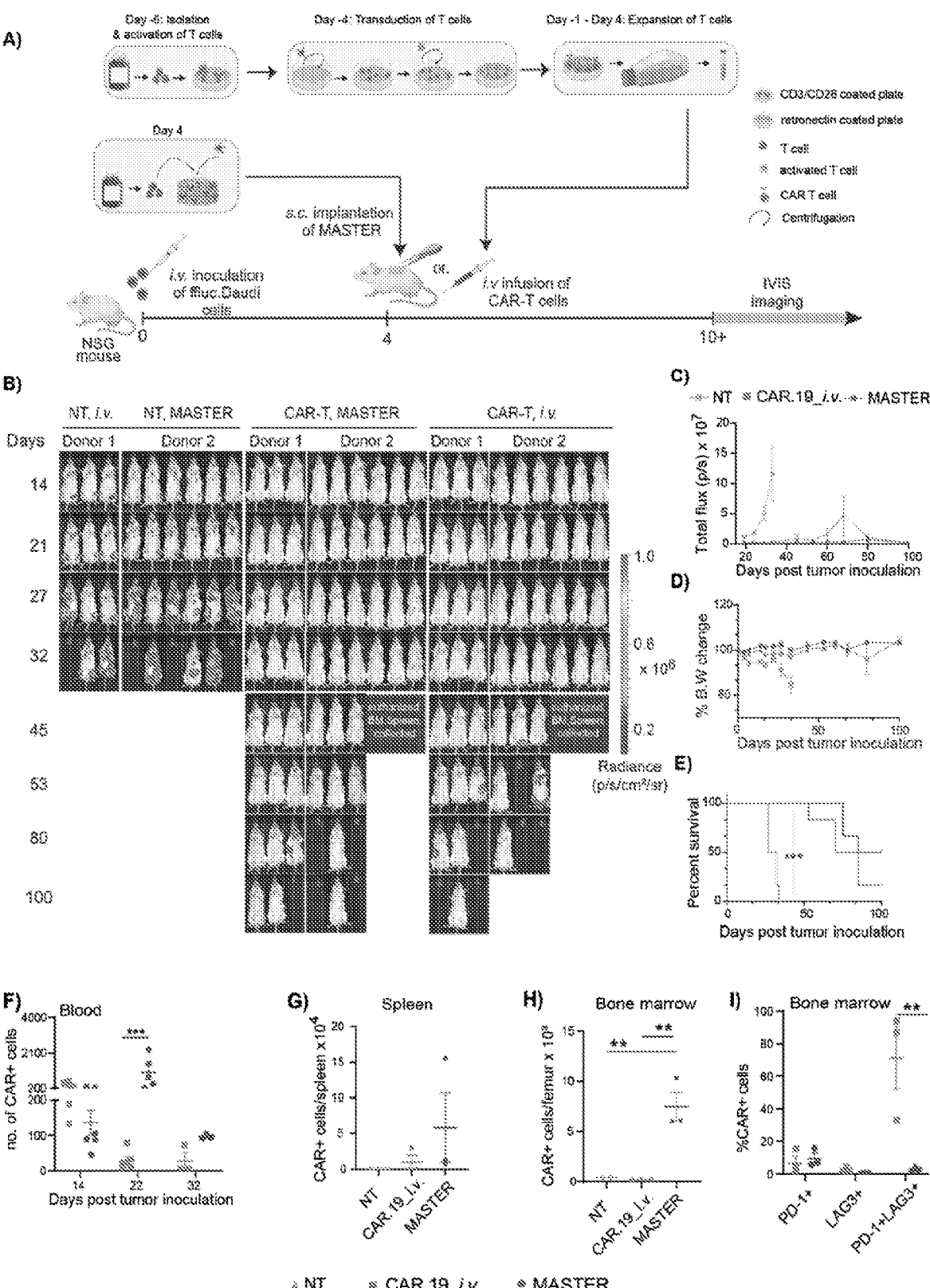
FIG. 18A, FIG, 18B, FIG. 18C, FIG. 18D, FIG. 18E, FIG. 18F, FIG. 18G, FIG. 18H, and FIG. 18I

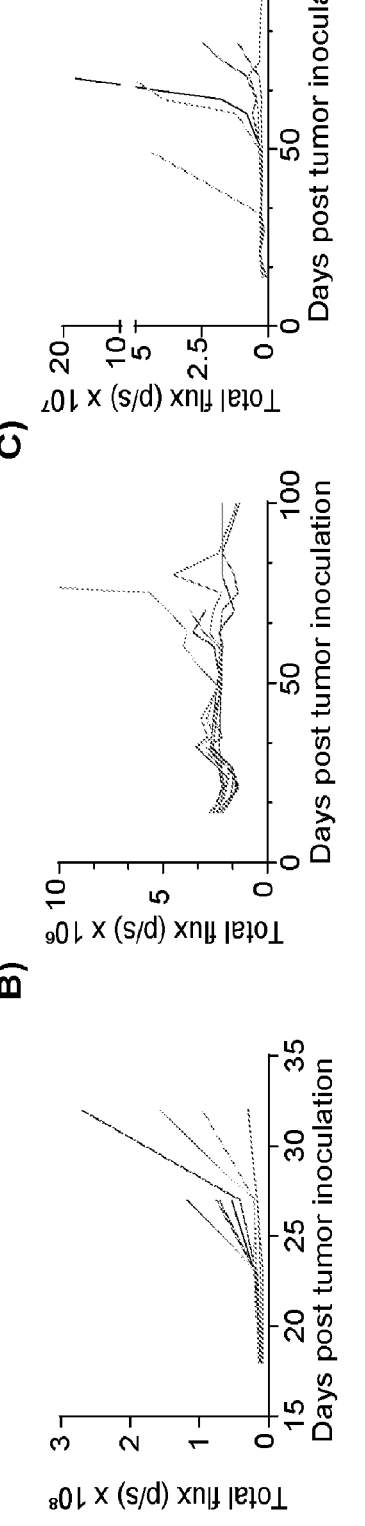
FIG. 19A, FIG. 19B, and FIG. 19C
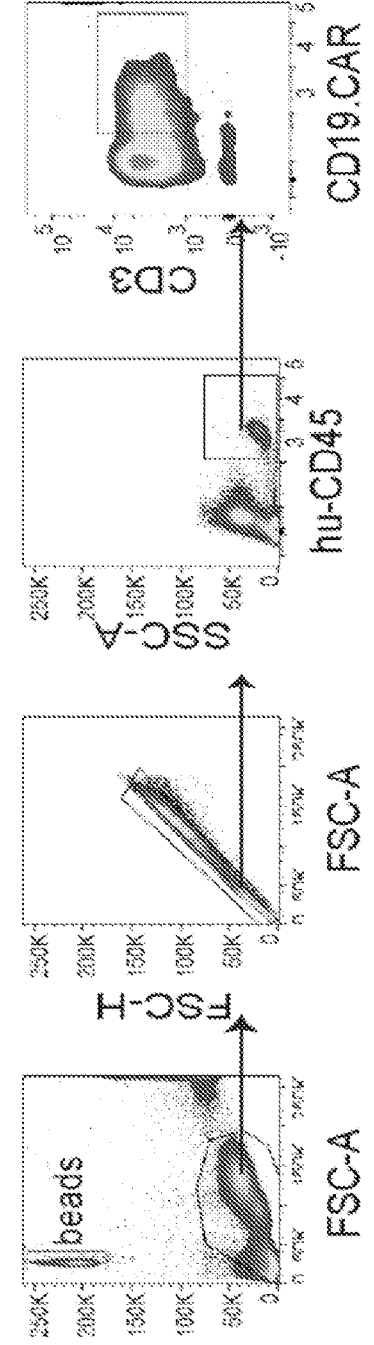
FIG. 20

FIG. 23A, FIG. 23B, FIG. 23C, FIG. 23D, FIG. 23E, FIG. 23F, and FIG. 23G

FIG. 24A, Fig. 24B, FIG. 24C, FIG. 24D, FIG. 24E, and FIG. 24F

| Sample | Untreated control | MASTER | MASTER + cells + virus |
|---|---|---|---|
| RBC (M/µL) | 9.89 ± 0.5 | 10.09 ± 0.2 | 9.86 ± 0.5 |
| WBC (K/µL) | 7.8 ± 1.6 | 6.5 ± 0.4 | 6.06 ± 1.07 |
| Neutrophil (/µL) | 333.67 ± 24.4 | 331.33 ± 19.5 | 315.67 ± 47.1 |
| Monocyte (/µL) | 352 ± 95.8 | 280 ± 56.8 | 219 ± 54.4 |
| Eosinophil (/µL) | 120 ± 57.4 | 131.3 ± 57.7 | 199.3 ± 88.7 |
| Basophil | 7.66 ± 6.8 | 10.33 ± 9.6 | 6 ± 5.5 |
| Lymphocyte (%) | 89.43 ± 1.6 | 88.4 ± 1.9 | 87.6 ± 1.6 |
| HCT (%) | 45.8 ± 1.4 | 47 ± 1.63 | 45.8 ± 0.7 |
| Absolute reticulocyte (K/µL) | 317.3 ± 46.54 | 360.6 ± 33.29 | 335 ± 44.23 |
| HGB (g/dL) | 14.2 ± 0.9 | 14.3 ± 0.3 | 14.03 ± 0.5 |
| MCV (fL) | 46.3 ± 1.15 | 47 ± 1 | 46.6 ± 1.5 |
| MCH (pg) | 14.4 ± 0.17 | 14.36 ± 0.05 | 14.23 ± 0.2 |
| MCHC (g/dL) | 30.96 ± 1.07 | 30.6 ± 0.34 | 30.6 ± 0.66 |
| Platelet Count (K/µL) | 966 ± 65.19 | 945 ± 39.71 | 967 ± 144.8 |
| Poikilocytosis | none seen | none seen | none seen |
| Polychromasia | slight | Moderate | Moderate |
| Heinz bodies | None seen | None seen | None seen |
| Metamyelocyte (%) | None seen | None seen | None seen |
| Myelocyte | None seen | None seen | None seen |
| Promyelocyte (%) | None seen | None seen | None seen |
| Unclassified (%) | None seen | None seen | None seen |

FIG. 26

A)

🔵 Hu-PBMCs ❋ GFP encoded retrovirus ➤ Human Fibroblast cells

B)

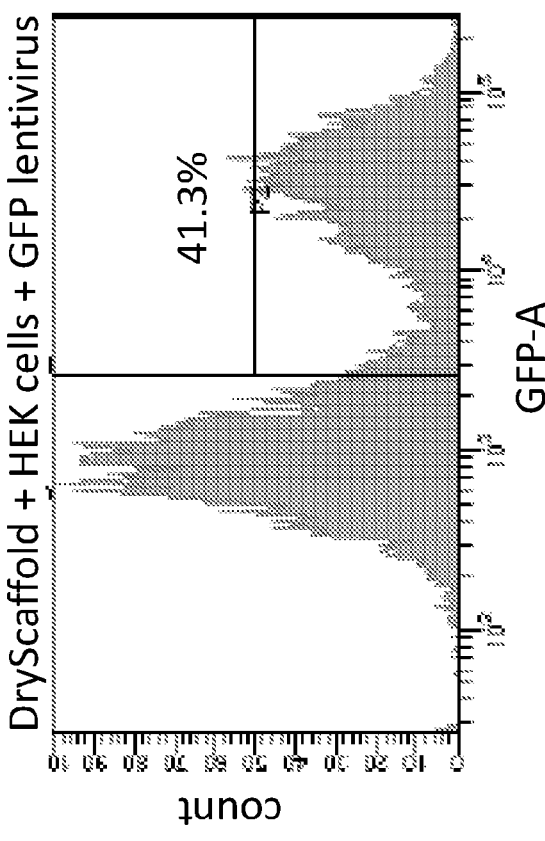
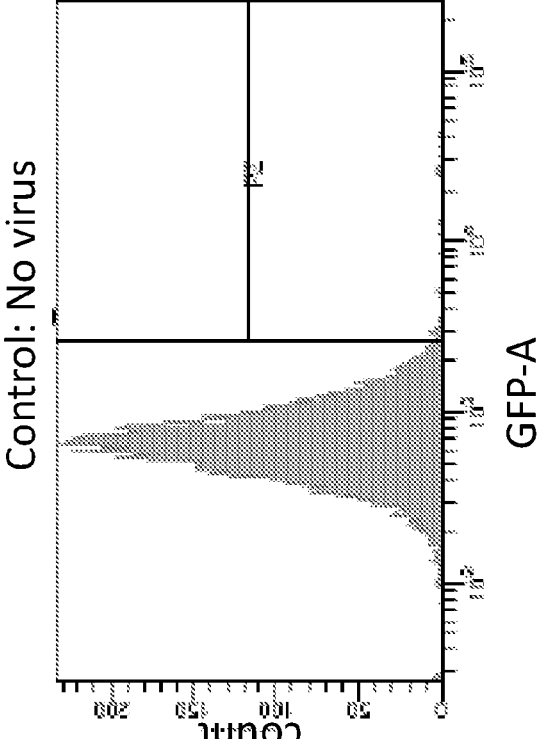
FIG. 28

ENHANCED VIRAL TRANSDUCTION OF MAMMALIAN CELLS USING MATERIAL SCAFFOLDS

CROSS REFERENCE TO RELATED APPLICATIONS

This is a national stage application filed under 35 U.S.C § 371 of PCT Application No. PCT/US2021/026805, filed Apr. 12, 2021, entitled "ENHANCED VIRAL TRANS-DUCTION OF MAMMALIAN CELLS USING MATE-RIAL SCAFFOLDS," which claims the benefit of U.S. Provisional Application No. 63/008,069, filed on Apr. 10, 2020, applications which are is incorporated herein by reference in their entirety.

ACKNOWLEDGMENT OF GOVERNMENT SUPPORT

This invention was made with government support under Grant No. TR002489 awarded by the National Institutes of Health. The government has certain rights in the invention.

I. BACKGROUND

1. Adoptive T cellular therapy harnesses and redirects patient's own immune system and has emerged as a promising personalized treatment modality to treat cancer and various other diseases. The most successful example has been the adoptive transfer of chimeric antigen receptor redirected T cells (CAR-T cells) targeting the CD19 expressed by B-cell-derived malignancies that received FDA approvals in 2017. With the compelling success of CD19-specific CAR-T cell therapies, efforts are now being directed towards broadening the application of CAR-T cells to other cancer types. One of the key steps involved in current CAR-T cell therapy is the genetic modification of T cells ex vivo, which endows T cells with stable expression of the CAR molecule that redirect T-cell specificity towards tumor antigens.

2. A number of different approaches are being explored to genetically engineer T cells ex vivo. Among them, lentiviral or retroviral vector (RV)-based gene transfer represents the most successful approach. When RV are used to generate CAR-T cells, T cells isolated from patients are first stimulated with agonistic anti-CD3 and anti-CD28 antibodies and then incubated with RV because quiescent T cells are refractory to RV-mediated insertion. Because of the short distance a RV particle can travel in solution by Brownian motion (less than 600 m within one half-life) activated T cells and RV must be brought into contact by centrifugation or spinoculation in the presence of transduction-promoting agents. Transduction-promoting agents like polybrene and protamine sulphate have been used with modest success, while recombinant fibronectin fragment CH296 (Retronec-tin) represents the most widely clinically used transduction-promoting reagent for RV. Retronectin binds RV through its heparin-binding domain and T cells via CS-1/RGD domains, bringing cells and RV together and facilitating gene transfer. Retronectin must be pre-coated onto a solid surface, such as a polystyrene plate, flask or bag for effective co-localization of RV and T cells. Even then, gene transfer and subsequent CAR expression remains suboptimal under passive/static conditions. To achieve high gene expression, RV are seeded on retronectin-coated surfaces and cells are centrifuged to concentrate them on the same surface. Such retronectin assisted spinoculation has scaling limitations and significant costs. Furthermore, retronectin is a recombinant protein, and it is inherently bioreactive which can influence cell differentiation and proliferation. Thus the development of more efficient culture systems enabling a single-step ex vivo processing of T cells under static conditions without retronectin or spinoculation would significantly reduce the cost of CAR-T cell manufacturing when RV or other viral vectors are used as gene delivery system.

II. SUMMARY

3. Disclosed are modified hydrogels or dry scaffolds and their uses in transducing cells to make, for example, chimeric antigen receptor cells and treating Cancer.

4. In one aspect, disclosed herein are biocompatible hydrogel matrixes and/or dry scaffolds (such as, for example, dry scaffolds or hydrogels comprising alginate) comprising one or more ligands or antibodies specific for a T cell receptor and/or NI cell receptor (including, but not limited to anti-CD3 antibody, CD1d, an Fc fragment of an immunoglobulin, or anti-Fc gamma receptor (FcγRIII) antibody). The disclosed hydrogel matrixes and/or dry scaffolds can be scaffolds used for transducing cells (such as, for example, immune cells including but not limited to T cells, natural killer (NK) cells, NK T cells, macrophage, tumor infiltrating lymphocytes (TILs), tumor infiltrating NK cells (TINKs), and/or a marrow infiltrating lymphocytes (MILs) as well as nonimmune cells such as, for example, mesenchymal stem cell (MSC), hematopoietic stem cell (HSC), dendritic cell, neural stem cell, induced pluripotent stem cell, or islet cells) and making chimeric antigen receptor (CAR) cells. In addition, the scaffolds can be used to transduce cancer cells or any other cell types for basic research purposes. Accordingly, in one aspect, the hydrogel matrixes and/or dry scaffolds can comprise a vector (such as, for example, a lentivirus, retrovirus, adenovirus, adeno-associated virus, virus-like particles, cell-mimicing particles, transposons, exosomes, nanoparticles, micelles or liposomes) encoding and/or encapsulating an exogenous gene, siRNA, tasiRNA, lncRNA, shRNA, mRNA, gRNA, miRNA, and/or DNA encoding said siRNA, tasiRNA, lncRNA, shRNA, mRNA, gRNA, miRNA (including, but not limited to engineered genes, siRNA, tasiRNA, lncRNA, shRNA, mRNA, gRNA, and/or miRNA, such as, for example, a chimeric antigen receptor (CAR) gene).

5. Also disclosed herein are hydrogel matrixes and/or dry scaffolds of any preceding aspect further comprising one or more antibodies, cytokines (such as, for example, IL-2, TNF-α, or IFN-γ), and/or co-stimulatory molecules which activate a T ell, natural killer (NK) cell, NK T cell, macrophage, tumor infiltrating lymphocyte (TIL), tumor infiltrating NK cell (TINK), or a marrow infiltrating lymphocyte (MIL). The hydr gel matrixes c and/or dry scaffolds an also comprises a ligand or antibody that induces signaling through a T cell, NK cell, or NK T cell co-stimulatory receptor including, but not limited to anti-CD28, B7-1, B7-2, anti-inducible costimulator (ICOS), ICOS ligand, anti-CD27, CD70, 4-1BBL, anti-41-BB, anti-CD40L, CD40, anti-DAP10, anti-CD30, CD30L, anti-TIM-1, anti-TIM-2, anti-TIM-3, anti-CD44, anti-NK1.1, lectin like transcript-1 (LLT-1), anti-CD137, CD48, MICA, anti-2B4, and anti-glucocorticoid-induced tumor necrosis factor receptor related protein (GITR).

6. In one aspect, disclosed herein are hydrogel matrixes and/or dry scaffolds of any preceding aspect, further comprising a chemotherapeutic agent.

7. Also disclosed herein are methods of treating, inhibiting, red icing, decreasing, ameliorating, and/or preventing a disease or condition (such as, for example, a cancer or metastasis or graft versus host disease (GVHD), myocardial infarction, ischemia, bone/cartilage damage, osteoarthritis, epilepsy, hemophilia, severe osteogenesis imperfecta, Wiskott-Aldrich syndrome, X-linked severe combined immune-deficiency, β-thalassemia, Adrenoleukodystrophy (ALD), Metachromatic leukodystrophy (MLD), cancer, or Parkinson's disease) in a subject comprising administering to the subject the hydrogel and/or dry scaffold of any preceding aspect. Thus, in one aspect, disclosed herein are methods of treating, reducing, inhibiting, ameliorating, decreasing, and/or preventing a cancer and/or metastasis in a subject comprising a) obtaining cell (such as, for example, an immune cell, including but not limited to a T cell, natural killer (NK) cell, NK T cell, macrophage, tumor infiltrating lymphocyte (TIL), tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or ha haplo-identical donor source) and a vector (such as, for example, a lentivirus, retrovirus, adenovirus, adeno-associated virus, virus-like particle, cell-mimicing particles, transposons exosomes, nanoparticles, micelles or liposomes) encoding an exogeneous gene (such as, for example, a chimeric antigen receptor), b) applying the cell and vector to a scaffold (such as, for example, a biocompatible hydrogel matrix and/or dry scaffold, including, but not limited to alginate); c) incubating the immune cells with the hydrogel and/or with the dry scaffolds for 1, 2, 3, 4, 5, 10, 15, 20, 25, 30, 35, 40, 45, 50, 55 minutes, 1, 2, 3, 4, 5, 6, 7, 8, 9, 0, 11, 12, 13, 14, 15, 16, 17, 18, 19, 20, 21, 22, 23, 24, 24, 25, 26, 27, 28, 29, 30, 31, 32, 33, 4, 35, 36, 37, 38, 39, 40, 41, 42, 43, 44, 45, 46, 47, 48, 54, 60, 66, 72, 84, 96 hours 5, 6, 7, 8, 9, 10, 11, 12, 13, or 14 days; and d) administering the hydrogel and/or dry scaffold with the cells to the subject with or without incubation in step c or administering the cells having been incubated with the hydrogel and/or dry scaffold to the subject. In some aspects, the scaffold further comprises a ligand or antibody for a T cell receptor, or NK cell receptor (including, but not limited to anti-CD3 antibody, CD1d, an Fc fragment of an immunoglobulin, or anti-Fc gamma receptor (FcγRIII) antibody). Accordingly, in one aspect, disclosed herein are methods of treating, inhibiting, reducing, decreasing, ameliorating, and/or preventing a cancer or metastasis in a subject of any preceding aspect, wherein the vector in the scaffold (such as a hydrogel matrix and/or a dry scaffold) transduces the cell and the transduced cell in the scaffold can be released into the subject at the site of the cancer following administration of the scaffold over a period of 1, 2, 3, 4, 5, 6, 7, 8, 9, 10, 11 12, 13, 14, 15, 16, 17, 18, 19, 20, 21, 22, 23, 24, 24, 25, 26, 27, 28, 29, 30, 31, 32, 33, 34, 35, 36, 37, 38, 39, 40, 41, 42, 43, 4, 45, 46, 47, 48, 54, 60, 66, 72, 84, 96 hours 5, 6, 7, 8, 9, 10, 11, 12, 13, 14, 15, 16, 17, 18, 19, 20, 21, 22, 23, 24, 24, 25, 26, 27, 28, 29, 30, 31, 32, 45, 58, 59, 60, 61, 62, 90 days, 3, 4, 5, 6, 7, 8, 9, 10, 11, 12, 13, 14, 15, 16, 17, 18, 19, 20, 21, 22, 23, 24, 36 months, 4, 5, 6, 7, 8, 9, 10 years. In one aspect, the cell is released from the hydrogel from about 1 week to about 12 weeks after administration of the hydrogel and/or dry scaffold.

8. In one aspect, disclosed herein are methods of treating, inhibiting, reducing, decreasing, ameliorating, and/or preventing a cancer or metastasis in a subject of any preceding aspect, wherein the scaffold further comprises an anti-cancer agent (such as, for example, an immune blockade inhibitor or chemotherapeutic agent).

9. Also disclosed herein are methods of transducing a cell (such as for example, an immune cell (such as, for example, a T cell, natural killer (NK) cell, NK T cell, tumor infiltrating lymphocyte (TIL), macrophage, tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source), a non-immune cell (such as, for example, a mesenchymal stem cell (MSC), hematopoietic stem cell (HSC), dendritic cell, neural stem cell, induced pluripotent stem cell, or islet cells), including immune and non-immune primary cells, as well as cell lines) as well as methods of making a chimeric antigen receptor immune cell, said methods comprising a) obtaining a cell (such as for example, an immune cell (such as, for example, a T cell, natural killer (NK) cell, NK T cell, tumor infiltrating lymphocyte (TIL), macrophage, tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source), a non-immune cell (such as, for example, a mesenchymal stem cell (MSC), hematopoietic stem cell (HSC), dendritic cell, neural stem cell, induced pluripotent stem cell, or islet cells), including immune and non-immune primary cells, as well as cell lines) and a vector encoding and/or encapsulating an exogenous gene, siRNA, tasiRNA, lncRNA, shRNA, mRNA, gRNA, miRNA, and/or DNA encoding said siRNA, tasiRNA, lncRNA, shRNA mRNA, gRNA, miRNA (including, but not limited to engineered genes, siRNA, tasiRNA, lncRNA, shRNA, mRNA, gRNA, and/or miRNA, such as, for example, a chimeric antigen receptor (CAR) gene) and b) applying the cell to a scaffold (such as, for example a biocompatible hydrogel matrix and/or dry scaffold such as, for example, a hydrogel or scaffold comprising alginate) and incubating the scaffold, cell, and the vector. In some aspects, the scaffold further comprises a ligand or antibody for a T cell receptor, or NK cell receptor (including, but not limited to anti-CD3 antibody, CD1d, an Fe fragment of an immunoglobulin, or anti-Fc gamma receptor (FcγRIII) antibody. Incubation of the scaffold, cell, and vector can occur for 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24, 24, 25, 26, 27, 28, 29, 30, 31, 32, 33, 34, 35, 36, 37, 38, 39, 40, 41, 42, 43, 44, 45, 46, 47, 48, 54, 60, 66, 72, 84, 96 hours 5, 6, 7, 8, 9, 10, 11, 12, 13, or 14 days or alternatively implanting the scaffold and the cells without incubation. 10. In one aspect, disclosed herein are methods of transducing a cell (such as for example, an immune cell (such as, for example, a T cell, natural killer (NK) cell, NK T cell, tumor infiltrating lymphocyte (TIL), macrophage, tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source), a non-immune cell (such as, for example, a mesenchymal stem cell (MSC), hematopoietic stem cell (HSC), dendritic cell, neural stem cell, induced pluripotent stem cell, or islet cells), primary cell, or cell line) of any preceding aspect as well as methods of making a chimeric antigen receptor immune cell of any preceding aspect, wherein the cell is a naïve cell, and wherein the scaffold further comprises a ligand or antibody that induces signaling through a T cell, NK cell, or NK T cell co-stimulatory receptor including, but not limited to anti-CD28, B7-1, B7-2, anti-inducible costimulator (ICOS), ICOS ligand, anti-CD27, CD70, 4-1BBL, anti-41-BB, anti-CD40L, CD40, anti-DAP10, anti-CD30, CD30L, anti-TIM-1, anti-TIM-2, anti-TIM-3, anti-D44, anti-NK1.1, lectin like transcript-1 (LLT-1), anti-CD137, CD48, MICA, anti-2B4, and anti-glucocorticoid-induced tumor necrosis factor receptor related protein (GITR).

11. Also disclosed herein are methods of transducing a cell (such as for example, an immune cell (such as, for example, a T cell, natural killer (NK) cell, N T cell, tumor infiltrating lymphocyte (TIL), macrophage, tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source), a non-immune cell (such as, for example, a mesenchymal stem cell (MSC), hematopoietic stem cell (HSC), dendritic cell, neural stem cell, induced pluripotent stem cell, or islet cells), including immune and non-immune primary cells, as well as cell lines) of any preceding aspect as well as methods of making a chimeric antigen receptor immune cell of any preceding aspect, wherein the scaffold further comprises one or more cytokines (such as, for example, IL-2, TNF-α, and/or IFN-γ).

III. BRIEF DESCRIPTION OF THE DRAWINGS

12. The accompanying drawings, which are incorporated in and constitute a part of this specification, illustrate several embodiments and together with the description illustrate the disclosed compositions and methods.

13. FIGS. 1A, 1B, 1C, 1D, 1E, 1F, and 1G show dry macroporous scaffolds mediate retroviral transduction of human activated T cells. FIG. 1A shows a schematic showing the preparation of macroporous alginate scaffolds. FIGS. 1B and 1C show SEM images of dry macroporous scaffolds. FIG. 1D shows GFP expression in activated T cells transduced with retrovirus seeded on dry macroporous scaffolds (red) and retronectin-coated plates with spinoculation (blue). Non-transduced control cells are represented in black. FIG. 1E shows SEM image of dry nanoporous scaffold. FIG. 1F shows GFP expression in T cells transduced with retrovirus seeded on dry macroporous scaffolds (red), hydrated macroporous scaffolds (purple), and dry nanoporous scaffolds (green). Control non-transduced cells are in black. FIG. 1G shows quantification of GFP⁺ cells (***p<0.0001 with respect to dry macroporous scaffolds, Student's t test)

14. FIGS. 2A, 2B, 2C, 2D, 2E, 2F, and 2G show scaffold-generated CD19.CAR-T cells show similar functional activity to retronectin/spinoculation-derived CAR-T cells in vitro. FIG. 2A shows CD19.CAR expression in T cells transduced on retronectin-coated plates or on macroporous scaffolds in comparison to non-transduced control T cells (NT cells). FIG. 2B shows ex vivo expansion of T cells transduced on retronectin-coated plates or on macroporous scaffolds or NT cells. FIGS. 2C and 2D show immunophenotypic composition of CAR-T cells obtained via scaffold-mediated or retronectin/spinoculation-mediated transduction and NT cells at day 12 of culture. Analysis was performed gating on CAR-expressing T cells except for NT cells. FIG. 2E shows the percentage of CD19⁺ Daudi cells remaining (tumor cells) when co-cultured with scaffold-generated, retronectin/spinoculation-generated CAR-T cells or control NT cells. Tumor cells and T cells were plated at 1:5 effector to target ratio. T cells and tumor cells were quantified by flow cytometry on day 5 of co-culture. P<0.0001 when scaffold CAR-T cells or retronectin/spinoculation CAR-T cells were compared with control NT cells; unpaired Student's t-test. FIGS. 2F and 2G show IFN-γ (2F) and IL-2 (2G) release into co-culture supernatant by scaffold-generated, retronectin/spinoculation-generated AR-T cells and control NT cells after 24 h of coculture with tumor cells as assessed by ELISA. P<0.0001 when scaffold CAR-T cells or retronectin/spinoculation CAR-T cells were compared with control NT cells; two-way ANOVA with Tukey correction. Data are represented as the mean±SD from three experiments.

15. FIG. 3A shows FACS analysis of T cells transduced with GFP encoding retroviral vectors at various MOIs (1, 2, 4) on Day 3 post transduction. T cells were transduced with GFP encoding retrovirus on retronectin coated plates or scaffold at various MOI and analyzed for GFP expression by flow cytometry.

Figure 3B:
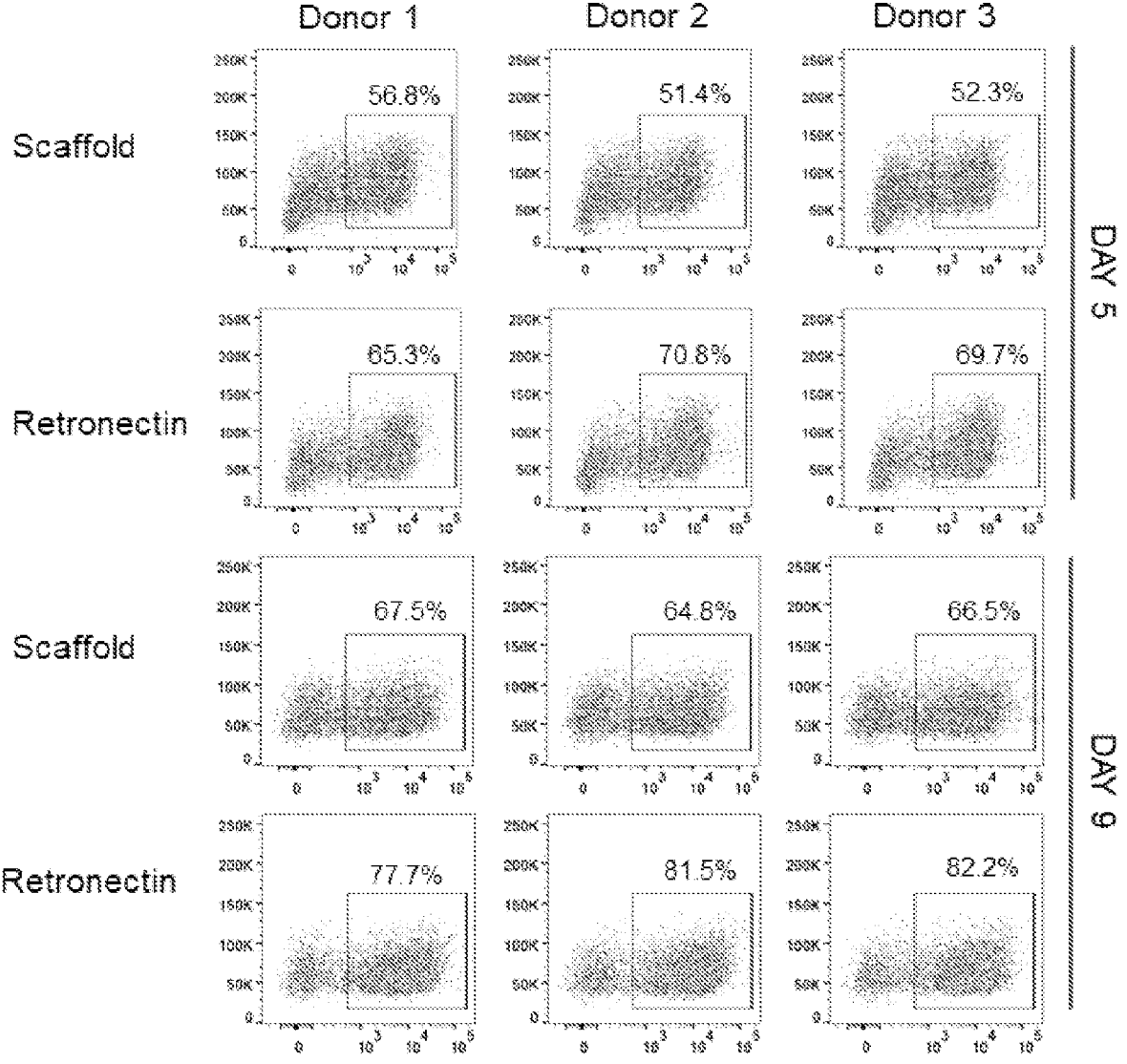

16. FIG. 3B shows FACS analysis of T cells on Day 5 and Day 9 post transduction. T cells from three different donors were transduced with CD19.CAR encoding retrovirus on retronectin coated plates or scaffold and analyzed for CAR expression by flow cytometry.

Figure 4:
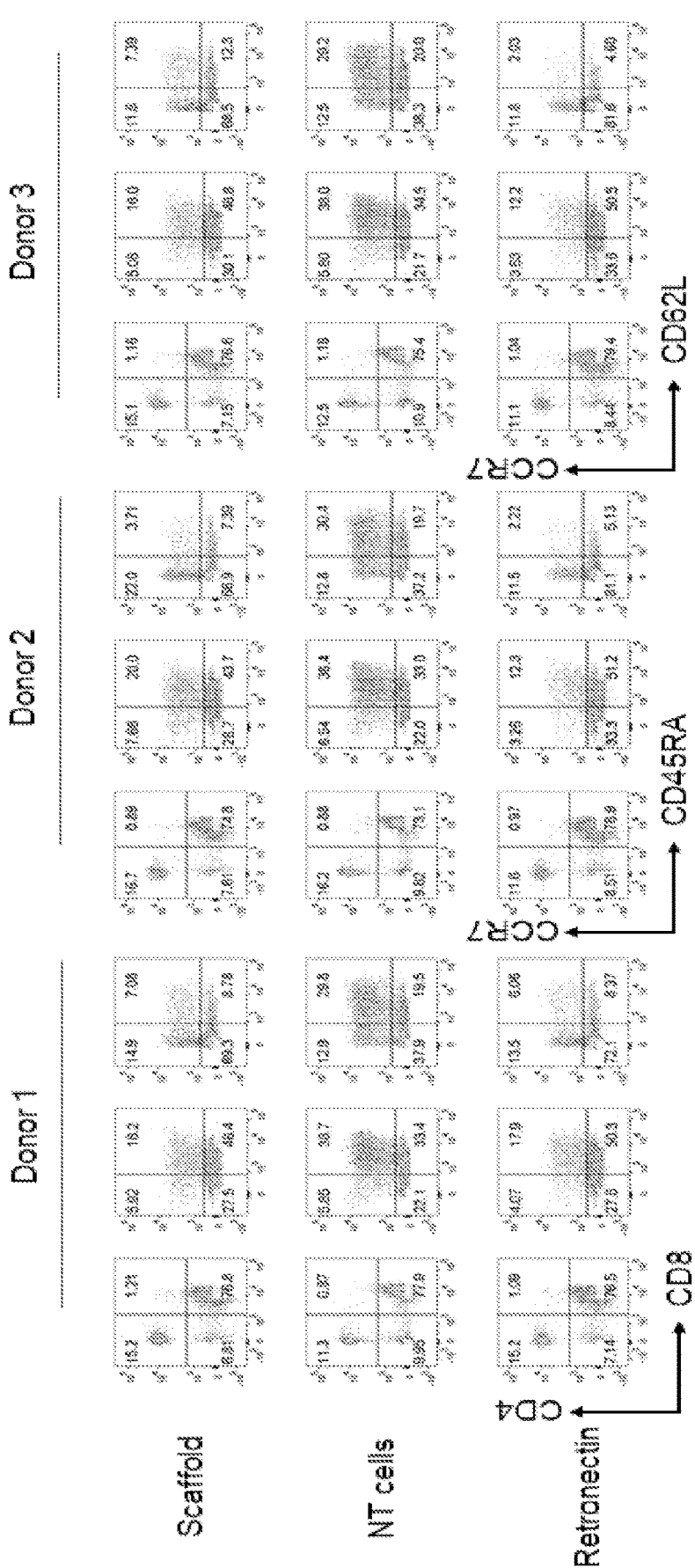

17. FIG. 4 shows CD4/CD8, CD45RA/CCR7, CD62L/CCR7 expression in CAR-T cells from 3 different donors generated by scaffold or retronectin mediated transduction. The analysis was performed gating on CAR-expressing cells except for NT-cells.

Figure 5:
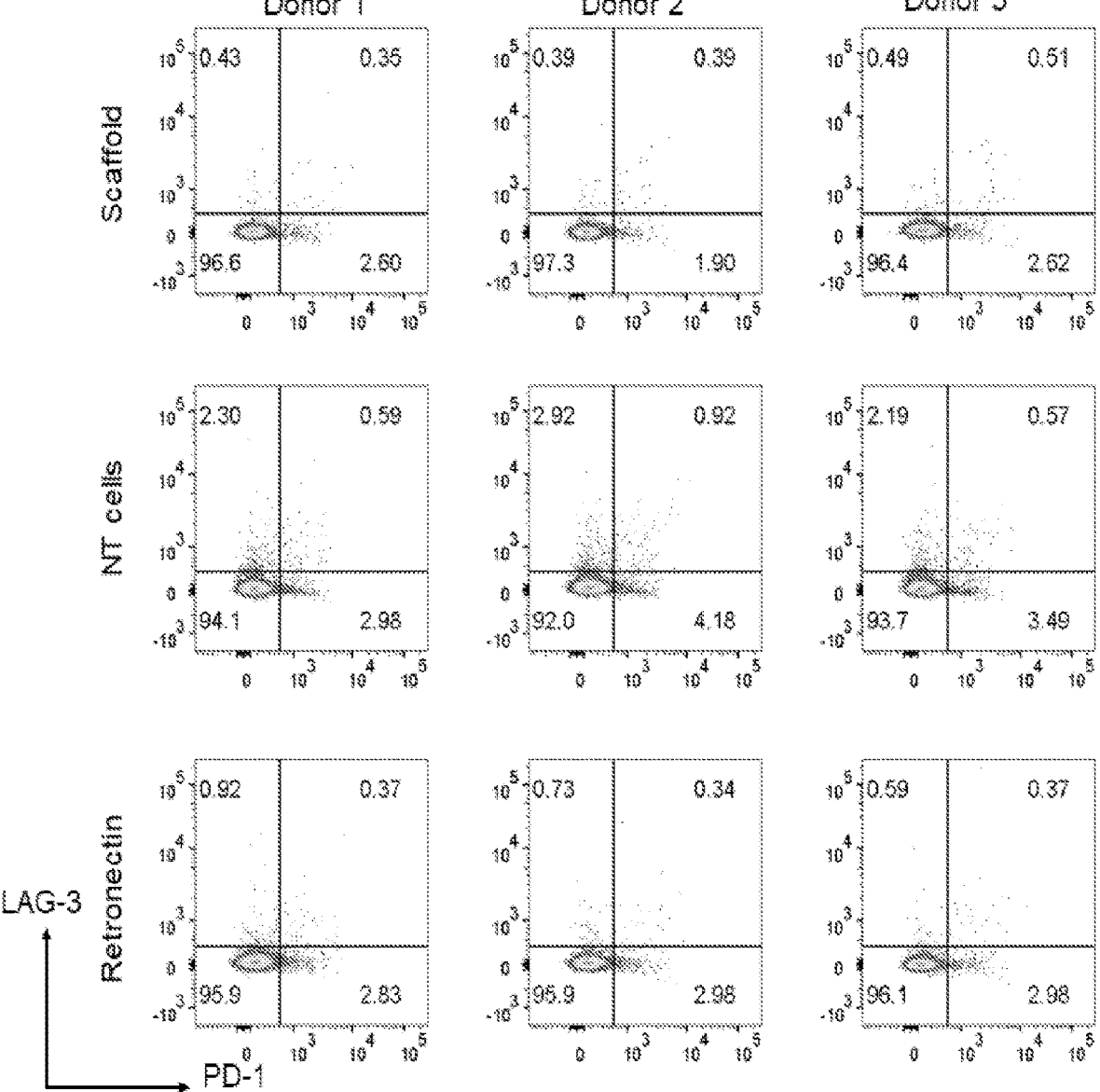

18. FIG. 5 shows PD-1/LAG3 expression (exhaustion markers) in CAR-T cells from 3 different donors generated by scaffold or retronectin mediated transduction. The analysis was performed gating on CAR-expressing cells except for NT-cells.

Figure 6:
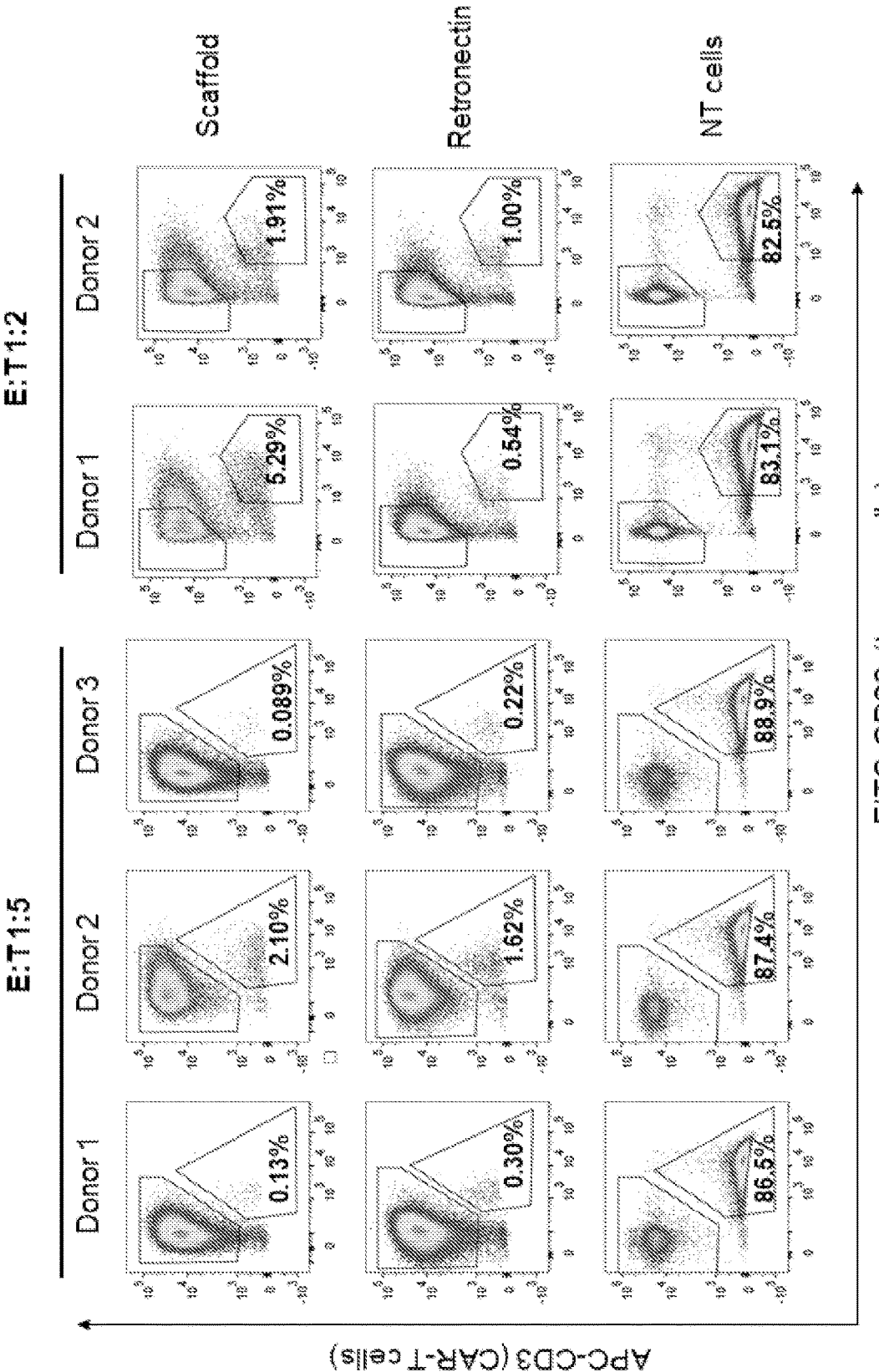

19. FIG. 6 shows that CAR-T cells generated by scaffold mediated transduction show toxicity against CD19+ tumor cells. CD19+ tumor cells were co-cultured with control non-transduced cells (NT cells) or CD19.CAR-T cells generated by sea fold mediated transduction or retronectin assisted spinoculation at 1:5 E:T ratio (left panel) and 1:2 E:T ratio (right panel) and analyzed by FACS on day 5 of co-culture.

Figure 7:
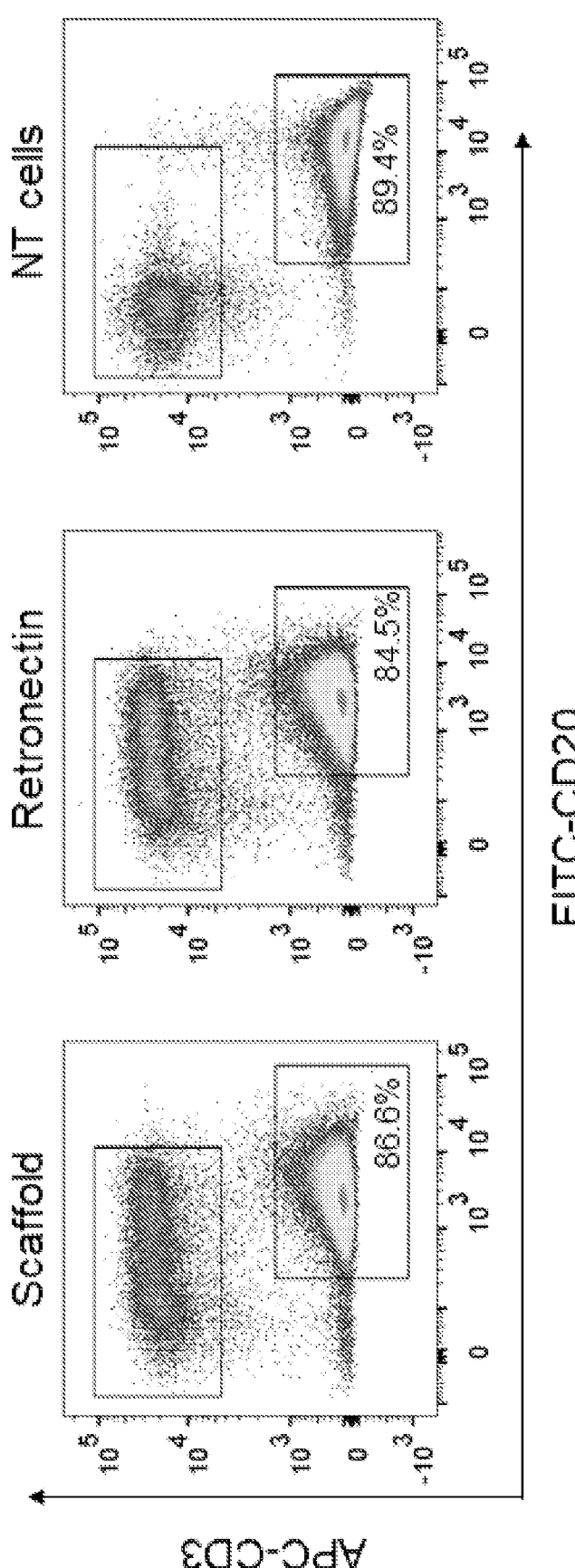

20. FIG. 7 shows that CAR-T cells generated by scaffold mediated transduction retains antigen specificity and its not functional against CD19– U937 tumor cells. CD19-tumor cells were co-cultured with control non-transduced cells (NT cells) or CD19.CAR-T cells generated by scaffold mediated transduction or retronectin assisted spinoculation at 1:5 E:T ratio and analyzed by FACS on day 5 of co-culture.

Figure 8:
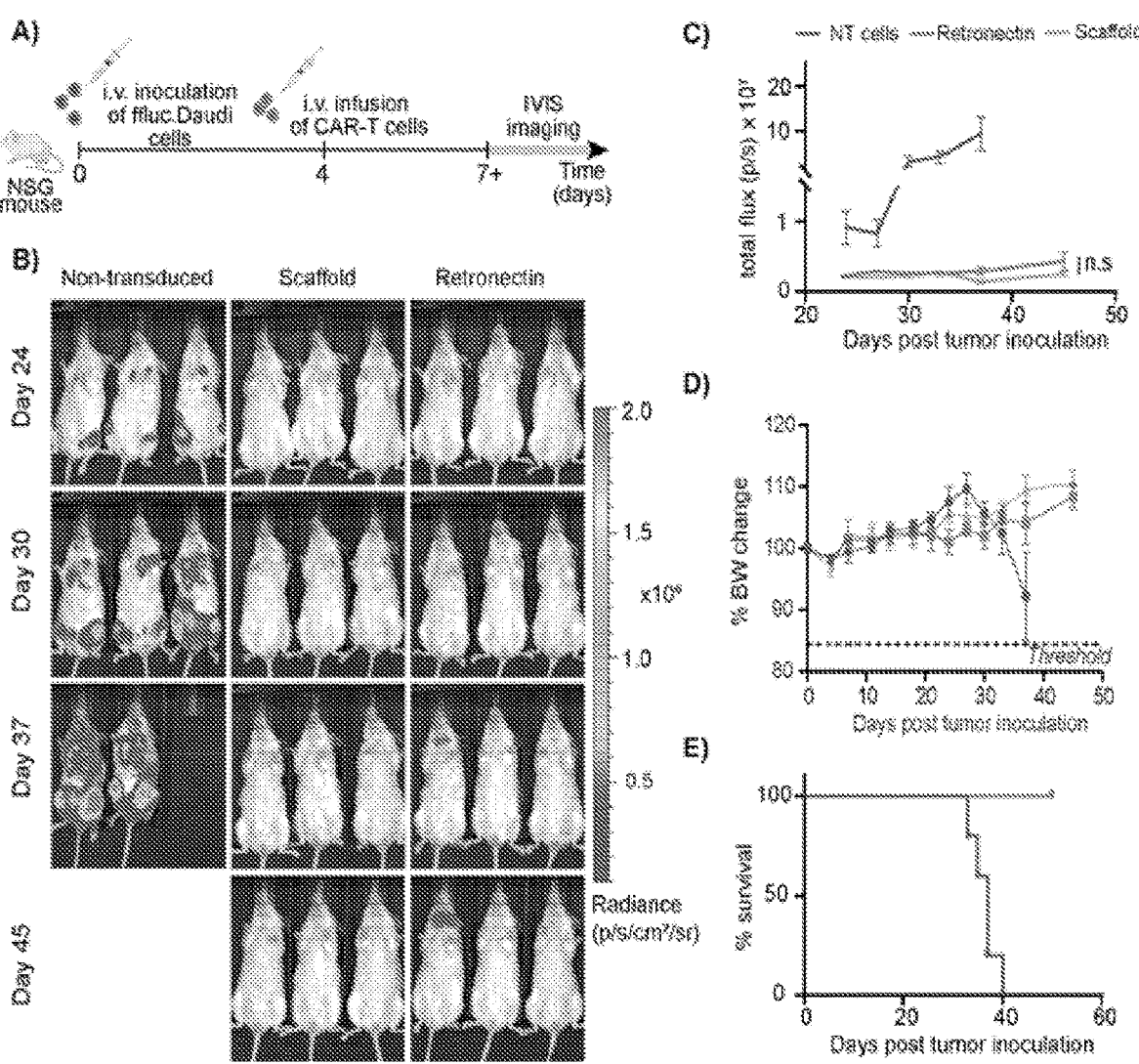

21. FIGS. 8A, 8B, 8C, 8D, and 8E show scaffold-generated CD19.CAR-T cells eradicate tumors in a mouse xenograft model of lymphoma. FIG. 8A shows experimental timeline of the lymphoma xenograft model in NSG mice using the FfLuc-labeled CD19⁺ human Daudi tumor cells. FIG. 8B shows representative tumor bioluminescent images (BLI) of NSG mice inoculated with Daudi cells and treated with control NT cells or treated with CD.19.CAR-T cells generated by scaffold-mediated transduction or retronectin/spinoculation-assisted transduction. FIG. 8C shows kinetics of tumor growth measured by quantification of BLI. **p<0.01 when scaffold or CAR-T cells were compared to control NT cells, one way ANOVA. FIGS. 8D and 8E show body weight change (8D) and survival (8E) of tumor-bearing mice treated with control NT cells on CD19.CAR-T cells generated by scaffold-mediated or retronectin/spinoculation assisted transduction. *p<0.05, log rank test.

Figure 9:
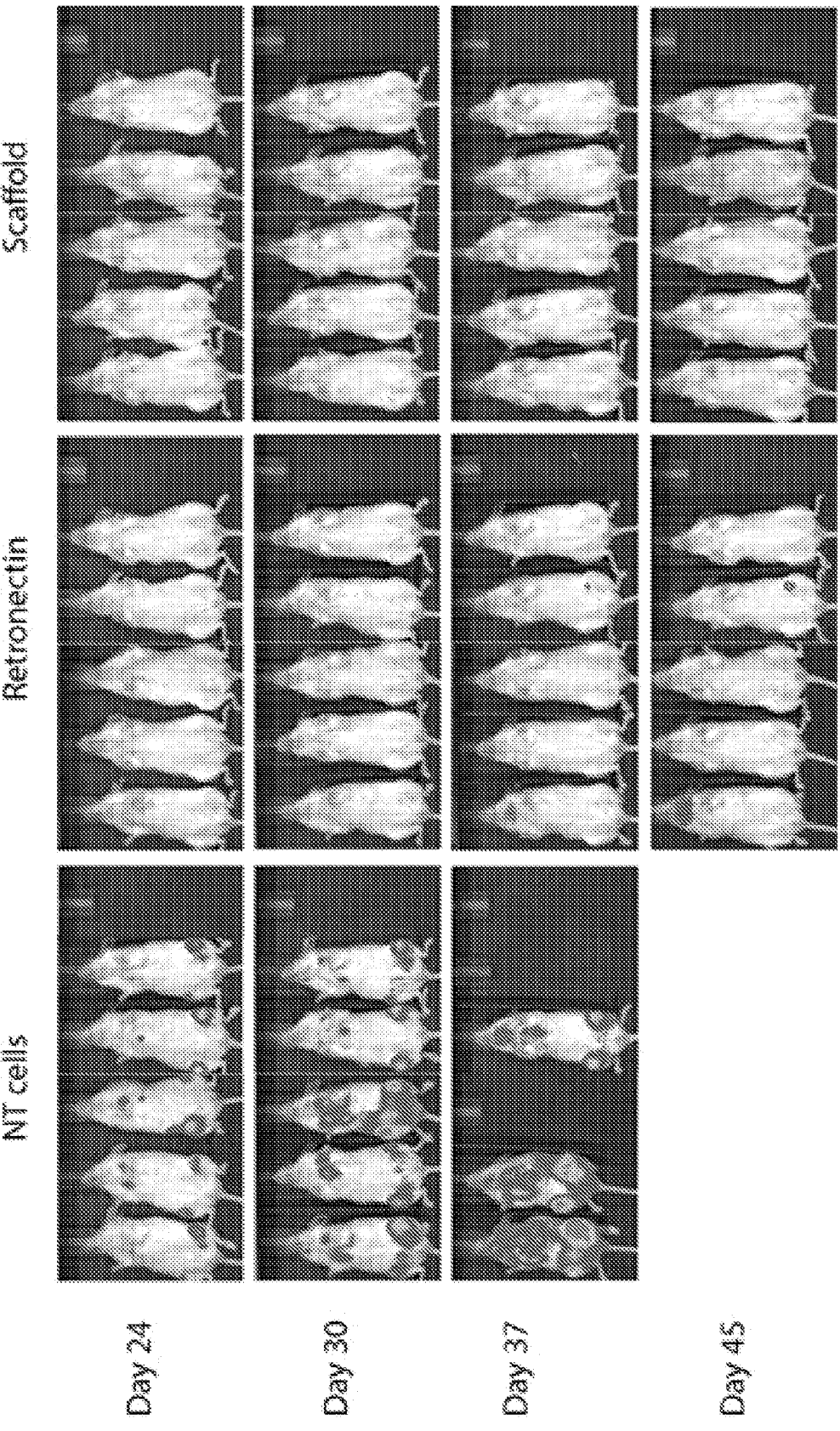

22. FIG. 9 shows IVIS™ images of NSG mice inoculated with luciferin-expressing Daudi cells on day 0, and then treated with non-transduced cells (NT cells) or treated with CD.19 CAR-T cells generated by scaffold-mediated transduction or retronectin-assisted spinoculation on day 4 post tumor inoculation.

23. FIG. 10A shows a schematic of DBCO-PEG$_4$-NHS conjugated anti-CD3 or antiCD28 antibody and the absorbance of the conjugated antibody relati e to the unmodified antibody.

24. FIGS. 10B and 10C show UV-absorption spectra of DBCO conjugated antibodies showing distinct absorption peak of DBCO at 309 nm.

25. FIG. 10D shows a synthetic scheme for azide-modified alginate.

26. FIG. 10E shows quantification of number of azides per alginate strand.

27. FIGS. 11A, 11B, 11C, 11D, 11E, 11F, and 11G show that MASTER (also referred to herein as CCI-A1g) promote activation and retrovirus-mediated transduction of primary human T cells. FIG. 11A shows a schematic for synthesis of (MASTER. FIG. 11B shows a SEM image of MASTER showing homogenous macroporous structure throughout the scaffold. FIG. 11C shows 3D confocal fluorescence micrograph of GFP$^+$ T cells in AF647 labeled MASTER, depicting cell distribution along the pores. FIG. 11D shows quantification of T cells expressing CD69, an early T cell activation marker. MASTER with increasing amounts of anti-CD3 and anti-CD28 antibodies were seeded with PBMCs and analyzed for CD69+ cells after 24 hours by flow cytometry FIG. 11E shows an overview of the process of MASTER-mediated T cell transduction. PBMCs and gamma retroviral particles are seeded on MASTER and incubated at 37° C. After Seventy-two hours, cells are collected from the scaffold and analyzed by flow cytometry. FIG. 11F shows representative flow cytometry plots showing GFP expression in T cells transduced on MASTER, blank scaffolds without anti-CD3 and anti-CD28 antibodies or by conventional spinoculation. Non-transduced cells were used as control. FIG. 11G shows FACS quantification of GFP$^+$ cells (***p<0.0001, one-way ANOVA with Tukey's correction).

Figure 12A:
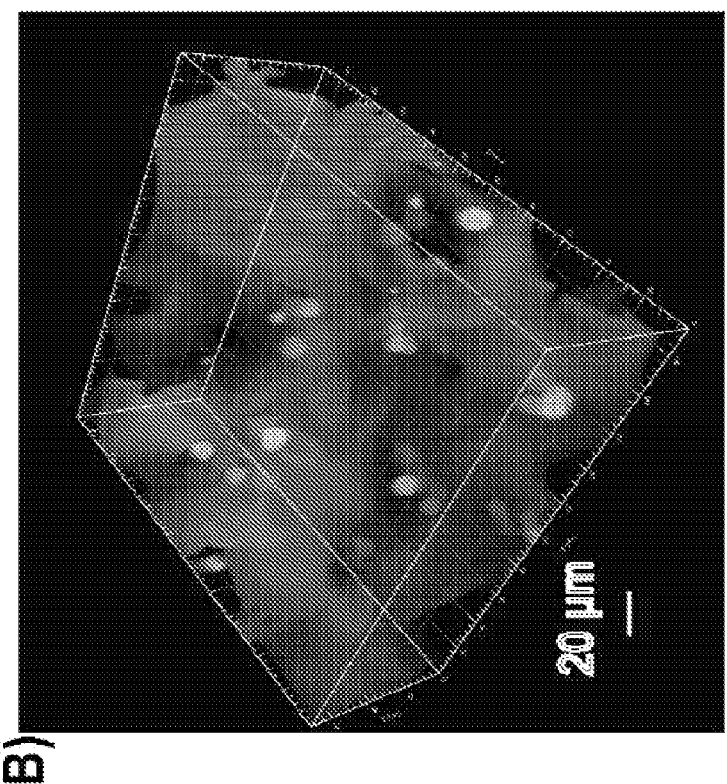
Figure 12B:
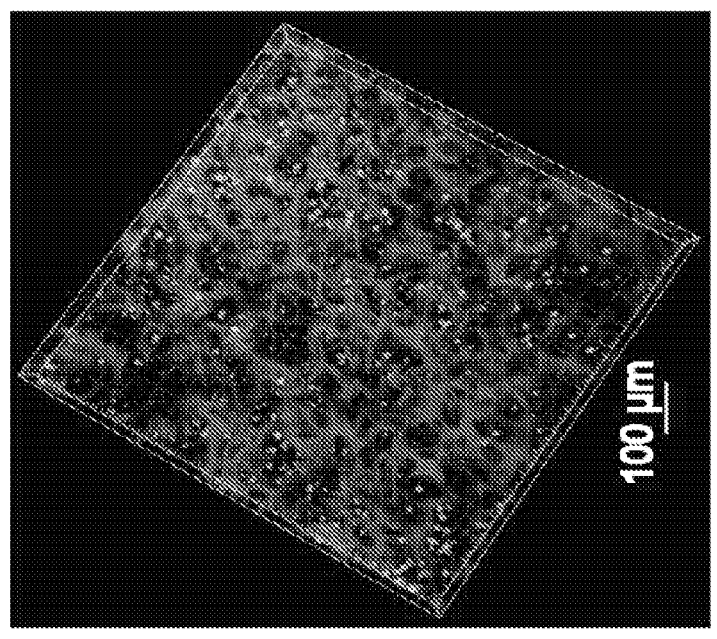

28. FIGS. 12A and 12B show 3D confocal micrograph showing distribution of GFP$^+$ T cells in AF647 labeled MASTER at 10X (12A) and 40X (12B) magnification.

29. FIGS. 13A, 13B, 13C, 13D, 13E, 13F, 13G, and 13H show MASTER-mediated gene transfer generates highly functional CAR-T cells. FIG. 13A shows flow cytometric plots depicting CD19.CAR expression in T cells transduced on MASTER. FIGS. 13B and 13C show immunophenotypic composition of CAR-T cells obtained via MASTER-mediated transduction of PBMCs or by conventional spinoculation of activated T cells at day 12 of culture. Non-transduced (NT) cells were used as control. Analysis was performed gating on CAR-expressing T cells except for NT cells. FIG. 13D shows FACS quantification of CAR$^+$ cells expressing PD-1 and/or LAG-3. FIG. 13E shows ex vivo expansion of non-transduced T cells (NT cells) or T cells transduced on MASTER or by spinoculation. FIG. 13F shows the percentage of viable CD19$^+$ Daudi cells when co-cultured with NT cells, CAR T cells obtained by MASTER or by spinoculation. Tumor cells and CAF T cells were plated at 1:5 effector to target ratio. T cells and tumor cells were quantified by low cytometry at day 5 of co-culture. FIGS. 13G and 13H show IFN-γ and IL-2 released into the co-culture supernatant by MASTER-generated, spinoculation-generated CAR-T cells and control NT cells after 24 hours as assessed by ELISA. ***P<0.0001; one-way ANOVA with Tukey correction. Data are represented as the mean±SD from three experiments, each derived from a different PBMC donor.

Figure 14:
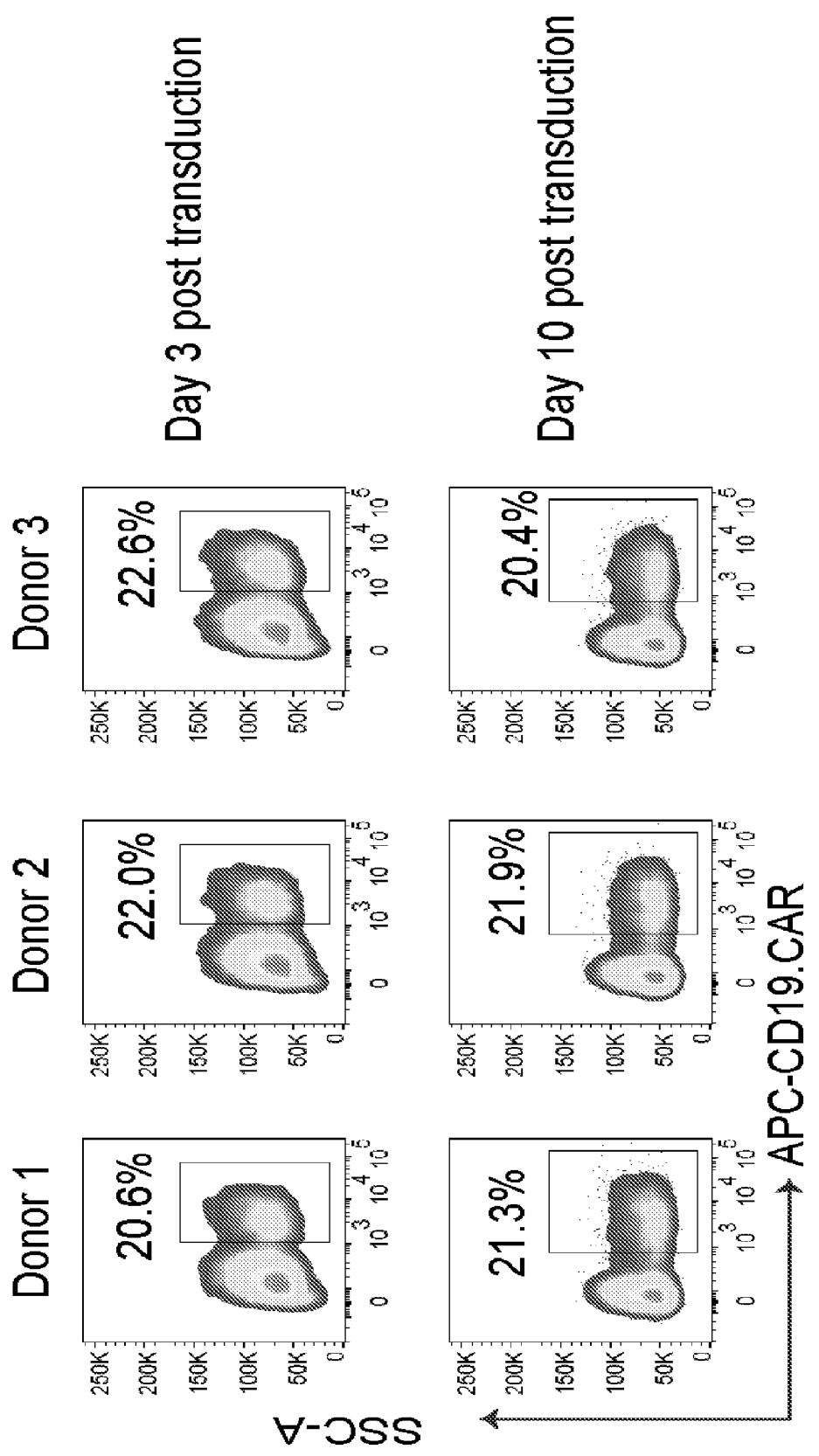

30. FIG. 14 shows FACS analysis of T cells on Day 3 and Day 10 post-transduction. T cells from three different donors were transduced with CD19.CAR encoding gamma retrovirus on MASTER and analyzed for CAR expression by flow cytometry.

Figure 15:
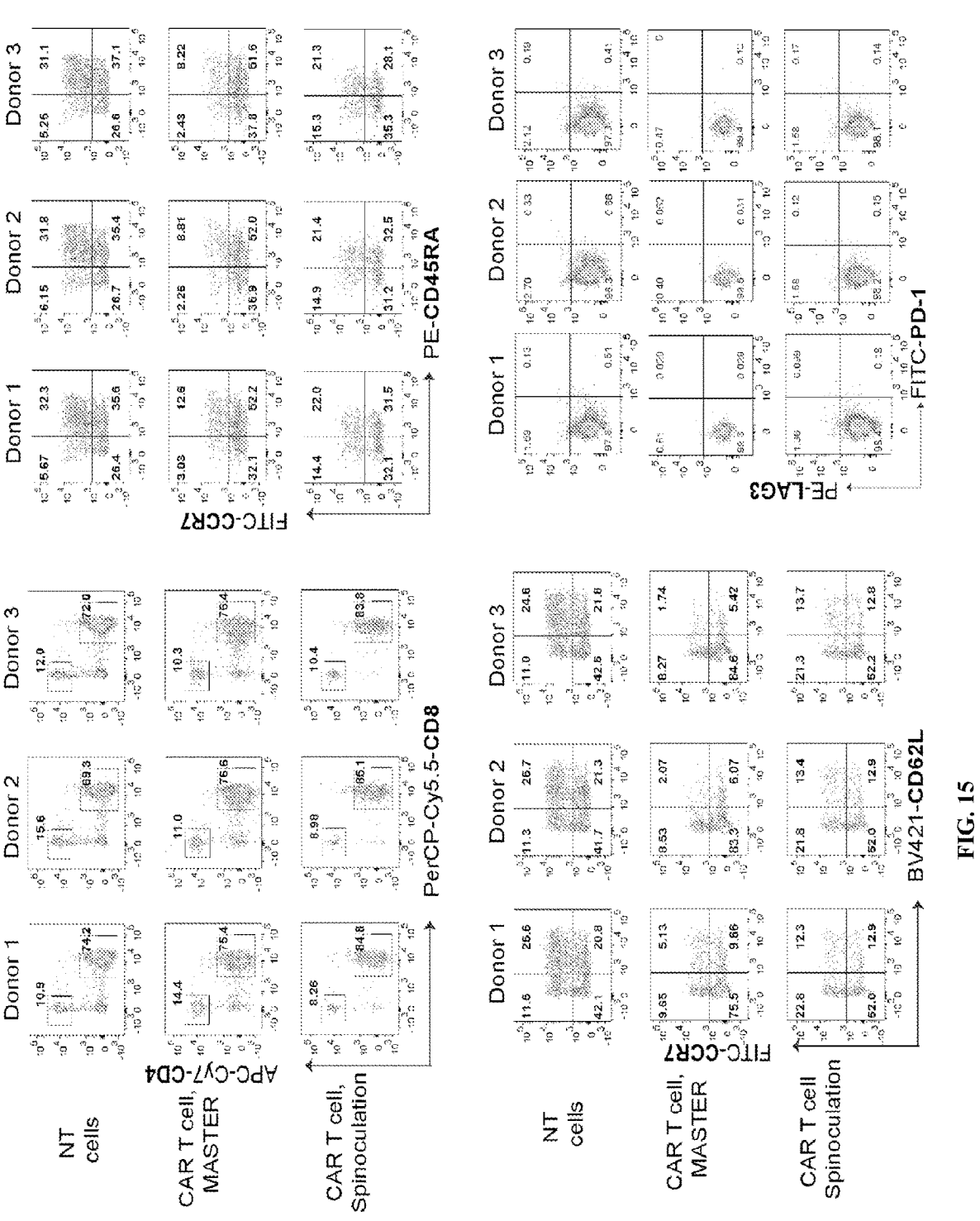

31. FIG. 15 shows CD4/CD8, CD45RA/CCR7, CD62L/CCR7, and PD-1/LAG3 expression in CAR-T cells from 3 different donors generated by MASTER or by spinoculation. The analyses were performed on CAR-expressing cells except for NT-cells.

Figures 16A, 16B:
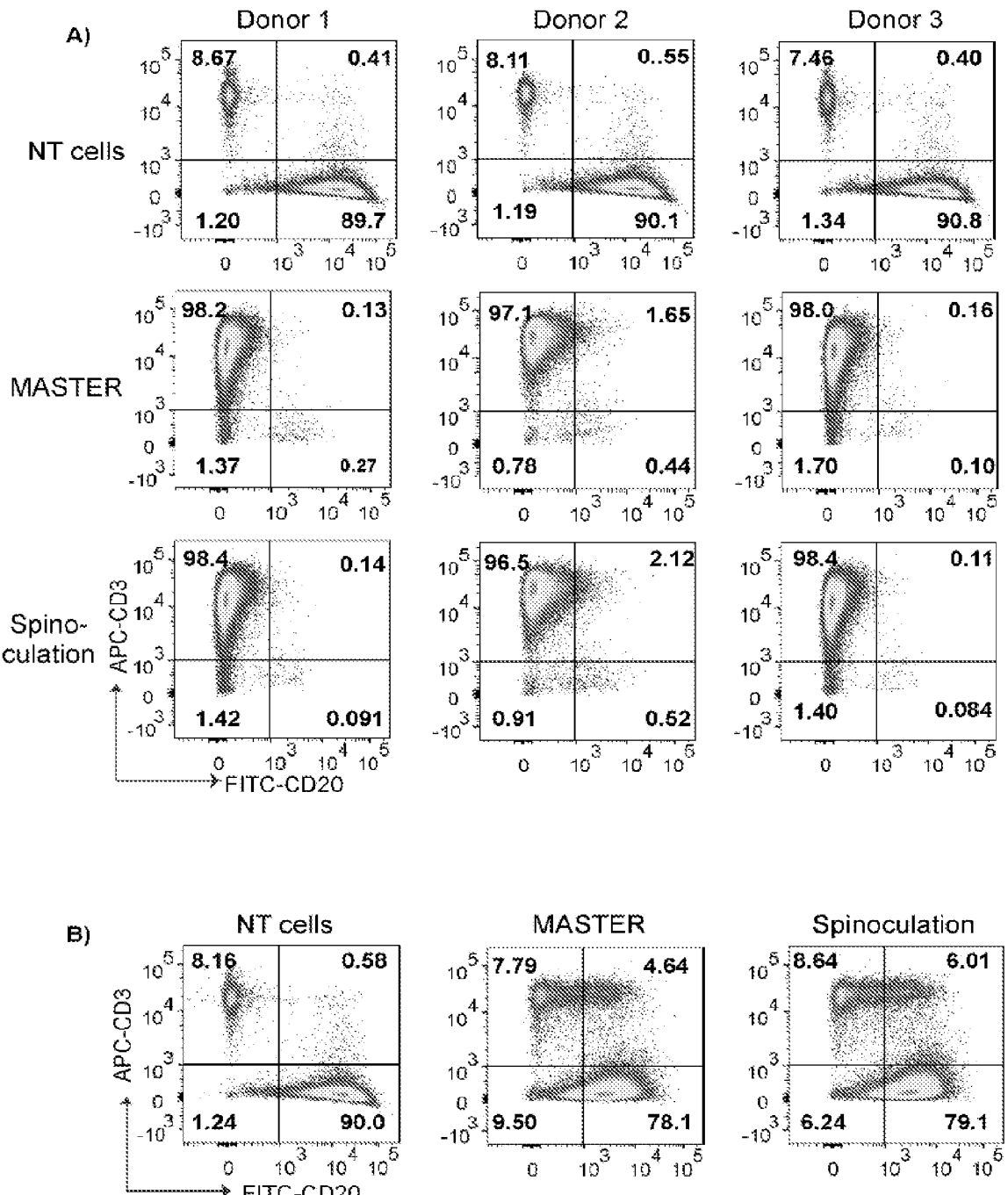

32. FIGS. 16A and 16B show that CAR-T cells generated by ASTER-mediated transduction show toxicity against CD19$^+$ tumor cells (16A) but not against CD19$^-$ U937 cells (16B). CD19$^+$ tumor cells or CD19$^-$ U937 cells were co-cultured with control non-transduced cells (NT cells) or CD19.CAR-T cells generated by MASTER mediated transduction or by spinoculation at 1:5 E:T ratio and analyzed by FACS on day 5 of co-culture.

Figures 17A, 17B:
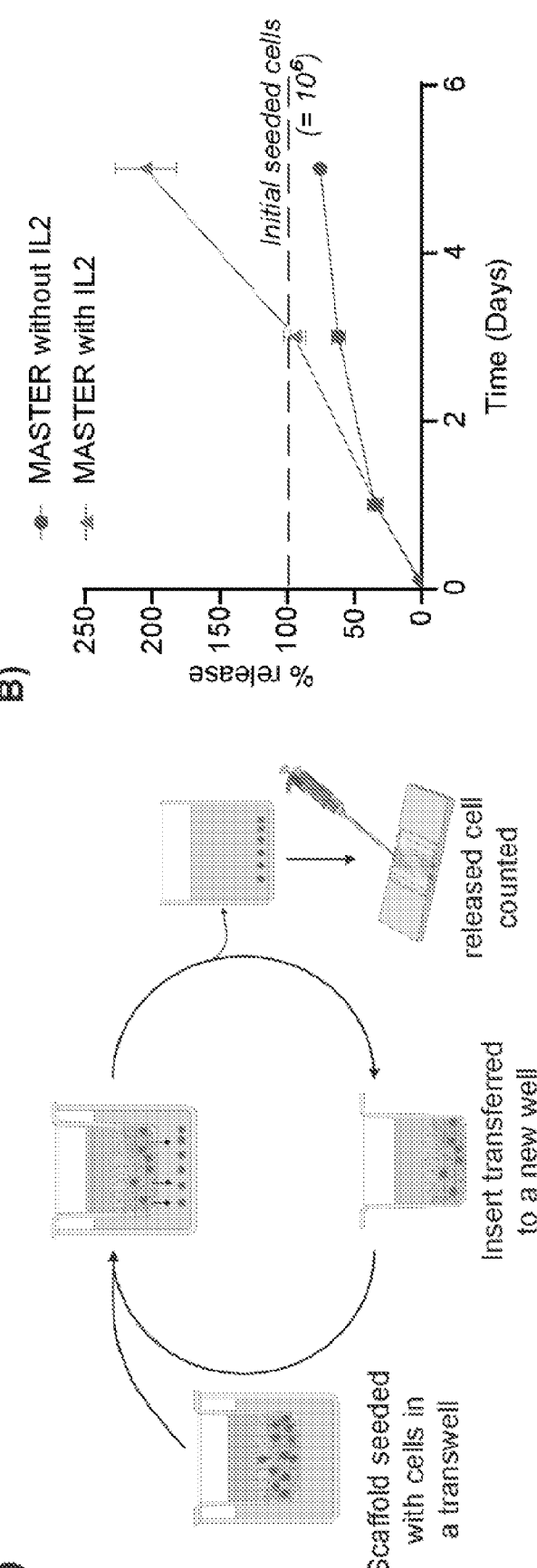

33. FIGS. 17A and 17B show that MASTER functions as an efficient T cell-release system. FIG. 17A shows a schematic of in vitro release study. FIG. 7B shows the percentage of cells released from scaffold.

34. FIGS. 18A, 18B, 18C, 189D, 18E, 18F, 18G, 18H, and 18I show that subcutaneously implanted MASTER generates and release fully functional CAR-T cells in a xenograft model of lymphoma. FIG. 18A shows the experimental timeline of the lymphoma xenograft model in NSG mice engrafted with FFLuc-labeled CD19$^+$ human Daudi tumor cells. FIG. 18B shows in vivo tumor bioluminescence imaging (BLI) of NSG mice treated with MASTER, conventional CAR-T cells or control non-transduced (NT) cells. FIG. 18C shows the kinetics of tumor growth measured by quantification of BLI. FIG. 18D shows the percentage change in body weight (BW) of treated mice. FIG. 18E shows the survival of mice shown as Kaplan-Meier curves. Six mice per treatment group are shown. p<0.01, Log-rank (Mantel-Cox) test, Gehan-Breslow-Wilcoxon test. FIG. 18F shows flow cytometric quantification of CD3$^+$CAR$^+$ cells in peripheral blood of mice described in (A). p<0.01, two-way ANOVA with Sidak's multiple comparison test. FIGS. 18G and 18H show quantification of CD3$^+$CAR$^+$ cells in bone marrow and spleen of nice euthanized on day 32 in the model described in (A) determined by flow cytometry p<0.01, one-way ANOVA with Tukey's correction. FIG. 18I shows analysis of exhaustion markers PD-1 and LAG3 expression in CAR$^+$ cells isolated from bone marrow of mice treated as described in (A). p<0.001, two-way ANOVA with Tukey's correction.

35. FIGS. 19A, 19B, and 19C show individual tumor growth curves of mice treated with NT cells (19A), MASTER (19B) or i.v. infused with CAR T cells 19C). Each line represents one animal. Data are shown for nine mice per treatment condition.

36. FIG. 20 shows the gating strategy for detection of CAR+ cells in blood, BM or spleen.

Figures 21A, 21B:
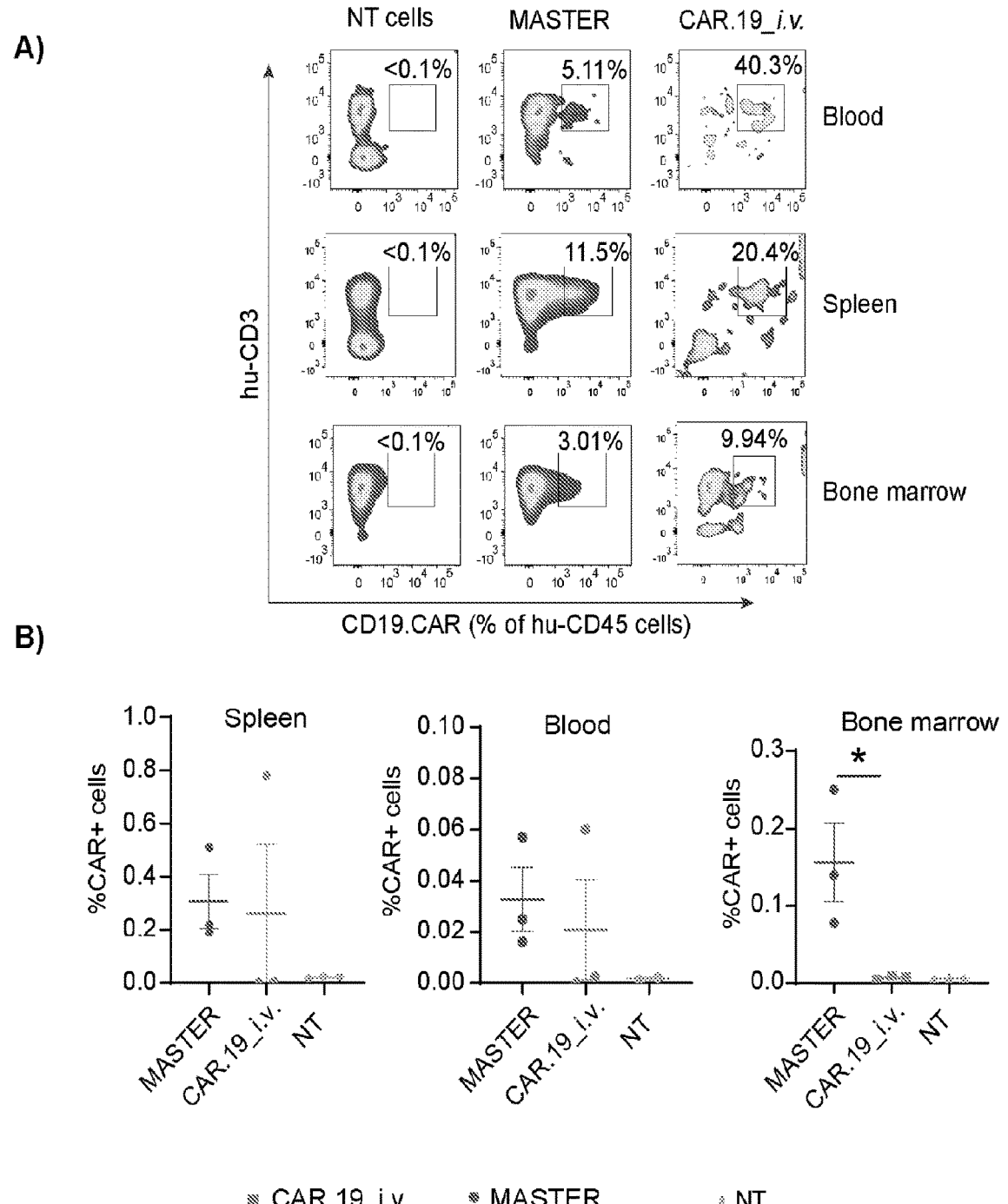

37. FIG. 21A shows a representative flow cytometry plots showing human CD45+CD3+CAR+ cells isolated from blood, bone marrow and spleen of mice (n=3) at day 32 post tumor cell inoculation.

38. FIG. 21B shows the percentage of human CD3+ CAR+ of total cells in in blood, bone marrow and spleen of mice euthanized at day 32 after tumor cell inoculation, as determined by flow cytometry.

Figure 22:
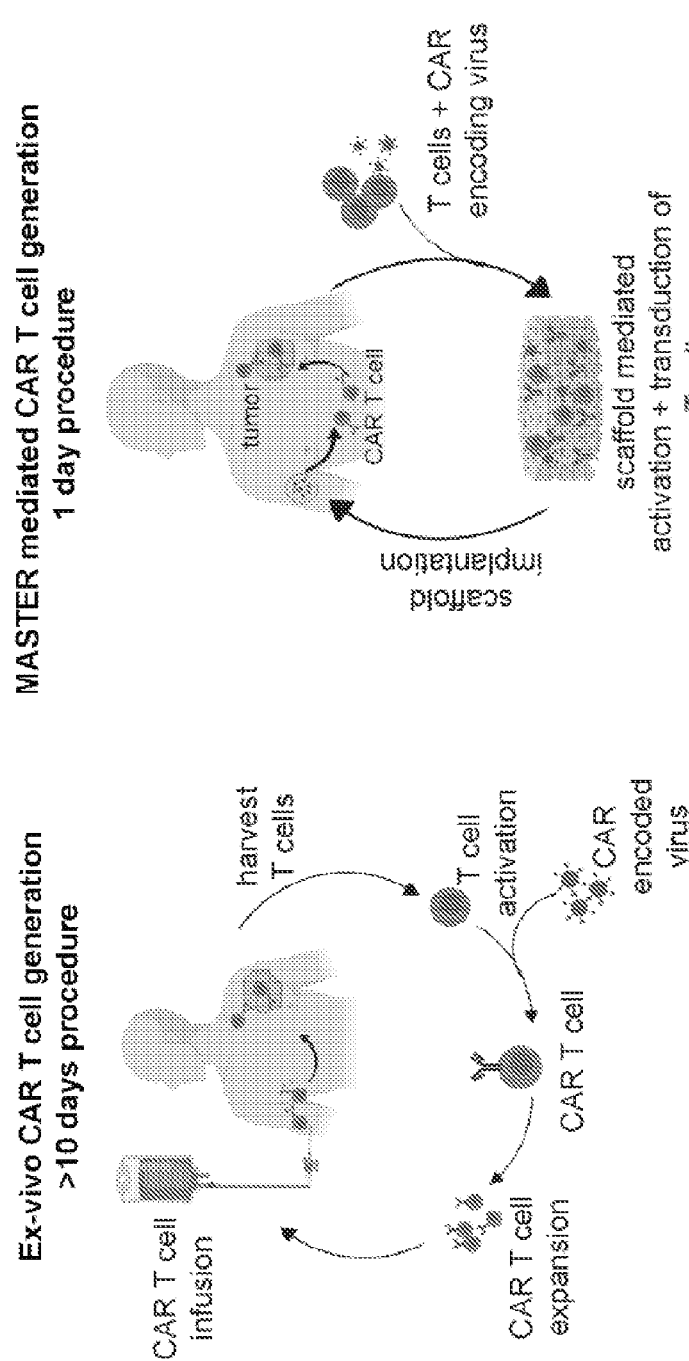

39. FIG. 22 shows a schematic showing conventional CAR-T cell therapy (left, ~4-week process) compared to rapid MASTER-mediated CAR T cell generation and therapy (right, 1 day process).

Figure 23:
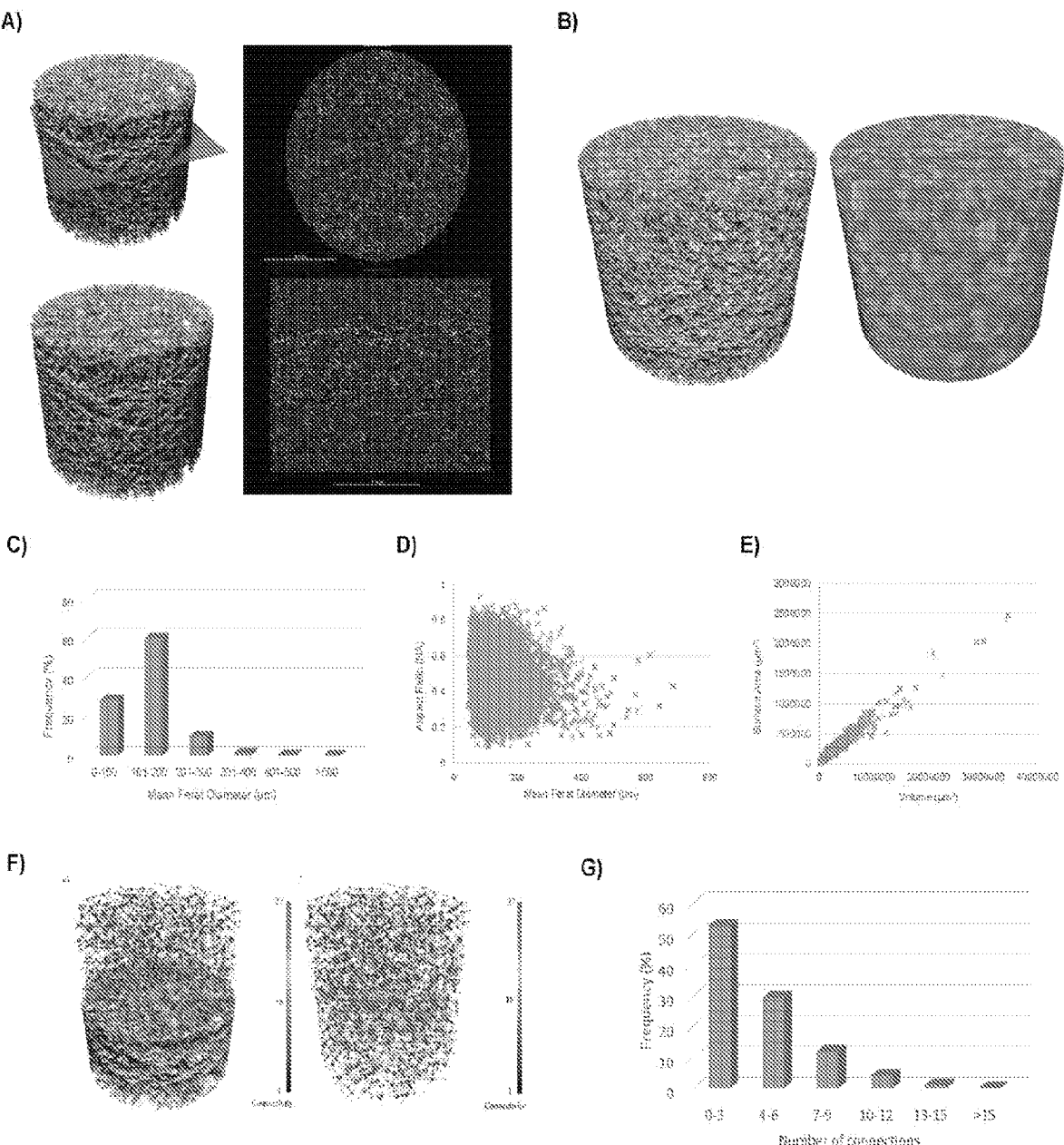

40. FIG. 23A shows the scanned volume of MASTER (left) with a colored plane indicating the cross-section seen on the right. In the cross sections a brighter value indicates a higher density (scaffolds) and a darker value a lower density (air porosity).

41. FIG. 23B shows the CT volume of MASTER (left) with pores isolated and color labeled (right). The color labeling of the pores is done so that pores with similar volumes have similar colors. The pores were isolated and analyzed individually and the calculated porosity was 75.8%

42. FIG. 23C shows relative frequency of pores of different dimensions.

43. FIG. 23D shows the aspect ratio of the pores showing most of the pores has an oblong shape. An aspect ratio of 1 corresponds to a sphere and close to corresponds to a flat plane or stick.

44. FIG. 23E shows the surface area as a function of volume plotted. The total surface area inside of MASTER is roughly 810 mm.

45. FIG. 23F shows connectivity between pores in the scaffold. The center, or node, of a pore is displayed as a sphere and from that sphere lines are drawn to other pores that it is connected to. The more connections the larger the sphere, the spheres are also color coded to show how many pores that connect to it. A partial cut into sample showing the connectivity (left) and full the connectivity in sample (right).

46. FIG. 23G shows connectivity of sample showing most of t e pores are connected with 0-3 other pores with a very few pores (around 6%) have more connections than 9.

Figure 24:
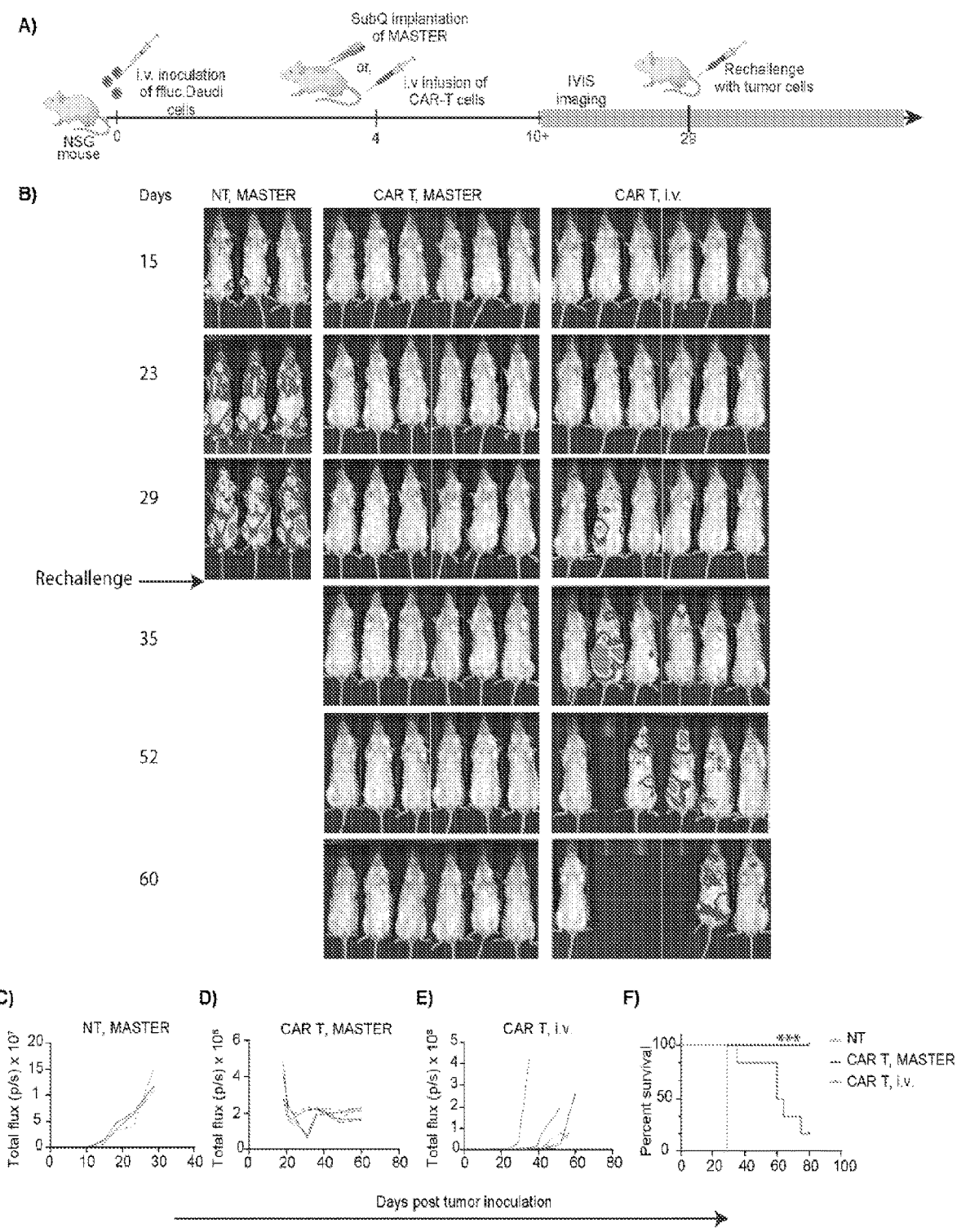

47. FIGS. 24A, 24B, 24C, 24D, 24E, and 24F show that MASTER exhibits enhanced activity in controlling tumor after tumor rechallenge as comp red with i.v. infusion of CAR T cells. FIG. 24A shows experimental timeline of the lymphoma xenograft model in NSG mice engrafted and rechallenged with FFLuc- labeled CD19+ human Daudi tumor cells. FIG. 24B shows in vivo tumor bioluminescence imaging (BLI) f NSG mice treated with MASTER, conventional CAR-T cells or control non-transduced (NT) cells. FIGS. 24C, 24D, and 24E show Individual tumor growth curves of mice treated with NT cells (24C), MASTER (24D) or i.v. infused with CAR T cells (24E). Each line represents one animal. FIG. 24F shows survival of mice shown as Kaplan- Meier cmves. Six mice per treatment group are shown.**p<0.01, Log-rank (Mantel-Cox) test, Gehan-Breslow-Wilcoxon test.

Figure 25:
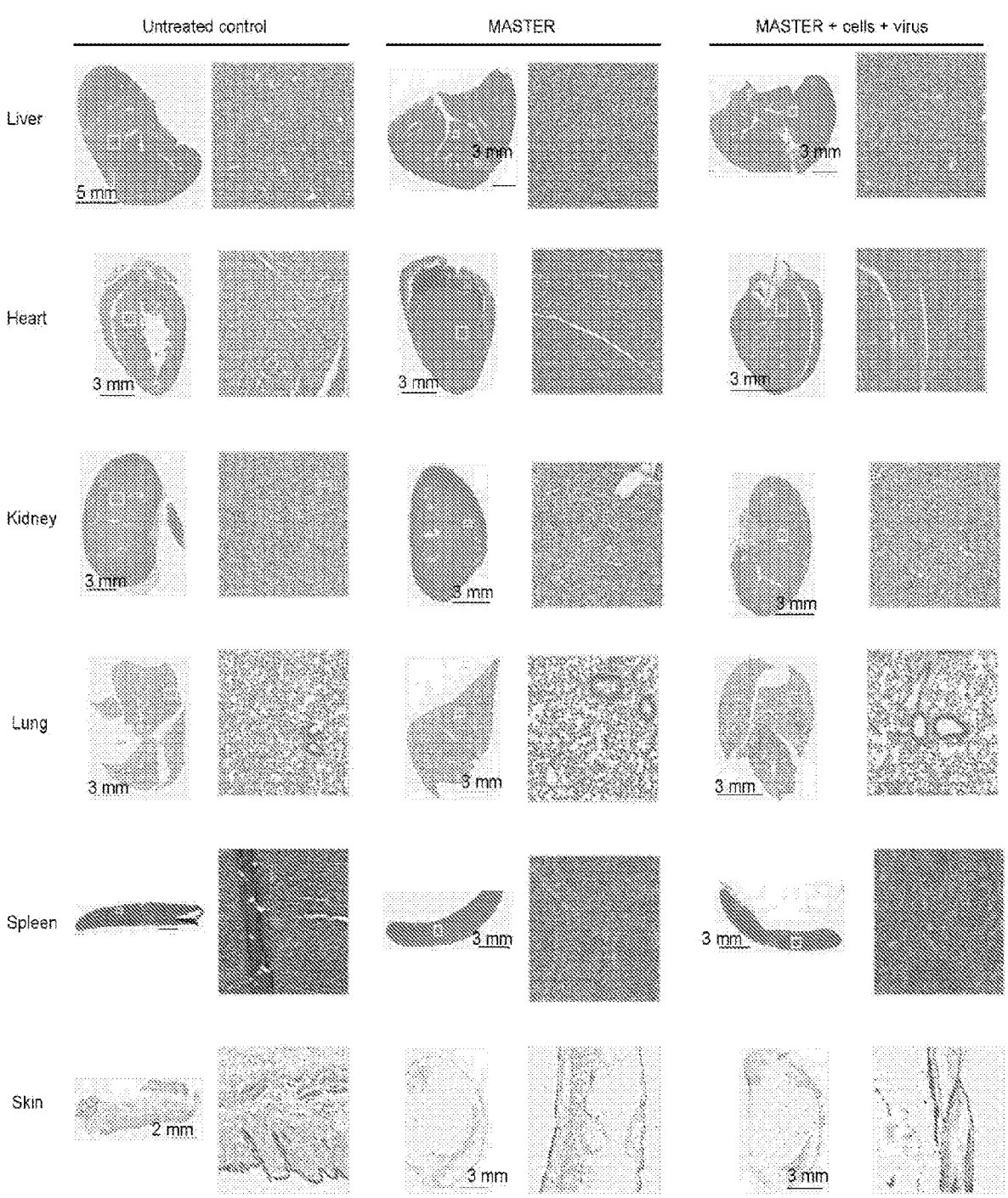

48. FIG. 25 shows the biocompatibility of MASTER and its co ponents. Representative images of H&E-stained sections of five major organs an implantation site four weeks after subcutaneous implant of MASTER, MASTER+mouse PBMCs+GFP encoded gamma retrovirus and untreated controls in C57B16/J immunocompetent mice.

49. FIG. 26 shows the biocompatibility of MASTER and its components as revealed by biochemical analysis of mouse blood. MASTER, MASTER+mouse PBMCs+GFP encoded gamma retrovirus were implanted in the subcutaneous space of C57B16/J immunocompetent mice (n=3).

Figure 27A:
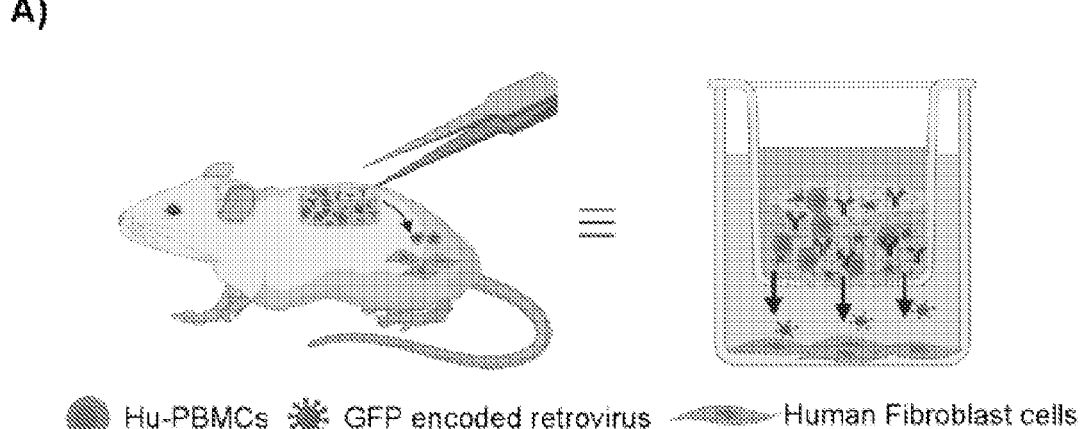
Figure 27B:
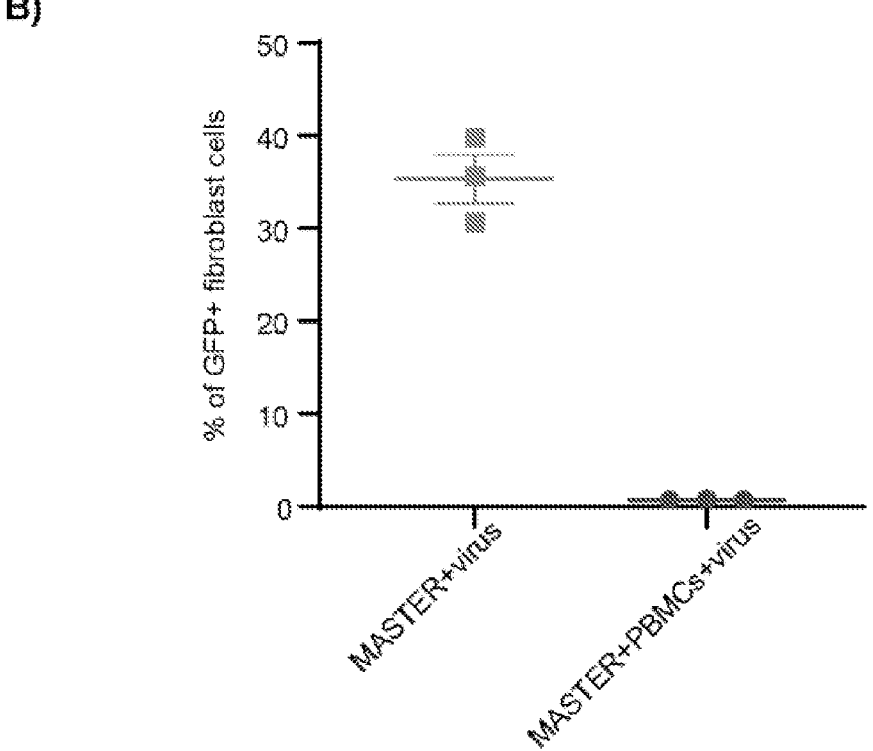

50. FIGS. 27A and 27B shows that MASTER loaded with PBMCs and retrovirus does not transduce host cells. FIG. 27A shows in vitro transwell mode mimicking the in vivo system. FIG. 27B shows GFP expression in fibroblast cells seeded on the bottom of transwell plate showing virus doesn't leak out of scaffold when MASTER is co-seeded with PBMCs and virus (MOI 2).

51. FIG. 28 shows that dry scaffold was seeded with 1 million HEK293T cells and GFP encoding lentivirus (MOI 2). Cells were isolated from scaffold after 72 h and GFP expression was measured.

IV. DETAILED DESCRIPTION

52. Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

53. In this specification and in the claims which follow, reference will be made to a number of terms which shall be defined to have the following meanings:

54. As used in the specification and the appended claims, the singular forms "a," "an" and "the" include plural references unless the context clearly dictates otherwise. Thus, for example, reference to "a pharmaceutical carrier" includes mixtures of two or more such carriers, and the like.

55. Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "bout" that particular value in addition to the value itself. For example, if the value "10" is disclosed, then "about 10" is also disclosed. It is also understood that when a value is disclose that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

56. Administration" to a subject includes any route of introducing or delivering to a subject an agent. Administration can be carried out by any suitable roue, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration n combination", "simultaneous administration" or "administered simultaneously" as use herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

57. "Biocompatible" generally refers to a material and any metabolites or degradation products thereof that are generally non-toxic to cells in culture or to a recipient organism and do not cause significant adverse effects to the subject.

58. "Comprising" is intended to mean that the compositions, methods, etc. include the recited elements, but do not exclude other's. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

59. A "control" is an alternative subject or sample used in an experiment for comparison purposes. A control can be "positive" or "negative."

60. "Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

61. "Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

62. A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

63. The disclosed hydrogels and dry scaffolds can comprise a vector encoding exogenous genes and other nucleic acids (such as, for example, siRNA, tasiRNA, lncRNA, shRNA, mRNA, gRNA, miRNA). As used herein, the term "exogenous" refers to nucleic acid from an external source including but not limited to engineered genes siRNA, tasiRNA, lncRNA, shRNA, mRNA, gRNA, miRNA, and/or DNA encoding said siRNA, tasiRNA, lncRNA, shRNA, mRNA, gRNA, miRNA.

64. "Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 63, 70, 80, 90, 100%, or any amount of reduction in between as compared to native or control levels.

65. The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

66. "Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

67. "Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

68. "Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

69. "Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

70. "Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or di ease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

71. In this specification and in the claims which follow, reference will be made to a number of terms which shall be defined to have the following meanings:

72. "Optional" or "optionally" means that the subsequently described event or circumstance may or may not occur, and that the description includes instances where said event or circumstance occurs and instances where it does not.

73. Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

74. Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular hydrogel matrix and/or dry scaffold is disclosed and discussed and a number of modifications that can be made to a number of molecules including the hydrogel matrix and/or dry scaffold are discussed, specifically contemplated is each and every combination and permutation of hydrogel matrix and/or dry scaffold and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus if there are a variety of additional steps that can be performed it is understood that each of these additional steps can be performed with any specific embodiment or combination of embodiments of the disclosed methods.

75. We have developed a three dimensional (3D) dry macroporous scaffold as an efficient, single-step, static platform to engineer T cells with RV vector. We hypothesized that 3D dimensional scaffolds with macroporosity and high water absorbing capability would allow colocalization of RV particles and T cells as achieved by using retronectin. We prepared dry macroporous scaffolds from calcium-cross-linked alginate, which is a GMP-compliant and FDA-approved biomaterial extensively used for many biomedical applications due to its biocompatibility, low toxicity, low cost, and mild gelation by divalent cations. We observed that dry, hygroscopic and dry macroporous alginate scaffolds facilitate the interaction of RV vectors and cells (including immune cells such as T cells and non-immune cells) and enables efficient nucleic acid transfer (including genes, siRNA, tasiRNA, lncRNA, shRNA, mRNA, gRNA, and/or miRNA) in a single step without spinoculation and without affecting functionality and viability of the recipient cell. Thus, these scaffolds represent a simple, cost effective and tunable platform technology for generating highly functional engineered cells including, but not limited to T cells for adoptive cellular therapy.

76. Accordingly, in one aspect, disclosed herein are biocompatible hydrogel matrixes and/or dry scaffolds (such as, for example, hydrogels and/or dry scaffolds comprising alginate) comprising one or more ligands or antibodies specific for a cel receptor or protein (including, but not limited to a T cell receptor and/or NK cell receptor, such as, for example, an anti-CD3 antibody, CD1d, an Fc fragment of an immunoglobulin, or anti-Fc gamma receptor (FcγRIII)

antibody). The disclosed hydrogel matrixes and/or dry scaffolds can be scaffolds used for transducing cells (such as, for example, non-immune cells and immune cells including but not limited to T cells, natural killer (NK) cells, NK T cells, macrophage, tumor infiltrating lymphocytes (TILs), Tumor infiltrating NK cells (TINKs), and/or a marrow infiltrating lymphocytes (MILs)) and making chimeric antigen receptor (CAR) cells. Accordingly, in one aspect, the hydrogel matrixes and/or dry scaffolds can comprise a vector (such as, for example, a lentivirus, retrovirus, adenovirus, adeno-associated virus, virus-like particle, transposon, or liposome) encoding and/or encapsulating an exogenous gene, siRNA, tasiRNA, lncRNA, shRNA, mRNA, gRNA, miRNA, and/or DNA encoding said siRNA, tasiRNA, lncRNA, shRNA, mRNA, gRNA, miRNA (including, but not limited to engineered genes, siRNA, tasiRNA, lncRNA, shRNA, mRNA, gRNA, and/or miRNA, such as, for example, a chimeric antigen receptor (CAR) gene).

77. The device, e.g., hydrogel, structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into scaffold using methods known in the art, e.g., injection molding, lyophilization of preformed structures, printing self-assembly, phase inversion, solvent casting, melt processing, gas foaming, fiber forming/processing, particulate leaching or a combination thereof.

78. The hydrogels and/or dry scaffolds disclosed herein can be made using any suitable biodegradable polymer. "Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, add tion polymers, etc.

79. Exemplary materials used to form the device, e.g., hydrogel, include polylactic acid, polyglycolic acid, poly-lactide-co-glycolide (PLG), alginates and alginate derivatives, gelatin, collagen, fibrin, fibronectin, methacrylamide, acrylamide, decellularized tissues, hyaluronic acid, laminin rich gels, agarose, natural and synthetic polysaccharides, polyamino acids, polypeptides, polyesters, polyanhydrides, polyphosphazines, poly vinyl alcohols), poly(alkylene oxides), poly(allylamines)(PAM), poly(acrylates), modified styrene polymers, pluronic polyols, polyoxamers, poly (uronic acids), poly(vinylpyrrolidone) and copolymers or graft copolymers of any of the above.

80. One preferred hydrogel includes an RGD-modified alginate. In other examples, the hydrogel includes cross-linked polymers, e.g., crosslinked alginates, gelatins, or derivatives thereof, such as those that are methacrylated.

81. In one aspect, the hydrogel and/or dry scaffold can comprise a biocompatible polymer (such as, for example, alginate). Such polymers can also serve to slowly release CAR T cell, CAR NK cell, TIL, and/or MIL into the tissue. As used her in biocompatible polymers include, but are not limited to polysaccharides; hydrophilic polypeptides; poly (amino acids) such as poly-L-glutamic acid (PGS), gamma-polyglutamic acid, poly-L-aspartic acid, poly-L- serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly (hydroxyalkylmethacrylamide); poly(hydroxyalkylmeth-acrylate); poly(saccharides); poly(hydroxy acids); poly(vi-nyl alcohol), polyhydroxyacids such as poly(lactic acid), poly(gly colic acid), and poly (lactic acid-co-glycolic acids); polyhydroxyalkanoates such as poly3-hydroxybutyrate or poly4-hydroxybutyrate; polycaprolactones; poly(orthoe-sters); polyanhydrides; poly(phosphazenes); poly(lactide-co-caprolactones); polycarbonates such as tyrosine polycar-bonates; polyamides (including synthetic and natural polyamides), polypeptides, and poly(amino acids); polyes-teramides; polyesters; poly(dioxanones); poly(alkylene alkylates); hydrophobic polyethers; polyurethanes; polyetheresters; polyacetals; polycyanoacrylates; polyacry-lates; polymethylmethacrylates; polysiloxanes; poly(oxy-ethylene)/poly(oxypropylene) copolymers; polyketals; poly-phosphates; polyhydroxyvalerates; polyalkylene oxalates; polyalkylene succinates; poly(maleic acids), as well as copolymers thereof. Biocompatible polymers can also include polyamides, polycarbonates, polyalkylenes, polyal-kylene glycols, polyalkylene oxides, polyalkylene terepthalates, polyvinyl alcohols (PVA), methacrylate PVA(m-PVA), polyvinyl ethers, polyvinyl esters, polyvinyl halides, poly-vinylpyrrolidone, polyglycolide, polysiloxanes, polyure-thanes and copolymers thereof, alkyl cellulose, hydroxyal-kyl celluloses, cellulose ethers, cellulose esters, nitro celluloses, polymers of acrylic and methanolic esters, methyl cellulose, ethyl cellulose, hydroxypropyl cellulose, hydroxy-propyl methyl cellulose, hydroxybutyl methyl cel-lulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly (butylmethacrylate), poly(isobutylmethacrylate), poly(hex-ylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene tere-phthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene amines), poly(caprolactones), poly (hydroxybutyrates), poly(hydroxyvalerates), polyanhy-drides, poly(acrylic acids), polyglycolides, poly(urethanes), polycarbonates, polyphosphate esters, polyphospliazenes, derivatives thereof, linear and branched copolymers and block copolymers thereof, and blends thereof.

82. In some embodiments the particle contains biocom-patible and/or biodegradable polyesters or polyanhydrides such as poly(lactic acid), poly(glycolic acid), and poly (lactic-co-glycolic acid). The particles can contain one more of the following polyesters: homopolymers including gly-colic acid units, referred to herein as "PGA", and lactic acid units, such as poly-L-lactic acid, poly-D-lactic acid, poly-D,L-lactic acid, poly-L-lactide, poly-D-lactide, and poly-D, L-lactide5 collectively referred to herein as "PLA", and caprolactone units, such as poly(e-caprolactone), collectively referred to herein as "PCL"; and copolymers including lactic acid and glycolic acid units, such as various forms of poly(lactic acid-co-glycolic acid) and poly(lactide-co-glycolide) characterized by t e ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. In one aspect, the polymer comprises at least 60, 65, 70, 75, 80, 85, 89, 90, 91, 92, 93, 94, 95, 96, 97, 98, or 99 percent acetal pendant groups. 83. The triblock copolymers disclosed herein comprise a core polymer such as, example, polyethylene glycol (PEG), polyvinyl acetate, polyvinyl alcohol, polyvinyl pyrrolidone (PVP), polyethyleneoxide (PEO), poly(vinyl pyrrolidone-co vinyl acetate), polymethacrylates, polyoxyethylene alkyl ethers, polyoxyethylene castor oils, polycaprolactam, polylactic acid, polyglycolic acid, poly (lactic-glycolic) acid, poly(lactic co-glycolic) acid (PLGA), cellulose derivatives, such as hydroxymethylcellulose, hydroxypropylcellulose and the like.

84. In some cases, components of the device, e.g., containing hydrogel, are organized in a variety of geometric shapes (e.g., discs, beads, pellets), niches, planar layers (e.g., thin sheets). For example, discs of about 0.1 millimeters to about 50 centime ers in diameter, e.g., 0.1, 0.2, 0.3, 0.4, 0.5, 0.6, 0.7, 0.8, 0.9, 1, 2, 3, 4, 5, 10, 15, 20, 25, 30, 35, 40, 45, 50, 60, 70, 80, 90 millimeters 10, 15, 20, 25, 30, 35, 40, 45, 50 centimeters in diam ter are implanted subcutaneously. The disc may have a thickness of 0.1 to 10 millimeters, e.g., 1, 2, 5 millimeters. The discs are readily compressed or lyophilized for administration to a patient. An exemplary disc for subcutaneous administration has the following dimensions: 8 millimeters in diameter and 1 millimeter in thickness. Multicomponent devices, e.g., containing hydrogels, are optionally constructed in concentric layers each of which is characterized by different physical qualities (% polymer, % crosslinking of polymer, chemical composition of the hydrogel, pore size, porosity, and pore architecture, stiffness, toughness, ductility, viscoelasticity, and/or pharmaceutical composition.

85. The scaffolds disclosed herein can be fabricated in or inserted into wells of a multi-well plate, including in 384-well, 96-well, 48-well, 24-well, 12-well, or 6-well plates. The scaffolds can be fabricated in or inserted into flasks, including T25, T75, T175, or T225 flasks. The scaffolds can be fabricated in or inserted into culture dishes, including 35 mm, 60 mm, 100 mm, and 150 mm dishes. Scaffolds can be fabricated in or inserted into cell culture tubes, including 3 mL, 5 mL, 7 mL, 8 mL 12 mL, 14 mL, 15 mL, 16 mL, 19 mL, 21 mL, or 50 mL capacity tubes. The scaffolds can be of arbitrary shape and size and fabricated in or inserted into molds, including molds of size in the range of 1 mm3 to 0.1 m3. The scaffolds can be fabricated in or inserted into cell culture bags of capacity 50 mL, 100 mL, 200 mL, 300 mL, 500 mL, 1000 mL, 2000 mL, 5000 mL, 10000 mL.

86. The scaffolds disclosed herein can be fabricated in wells of multi-well plates or in culture dishes and so have a disk shape with diameter between 1 mm and 50 cm and thickness 1 mm to 50 cm. The scaffolds can be fabricated in square or rectangular mold with side length 1 mm to 50 cm and thickness 1 mm to 50 cm. Additionally, the scaffold can be fabricated in molds that are regularly shared or irregularly shaped molds and have regular including triangular, pentagonal, hexagonal, star shaped, or diamond shaped or they can be irregularly shaped. Regular or irregular shaped molds can have a surface area of between 1 mm^2 to 2500 cm^2 and thickness of 1 mm to 50 cm.

87. The scaffolds can consist of a collection of individual particles. These microparticles can be manufactured through spray-drying, electrospinning, extrusion, emulsification/gelation, shredding, spin drying or other techniques known to make particles. An example of particles that make up the scaffolds could be microspheres that are 50 $\mu$m, 100 $\mu$m, 200 $\mu$m, 500 $\mu$m, 1000 $\mu$m, 2000 $\mu$m or 5000 $\mu$m in diameter. The scaffolds can also consist of sections cut from a larger manufactured whole. The original whole can be 0.1 meter square to 1,000 meter square in size.

88. The scaffold structure may contain pores which are microporous or macroporous. Pore size may include 10 $\mu$m, 20 $\mu$m, 50 $\mu$m, 100 $\mu$m, 200 $\mu$m, 500 $\mu$m, 100 $\mu$m. The pattern of the pores is optionally homogeneous, heterogenous, aligned, repeating, or random.

89. In one aspect, the scaffold can be a "dry scaffold." As used herein, "dry scaffold" refers to any scaffold having no more than 10% water by mass. Put another way, the dry scaffold has less than 10% water by mass. In some instances, the dry scaffold has less than 9, 8, 7, 6, 5, 4, 3, 2, or 1% water by mass. For example, the scaffold can comprise 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10% water by mass.

90. As indicated above, one preferred material for the hydrogel is alginate or modified alginate material. Alginates are versatile polysaccharide based polymers that may be formulated for specific applications by controlling the molecular weight, rate of degradation and method of scaffold formation. Alginate molecules are comprised of (1-4)-linked $\beta$-D-mannuronic acid (M units) and a L-guluronic acid (G units) monomers, which can vary in proportion and sequential distribution along the polymer chain. Alginate polysaccharides are polyelectrolyte systems which have a strong affinity for divalent cations (e.g., $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for the methods described herein. For example, the polymers e.g., alginates, of the hydrogel are 0-100% crosslinked, e.g., at least 1%, 5%, 10%, 20%, 30%, 40%, 50%, 60%, 70%, 80%, 90%, or more, crosslinked. In other embodiments, the polymers, e.g., alginates, of the hydrogel are not crosslinked. In some examples, the polymers, e.g., alginates, of the hydrogel contain less than 50%, e.g., less than 50%, 40%, 30%, 20%, 10%, 50%, 2%, 1%, or less, crosslinking.

91. Alginate may be chemically modified to yield new properties. For example, alginate may be oxidized to increase the rate of biodegradation. Alternatively, alginate may be reduced for improved biocompatibility. Alginate can also be chemically modified to change their crosslinking behavior. For instance, alginate can be modified with bioorthogonal click groups to allow click crosslinking. In another example, alginate can be modified with acrylic groups to allow radical polymerization crosslinking. As another example, alginates can be modified with host-guest chemistries to allow host-guest crosslinking 92. Alginate polymers are formed into a variety of hydro-gel types. Alginate scaffolds can be formed from alginate with molecular weight varying between 1,000 Da to 500,000 Da. Alginate scaffolds can be formed from alginate contain-ing a G/M ratio of between 0.5 and 5. Differences in hydrogel formulation control the kinetics of hydrogel deg-radation. Release rates of pharmaceutical compositions, e.g., small molecules, morphogens, or other bioactive substances, from alginate hydrogels is controlled by hydrogel formula-tion to present the pharmaceutical compositions in a spa-tially and temporally controlled manner. This controlled release eliminates systemic side effects and the need for multiple injections.

93. Useful polysaccharides other than alginates include but are to limited to agarose and microbial polysaccharides such as: Fungal Pullulan, Scleroglucan, Chitin, Chitosan, Elsinan, Bacterial Xanthan gum, Curdlan, Dextran, Gelatin, Levan, Emulsan, Cellulose, Hyaluronic Acid and others.

94. In one aspect, the hydrogel matrixes and/or dry scaffolds ca further comprise receptors (epidermal growth factor receptor (EGFR), platelet derived growth factor receptor (PDGFR)), ligands (including, but not limited to epidermal growth factor (EGF), platelet derived growth factor, granulocyte macrophage colony-stimulating factor (GM-CSF), vascular endothelial growth factor (VEGF), granulocyte colony-stimulating factor (G-CSF), Granulo-cyte macrophage colony-stimulating factor (GM-CSF), macrophage colony-stimulating factor (M-CSF), fibroblast growth factor (FGF), insulin-like growth factor (IGF) 1 (IGF-1), and/or IGF-2), bone morphogenic protein (BMP), ephrin (A1, A2, A3, A4, A5, B1, B2, B3), erythropoetin, fibroblast growth factor (FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, FGF23), Glial cell line-derived neurotrophic factor (GDNF), Hepatocyte growth factor (HGF), Neurotrophins (BDNF, NGF, NT-3, NT-4), T-cell growth factor (TCGF), Transforming growth factor (TGF-α, TGF-β), Tumor necrosis factor-alpha (TNF-α), Wnt Signal-ing Pathway, integrins (including VLA-1, VLA-2, VLA-3, VLA-4, VLA-5, VLA-6, FLJ25220, RLC, PRO827, HsT18964, FLJ39841, HUMINAE, LFA1A, MAC-1, VNRA, MSK8, GPIIb, cadherins (for example, E-cadherin), and/or an immune activating and/or sustaining antibodies, chemokines, and cytokines (such as, for example, IL-2, IL-6, IL-7, IL-15, IL-21, TNF-α, or IFN-γ).

95. It is understood and herein contemplated that the fully activate an immune cell, a co-stimulatory signal may be needed. Thus, in one aspect disclosed herein are hydrogel matrixes and/or dry scaffolds further comprising one or more co-stimulatory molecules which activate a T cell, natural killer (NK) cell, NK T cell, macrophage, tumor infiltrating lymphocyte (TIL), tumor infiltrating NK cell (TINK), or a marrow infiltrating lymphocyte (MIL) includ-ing, but not limited to anti-CD28, B7-1, B7-2, anti-inducible costimulator (ICOS), ICOS ligand, anti-CD27, CD70, 4-1BBL, anti-41-BB, anti-CD40L, CD40, anti-DAP10, anti-CD30, CD30L, anti-TIM-1, anti-TIM-2, anti-TIM-3, anti-CD44, anti-NK1.1, lectin like transcript-1 (LLT-1), anti-CD137, CD48, MICA, anti-2B4, and anti-glucocorticoid-induced tumor necrosis factor receptor related protein (GITR). Thus, the hydrogel matrixes and/or dry scaffolds can also comprises a ligand or antibody that induces signal-ing through a T cell, NK cell, or NK T cell co-stimulatory receptor including, but not limited to anti-CD28, B7-1, B7-2, anti-inducible costimulator (ICOS), ICOS ligand, anti-CD27, CD70, 4-1BBL, anti-41-BB, anti-CD40L, CD40, anti-DAP10, anti-CD30, CD30L, anti-TIM-1, anti-TIM-2, anti-TIM-3, anti-CD44, anti-NK1.1, lectin like tran-script-1 (LLT-1), anti-CD137, CD48, MICA, anti-2B4, and anti-glucocorticoid-induced mor necrosis factor receptor related protein (GITR).

1. Delivery of the Compositions to Cells

96. Transduction of the immune cell can occur by any means known in the art. In one aspect, transduction of the immune cell can occur via a vector encoding a transgene (such as, for example a CAR). Accordingly, in one aspect, are any of the hydrogels and/or dry scaffolds disclosed herein, further comprising a vector (such as, for example, a lentivirus, retrovirus, adenovirus, adeno-associated virus, virus-like-particle, liposome, or transposon) encoding a transgene, such as, for example, a chimeric antigen receptor CAR)).

97. There are a number of compositions and methods which can e used to deliver nucleic acids to cells, either in vitro or in vivo. These methods and compositions can largely be broken down into two classes: viral based delivery systems and non-Viral based delivery systems. For example, the nucleic acids can be delivered through a number of direct delivery systems such as, electroporation, lipofection, cal-cium phosphate precipitation, plasmids, viral vectors, viral nucleic acids, phage nucleic acids, phages, cosmids, virus-like particles (VLPs), transposons (such as, for example, class II transposable elements comprising Sleeping Beauty transposase, Frog Prince, piggyBac, Tol2 a d other Tc1/mariner-type transposases), zinc finger nucleases, mega-nucleases, transcription activator-like effectors (e.g., TAL-ENs), triplexes, mediators of epigenetic modification, and CRISPR and rAAV technologies), minicircle DNA, or via transfer of genetic material in cells or carriers such as virus-like particle, cell-mimicing particles, transposons, exosomes, nanoparticles, micelles or liposomes. Appropri-ate means for transfection, including vectors, chemical transfectants, or physico-mechanical methods such as elec-troporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

(1) Retroviral Vectors

98. A retrovirus is an animal virus belonging to the virus family of Retroviridae, including any types, subfamilies, genus, or tropisms. Retroviral vectors, in general, are described by Verma, I. M., Retroviral vectors for gene transfer. Examples of retroviruses that can be used as vectors include, but are not limited to, human T-lymphotrophic virus (HTLV)-1 (HTLV-1), HTLV-2, HTLV-3, HTLV-4, simian foamy virus, human foamy virus, simian immunodeficiency virus (SIV), human immunodeficiency virus (HIV), and Rous sarcoma virus.

99. A retrovirus is essentially a package which has packed into it a nucleic acid cargo. The nucleic acid cargo carries with it a packaging signal, which ensures that the replicated daughter molecules will be efficiently packaged within the package coat. In addition to the package signal, there are a number of molecules which are needed in cis for the replication, and packaging of the replicated virus. Typically, a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bird the tRNA primer of reverse transcription, terminal repeat sequences that guide the switch f RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

100. Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

101. Lentiviral vectors (LVs), including, but not limited to human immunodeficiency (HIV) vectors and simian immunodeficiency virus (SIV) vectors, are versatile vectors for cell culture or in vivo gene transfer into dividing and nondividing cells. This system has the advantage of being flexible for transducing a range of lung cancer cells, without having to spend time selecting for stable expression. Replication defective VSV G-pseudotyped lentivirus vectors (produced on order by GeneCopoeia) can be used to transduce cells.

(2) Adenoviral Vectors

102. The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994);

Guzman, *Circulation Research* 73:1201-1207 (1993); Bout, *Human Gene Therapy* 5:3-10 (1994); Zabner, Cell 75:207-216 (1993); *Caillaud, Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

103. A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

104. Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19 (such as, for example at AAV integration site 1 (AAVS1)). Vectors which contain this site-specific integration property are preferred. An especially preferred embodiment of this type of vector is the P4.1 C vector produced by Avigen, San Francisco, CA, which can contain the herpes simplex virus thymidine kinase gene, HSV-tk, and/or a marker gene, such as the gene encoding the green fluorescent protein, GFP.

105. In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

106. Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

107. The disclosed vectors thus provide DNA molecules which are capable of integration into a mammalian chromosome without substantial toxicity.

108. The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required or basic interaction of RNA polymerase and transcription factors, and may contain upstream elements and response elements.

(4) Large Payload Viral Vectors

109. Molecular genetic experiments with large human herpesviruses have provided a means whereby large heterologous DNA fragments can be cloned, propagated and established in cells permissive for infection with herpesviruses (Sun et al., *Nature genetics* 8: 33-41, 1994; Cotter and Robertson, *Curr Opin Mol Ther* 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

110. Other useful systems include, for example, replicating an host-restricted non-replicating vaccinia virus vectors.

2. Expression Systems

111. The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

112. Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

113. Enhancer generally refers to a sequence of DNA that functions at no fixed distance from the transcription start site and can be either 5' (Laimins, L et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers f unction to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

114. The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

115. In certain embodiments the promoter and/or enhancer re ion can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

116. It has been shown that all specific regulatory elements ca be cloned and used to construct expression vectors that are selectively expressed in specific cell types such as melanoma cells. The glial fibrillary acetic protein (GFAP) promoter has been used to selectively express genes in cells of glial origin.

117. Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

118. The vectors can include nucleic acid sequence encoding marker product. This marker product is used to determine if the gene has been delivered to the cell and once delivered is being expressed. Preferred marker genes are the *E. Coli* lacZ gene, which encodes β-galactosidase, and green fluorescent protein.

119. In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

120. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P. J. *Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

3. Pharmaceutical Carriers/Delivery of Pharmaceutical Products

121. As described above, the compositions can also be administered in vivo in a pharmaceutically acceptable carrier. By "pharmaceutically acceptable" s meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize an adverse side effects in the subject, as would be well known to one of skill in the art.

122. The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

123. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

124. The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et. al., *Bioconjugate Chem.*, 2:447-451, (1991); Bagshawe, K. D., *Br. J. Cancer,* 60:275-281, 1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathway serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

125. The compositions, including antibodies, can be used therapeutically in combination with a pharmaceutically acceptable carrier.

126. Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

127. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

128. Pharmaceutical compositions may include carriers, thicken rs, diluents, buffers, preservatives, surface active agents and the like in addition to the molecule of choice. Pharmaceutical compositions may also include one or more active ingredients such as antimicrobial agents, antiinflammatory agents, anesthetics, and the like.

129. The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

130. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenisher, electrolyte replenishers (such as those based on Ringer's dextrose), and the like. Preservatives and other additives may also be present such as, for example, antimicrobials, anti-oxidants, chelating agents, and inert gases and the like.

131. Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

132. Compositions for oral administration include powders or granules, suspensions or solutions in water or non-aqueous media, capsules, sachets, or tablets. Thickeners, flavorings, diluents, emulsifiers, dispersing aids or binders may be desirable.

133. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-trialkyl and aryl amines and substituted ethanolamines.

b) Therapeutic Uses

134. Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for give classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 g/kg to up to 100 mg/kg of body weight or ore per day, depending on the factors mentioned above.

C. METHODS OF USING THE COMPOSITIONS

1. Methods of Transducing an Immune Cell and Maki g a Chimeric Antigen Receptor Cell 135. In one aspect, disclosed herein are methods of transducing a cell (such as for example, an immune cell (such as, for example, a T cell, natural killer (NK) cell, NK T cell, macrophage, tumor infiltrating lymphocyte (TIL), tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source), a non-immune cell (such as, for example, a mesenchymal stem cell (MSC), hematopoietic stem cell (HSC), dendritic cell, neural stem cell, induced pluripotent stem cell, or islet cells), including immune and non-immune primary cells and cell lines as well as methods of making a chimeric antigen receptor immune cell, said methods comprising a) obtaining i) a cell (such as for example, an immune cell (such as, for example, a T cell, natural killer (NK) cell, NK T cell, macrophage, tumor infiltrating lymphocyte (TIL), tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source), a non-immune cell (such as, for example, a mesenchymal stem cell (MSC), hematopoietic stem cell (HSC), dendritic cell, neural stem cell, induced pluripotent stem cell, or islet cells), including immune and non-immune primary cells, as well as cell lines and ii) a vector encoding and/or encapsulating an exogenous gene, siRNA, tasiRNA, lncRNA, shRNA, mRNA, gRNA, miRNA, and/or DNA encoding said gene, siRNA, tasiRNA, lncRNA, shRNA, mRNA, gRNA, miRNA (including, but not limited to engineered genes, siRNA, tasiRNA, lncRNA, shRNA, mRNA, gRNA, and/or miRNA, such as, for example, a chimeric antigen receptor (CAR) gene); b) applying the cell and the vector to a scaffold (such as, for example a biocompatible hydrogel matrix and/or dry scaffolds such as, for example, a hydrogel and/or dry scaffold comprising alginate) and, in some aspect, incubating the scaffold, the cell, and the vector. In some aspects, the scaffold further comprises a ligand or antibody for a T cell receptor, or NK cell receptor (including, but not limited to anti-CD3 antibody, CD1d, an Fc fragment of an immunoglobulin, or anti-Fc gamma receptor (FcγRIII) antibody).

136. It is understood and herein contemplated that the transduceed cell can be incubated with the scaffold prior to administration to ensure that the transduced cell is incorporated into the scaffold and is transduced by the vector. In one aspect, the immune cell is incubated with the scaffold for at least 1, 2, 3, 4, 5, 10, 15, 20, 25, 30, 5, 40, 45, 50, 55 minutes, 1, 2, 3, 4, 5, 6, 7, 8, 9, 10, 11, 12, 13, 14, 15, 16, 17, 18, 19, 20, 21, 22, 23, 24, 24, 25, 26, 27, 28, 29, 30, 31, 32, 33, 34, 35, 36, 37, 38, 39, 40, 41, 42, 43, 44, 45, 46, 47, 48, 54, 60, 66, 72, 84, 96 hours 5, 6, 7, 8, 9, 10, 11, 12, 13, or 14 days. In one aspect the cells and scaffold can be administered without incubation.

137. In one aspect, disclosed herein are methods of transducing a cell (such as for example, an immune cell (such as, for example, a T cell, natural killer (NK) cell, NK T cell, macrophage, tumor infiltrating lymphocyte (TIL), tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source, as well as, any commercially available cell or cell line) as well as methods of making a chimeric antigen receptor immune cell disclose herein, wherein the cell is a naïve cell. As noted above, the transduced cell can be a cell from a commercially available cell line. Exemplary cells that can be transduced include, but are not limited to NCI-H295R, 5637, HT-1376, J82, SW 780, T24, T24-Luc-Neo, T24P, BT142, D54-Luc, DBTRG (tumor), DBTRG-05 MG, Gli36-DsRed-R-Luc (rescued), LN-18, LN-229, LN-827(pMMP-LucNeo), M059K, SF-295, SF-539, SF-767, SNB-19, U-251, U-251-Luc-mCh-Puro, U-87 MG, U-87 MG-Luc, Ca Ski, HeLa, KB, C2BBe1, Caco-2, COLO 205, COLO 205-Luc #2, DLD-1, HCC2998, HCT-16, HCT-116-Luc, HCT-15, HC T-8, HT-29, HT-29-Luc, LoVo, LoVo-6-Luc1, LS 174T, LS411N, NCI-H508, SW-480, SW-620, A-431, HEKn, HEL, HEL 92.1.7, HEL 92.1.7-Luc-Neo, HEL-Luc-Neo, TF-1a-Luc-Neo, OE33, A4573, Hs 895.T, NHDF (normal human dermal fibroblasts), TE 353.Sk, TE 354.T, GIST-T1, NCI-N87, NUGC-4, SNU-5, CAL 27, FaDu, L1210, M-NFS-60, HL-60, EOL-1, Kasumi-1, Kasumi-3, Kasumi-3-Luc-mCh-Puro, KG-1-Luc-mCh-Puro, MOLM-13, MV-4-11, MV-4-11-Luc-mCh-Puro, NOMO-1, THP-1, NALM6, NALM6-Luc-MCh-Puro, Reh, Reh (pMMP-Luc-Neo), K-562, K-562-Luc2, ARH-77, CCRF-CEM, DND-41-Luc-mCh-Puro, Jurkat, Jurkat-Clone E6-1, MOLT-4, MOLT-4-Luc-MCh-Puro, Hep 3B2.1-7, Hep G2, LL, LL/2, LL/2-Luc-M38, NCI-H596, Calu-6, NCI-H322M, A549, A549-Luc-C8, Calu-1, Calu-3, HCC827, HCC827-Luc-mCh-Puro, NCI-H125, NCI-H125-Luc, NCI-H1299, NCI-H1650, NCI-H1703, NCI-H1703-Luc-mCh-Puro, NCI-H1975, NCI-H1975-Luc, NCI-H2110, NCI-H2122, NCI-H23, NCI-H292, NCI-H3122, NCI-H441, NCI-H460, NCI-H460-Luc2, NCI-H522, PC-9, DMS 114, NCI-H446, NCI-H69, NCI-H82, SHP-77, EBC-1, SK-MES-1, RL, DB, DB/M2, GRANTA-519, Farange, B-JAB, Daudi, Daudi-Luc-mCh-Puro, NAMALWA, Raji, Raji-Luc, Ramos, Ramos-Luc, HuT78, HT, SU-DHL-6, SU-DHL-6-Luc-mCh-Puro, OCI-Ly1 LN, OCI-Ly19-Luc-Neo, OCI-Ly3-Luc-mCh-Puro, OCI-Ly7-Luc-mCh-Puro (rescued), OCI-Ly7-Luc-Neo, Pfeiffer, SU-DHL-10, SU-DHL-10-LN-High, SU-DHL-16, SU-DHL-4-Luc-mCh-Puro, SU-DHL-8, TMD8, Toledo-Luc-Neo, WSU-DLCL2, WSU-FSCCL, WSU-FSCCL-CMV-Luc-Puro, WSU-FSCCL-MSCV-Luc-Puro-copGFP, NK-2MI, KARPAS 299, BT-20, BT-474, HCC1395, HCC70, Hs 578Bst, Hs 578T, MCF 10A, MCF-7, MCF7-Luc-mCh-Puro, MDA-MB-231, MDA-MB-231-2LMP, MDA-MB-231-Luc-D3H1, MDA-MB-231-Luc-D3H2, MDA-MB-231-Luc-D3H2LN, MDA-MB-231-Luc D3H3, MDA-MB-361, MDA-MB-453, MDA-MB-468, MX-1, MX-1-Luc, SK-BR-3, T47D, UISO-BCA-1, ZR-75-1, A2058, A375, COLO 829, G-361, LOX-IMVI, M14, MDA-MB-435S, OCM-1, OCM-1-Luc-mCh-Puro, PA-NUT, SK-MEL-28, SK-MEL-28-Luc-mCh-Puro, SK-MEL-5, UACC-62, WM-115, WM-266-4, JJN-3-Luc, MM.1S (pMMP-Luc-Neo), NCI-H929, NCI-H929-Luc-mCh-Puro, OPM-2, RPMI 8226, U266B1, SK-N-AS, SK-N-FI, SK-N-SH, MKL-1, A2780, A2780-Luc, IGROV1, IGROV1-Luc-Mch-Puro, OVCAR-4, OVCAR-5, OVCAR-5-Luc-mCh-Puro, OVCAR-8, OVCAR-8-Luc-mCh-Puro, SK-OV-3 (Subcutaneous), SK-OV-3-Luc-D3 (Intraperitoneal), Bx-PC-3, BxPC-3-Luc2, Capan-1, Capan-2, KP4, MIA PaCa-2, MIA PaCa-2-Luc, PANC-1, PANC-1-Luc, SU-86.86, SW 1990, 22Rv1, CWR-22-R, DU 145, DU 145-Luc, LnCap, LnCap clone FGC, PC-3, PC-3-Luc, PC-3M-Luc-C6 (Intracardiac), PC-3M-Luc-C6 (Orthotopic), PC-3M-Luc-C6 (Peritibial), PC-3M-Luc-C6 (SC-Axilla), VCaP, 769-P, 786-O, 786-O-Luc-Neo (rescued), A-498, ACHN, Caki-1, TK-10, A-673, HT-1080, MG-63, Saos-2, SJSA-1, SW 872, MB-1, TT, SK-LMS-1, 293T, HEK293, or HeLa cells. It is also understood and herein contemplated that the transduced cell can be an adherent (e.g., HEK cells) or nonadherent cell (e.g., T cells) or cell line.

138. Other examples of cells that can be transduced in this manner include primary cells of human or animal origin. Examples of such primary cells include, but are not limited to hematopoietic cells, mononuclear cells (peripheral blood mononuclear cells, umbilical cord blood mononuclear cells, macrophage, etc), embryonic cells, primordial germ cells, oocytes, oogonia, ova, spermatocytes, sperm, erythroid precursor cells, lymphoid mother cells, mature blood cells, lymphocytes (including, but not limited to B cells, CD4 T cells CD8 T cells, γδ T cells, NK cells, NK T cells), fibroblasts, neuroblasts, neurocytes, endothelial cells, vascular endothelial cells, hepatocytes, epithelial cells, keratinocytes, pancreatic islet cells, myoblasts, skeletal muscle cells, smooth muscle cells, cancer cells, myeloma cells, and leukemia cells.

139. It is understood and herein contemplated that to fully activate an immune cell, a co-stimulatory signal may be needed. Thus, in one aspect disclosed herein are any of the methods of transducing a cell (such as for example, an immune cell (such as, for example, a T cell, natural killer (NK) cell, NK T cell, macrophage, tumor infiltrating lymphocyte (TIL), tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source) disclosed herein as well as any of the methods of making a chimeric antigen receptor immune cell disclosed herein wherein the scaffold further comprises a ligand or antibody that induces signaling through a T cell, NK cell, or NK T cell co-stimulatory receptor including, but not limited to anti-CD28, B7-1, B7-2, anti-inducible costimulator (ICOS), ICOS ligand, anti-CD27, CD70, 4-1BBL, anti-41-BB, anti-CD40L, CD40, anti-DAP10, anti-CD30, CD30L, anti-TIM-1, anti-TIM-2, anti-TIM-3, anti-CD44, anti-NK1.1, lectin like transcript-1 (LLT-1), anti-CD137, CD48, MICA, anti-2B4, and anti-glucocorticoid-induced tumor necrosis factor receptor related protein (GITR).

140. Also disclosed herein are any of the methods of transducing a cell (such as for example, an immune cell (such as, for example, a T cell, natural killer (NK) cell, NK T cell, macrophage, tumor infiltrating lymphocyte (TIL), tumor infiltrating NK cell (TINK), and/or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source) disclosed herein as well as any of the methods of making a chimeric antigen receptor immune cell disclosed herein, wherein the scaffold further comprises one or more cytokines (such as, for example, IL-2, TNF-α, and/or IFN-γ).

2. Methods of Treating Cancer

141. It is understood and herein contemplated that the disclosed hydrogels and/or dry scaffolds can be used in the treatment, inhibition, reduction, amelioration, and/r prevention of a cancer or metastasis. Thus, disclosed herein are methods of treating, inhibiting, reducing, decreasing, ameliorating, and/or preventing a cancer and/or metastasis in a subject comprising administering to the subject any of the hydrogel matrixes and/or dry scaffolds disclosed herein (including, but not limited scaffolds comprising a ligand or antibody that activates an immune cell receptor and a vector encoding a chimeric antigen receptor to which an immune cell has been applied and is incorporated into the scaffold). Thus, in one aspect, disclosed herein are methods of treating, reducing, inhibiting, ameliorating, decreasing, and/or preventing a cancer and/or metastasis in a subject comprising a) obtaining i) a cell (such as, for example, an immune cell, including, but not limited to a T cell, natural killer (NK) cell, NK T cell, macrophage, tumor infiltrating lymphocyte (TIL), tumor infiltrating NK cell (TINK), or a marrow infiltrating lymphocyte (MIL) including, but not limited to T cell, NK cell, NK T cell, macrophage, TIL, TINK, and/or a MIL obtained from an autologous, allogeneic, and/or haplo-identical donor source) and ii) a vector (such as, for example, a lentivirus, retrovirus, adenovirus, adeno-associated virus, virus-like particle, cell-mimicing particles, transposons, exosomes, nanoparticles, micelles or liposomes) encoding and/or encapsulating an exogenous gene, siRNA, tasiRNA, lncRNA, shRNA, mRNA, gRNA, miRNA, and/or DNA encoding said gene, siRNA, tasiRNA, lncRNA, shRNA, mRNA, gRNA, miRNA (including, but not limited to engineered genes, siRNA, tasiRNA, lncRNA, shRNA, mRNA, gRNA, and/or miRNA, such as, for example, a chimeric antigen receptor (CAR) gene), b) applying the cell and the vector to a scaffold (such as, for example, a biocompatible hydrogel matrix and/or biocompatible dry scaffolds, including, but not limited to scaffolds and hydrogels comprising alginate); c) incubating the immune cells with the hydrogel and/or dry scaffolds; and d) administering the hydrogel and/or dry scaffolds with the immune cells to the subject or administering the immune cells having been incubated with the hydrogel to the subject. In some aspect, the hydrogel and/or dry scaffolds with the immune cells can be administered without incubation prior to the administration. In some aspect the scaffolds can further comprise a ligand or antibody for a cell receptor (such as a T cell receptor, or NK cell receptor (including, but not limited to anti-CD3 antibody, CD1 d, an Fc fragment of an immunoglobin, or anti-Fc gamma receptor (FcγRIII) antibody)) or any protein of interest.

142. It is understood and herein contemplated that the transduced cell can be incubated with the scaffold (including any dry scaffold or hydrogel disclosed herein) prior to administration to ensure that the cell is incorporated into the scaffold and is transduced by the vector. In one aspect, the immune cell is incubated with the scaffold for at least 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24, 24, 25, 26, 27, 28, 29, 30, 31, 32, 33, 34, 35, 36, 37, 38, 39, 40, 41, 42, 43, 44, 45, 46, 47, 48, 54, 60, 66, 72, 84, 96 hours 5, 6, 7, 8, 9, 10, 11, 12, 13, or 14 days. In one aspect the cells and scaffold can be administered without incubation. 143. It is understood and herein contemplated that the fully activate an immune cell, a co-stimulatory signal may be needed. Thus, in one aspect disclosed herein are any of the methods of treating, inhibiting, reducing, decreasing, ameliorating, and/or preventing a cancer or metastasis in a subject, disclosed herein wherein the scaffold further comprises a ligand or antibody that induces signaling through a T cell, NK cell, or NK T cell co-stimulatory receptor including, but not limited to anti-CD28, B7-1, B7-2, anti-inducible costimulator (ICOS), ICOS ligand, anti-CD27, CD70, 4-1BBL, anti-41-BB, anti-CD40L, CD40, anti-DAP10, anti-CD30, CD30L, anti-TIM-1, anti-TIM-2, anti-TIM-3, anti-CD44, anti-NK1.1, lectin like transcript-1 (LLT-1), anti-CD137, CD48, MICA, anti-2B4, and anti-glucocorticoid-induced tumor necrosis factor receptor related protein (GITR).

144. It is understood and herein contemplated that one advantage of the scaffold is the slow release of the transduced cell (i.e., immune or non-immune cell) now transformed with the exogenous gene, siRNA, tasiRNA, lncRNA, shRNA, mRNA, gRNA, miRNA, and/or DNA encoding said siRNA, tasiRNA, lncRNA, shRNA, mRNA, gRNA, miRNA (including, but not limited to engineered genes, siRNA, tasiRNA, lncRNA, shRNA, mRNA, gRNA, and/or miRNA) and activated with a ligand or antibody to a cell receptor, such as, for example, an immune cell receptor) into the tumor microenvironment. Accordingly, in one aspect, disclosed herein are methods of treating, inhibiting, reducing, decreasing, ameliorating, and/or preventing a cancer or metastasis in a subject, wherein the vector in the scaffold (such as a hydrogel matrix and/or dry scaffold) transduces the immune cell and the transduced immune cell in the scaffold can be released into the subject at the site of the cancer following administration of the scaffold over a period of at least 1, 2, 3, 4, 5, 6, 7, 8, 9, 10, 11 12, 13, 14, 15, 16, 17, 18, 19, 20, 21, 22, 23, 24, 24, 25, 26, 27, 2$, 29, 30, 31, 32, 33, 34, 35, 36, 37, 38, 39, 40, 41, 42, 43, 44, 45, 46, 47, 48, 54, 60, 66, 72, $4, 96 hours 5, 6, 7, 8, 9, 10, 11, 12, 13, 14, 15, 16, 17, 18, 19, 20, 21, 22, 23, 24, 24, 25, 26, 27, 28, 29, 30, 31, 32, 45, 58, 59, 60, 61, 62, 90 days, 3, 4, 5, 6, 7, 8, 9, 10, 11, 12, 13, 14, 15, 16, 17, 18, 19, 20, 21, 22, 23, 24, 36 months, 4, 5, 6, 7, 8, 9, 10 years. In one aspect, the immune cell is released from the hydrogel and/or dry scaffold from about 1 week to about 12 weeks after administration of the hydrogel and/or dry scaffold.

145. The disclosed hydrogels and/or dry scaffolds can also comprises additional agents to stimulate endogenous immune responses in a recipient subject with the cancer. Thus, in one aspect, disclosed herein are methods of treating, inhibiting, reducing, decreasing, ameliorating, and/or preventing a cancer or metastasis in a subject, wherein the scaffold further comprises an anti-cancer agent (such as, for example, an immune blockade inhibitor or chemotherapeutic agent).

146. It is understood and herein contemplated that the disclosed hydrogel matrixes and/or dry scaffolds used in the disclosed methods of treating, preventing, inhibiting, and/or reducing a cancer or metastasis can further comprise one or more immune blockade inhibitors and/or chemotherapeutic agents. Chemotherapeutic agents that can be used in the disclosed hydrogel matrixes and/or dry scaffolds can comprise any chemotherapeutic known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara, (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib) Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine 1131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate) JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 31 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (iv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Checkpoint inhibitors include, but are not limited to antibodies that block PD-1 (such as, for example, Nivolumab (BMS-936558 or MDX1106), CT-011, MK-3475), PD-L1 (such as, for example, MDX-1105 (BMS-936559), MPDL3280A, or MSB0010718C), PD-L2 (such as, for example, rHIgM12B7), CTLA-4 (such as, for example, Ipilimumab (MDX-010), Tremelimumab (CP-675,206)), IDO, B7-H3 (such as, for example, MGA271, MGD009, omburtamab), B7-H4, B7-H3, T cell immunoreceptor with Ig and ITIM domains (TIGIT)(such as, for example BMS-986207, OMP-313M32, MK-7684, AB-154, ASP-8374, MTIG7192A, or PVSRIPO), CD96, —and T-lymphocyte attenuator (BTLA), V-domain Ig suppressor of T cell activation (VISTA)(such as, for example, JNJ-61610588, CA-170), TIM3 (such as, for example, TSR-022, MBG453, Sym023, INCAGN2390, LY3321367, BMS-986258, SHR-1702, R07121661), LAG-3 (such as, for example, BMS-986016, LAG525, MK-4280, REGN3767, TSR-033, BI754111, Sym022, FS118, MGDO13, and Immutep) as well as antibodies that block the ligands that innervate PD-1, CTLA-4, LAG-3, TIGIT, CD96, BTLA, B7-H3, VISTA, and TIM-3 including, but not limited to antibodies that block PD-L1, fibrinogen-like protein 1 (FGL1), CD112, CD155, herpes virus entry mediator (HVEM), and Ceacam-1 from binding their respective receptors.

147. The disclosed compositions can be used to treat any disease where uncontrolled cellular proliferation occurs such as cancers. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

D. EXAMPLES

148. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Scaffold-Mediated Static Engineering of T Cells for CAR-T Cell Therapy 149. We have developed a three dimensional (3D) macroporous scaffold as an efficient, single-step, static platform to engineer cells with a vector (for example, T cells with RV vectors). We discovered that 3-dimensional scaffolds with macroporosity and high water absorbing capability can colocalize of viral vectors and T cells similar to what is achieved by using retronectin and spinoculation. We prepared macroporous scaffolds from calcium-crosslinked alginate, which is a GMP-compliant and FDA-approved biomaterial extensively used for many biomedical applications due to its biocompatibility, low toxicity, low cost, and mild gelation by divalent cations. We observed that dry, hygroscopic and macroporous alginate scaffolds facilitate the interaction of vectors and cells (for example, RV vectors and T cells) and enables efficient gene transfer in a single step without spinoculation and without affecting functionality and viability of engineered cells (for example, engineered T cells). Thus, these scaffolds represent a simple, cost effective and tunable platform technology for generating highly functional T cells for adoptive cellular therapy.

150. The macroporous alginate scaffolds were prepared by mild cryogelation (FIG. 1A). Imaging by SEM revealed well connected, 100-200 m pores throughout the scaffold (FIGS. 1B and 1C). Alginate scaffolds were tested for human T cell transduction using RV particles. T cells obtained from peripheral blood of three different healthy donors were activated with agonistic anti-CD3 and anti-CD28 antibodies. Activated T cells were then seeded on either conventional spinoculated RV-retronectin-coated plates or RV particles seeded into the alginate scaffolds. A preliminary screen of transduction efficiency at multiplicities of infection (MOIs) of 1, 2 and 4 (FIG. 3A) using retrovirus encoding GFP demonstrated efficient transduction and an MOI of 2 was chosen for further experiments. As shown in FIG. 1D, 72 hours after incubation with RV particles, T cells expressing GFP on the scaffolds were comparable to those in retronectin coated plates with spinoculation (85±3% vs. 90±5% GFP$^+$ cells). These results showed improved transduction in both groups as compared to viral transduction in the preliminary experiments (FIG. 3A, 49% vs 73.5%, respectively). Despite this, very little variability was noted across three different PBMC donors (FIG. 1D).

151. To evaluate whether the macroporosity of the scaffolds affects the interaction between RV particles and T cells, we fabricated nanoporous scaffolds (FIG. 1E), which can absorb RV particles and T cells, but lack the macroporosity that permits T cell entry into the scaffold. To test whether the sponge-like effect was also needed to create proximity between RV particles and T cells, we tested hydrated macroporous scaffolds, which have the large pores, but lack the active flow of fluid into the internal pores. We found that neither the dry nanoporous scaffold, nor the hydrated macroporous gel allowed efficient gene transfer as compared to dry macroporous scaffold (FIGS. 1F and 1G).

152. Next we assessed whether the CAR-T cells generated using the dry macroporous scaffold were functional in vitro. For these experiments we used RV particles encoding a CAR specific for the CD19 antigen (CD19.CAR). Activated T cells obtained from three healthy donors were seeded on alginate scaffolds or retronectin coated plates loaded with RV particles. Upon removal from the scaffold or retronectin, T cells were maintained in culture, and CAR expression was analyzed on day 3 and day 9 after transduction. As shown in FIG. 2A, both scaffold and retronectin promoted comparable transduction efficiency, and CAR expression remained unaltered upon expansion through day 9 (FIG. 2A, FIG. 3B). CAR-T cells were also analyzed for immune composition by flow cytometry. No differences were observed for expression of CD4, CD8, or memory (CD45RA, CCR7) or exhaustion (PD-1, Lag3) markers (FIGS. 4 and 5). Next to evaluate anti-tumor effects in vitro, control non-transduced T cells (NT-cells) and CD19.CAR-T cells generated either b; scaffold-mediated or retronectin-mediated transduction were co-cultured with CD19 positive target cells (Daudi) and CD19 negative target cells (U937). NT cells did not eliminate either of the tumor cells, while both CD19.CAR-T cells transduced using either the scaffold or retronectin eliminated CD19$^+$ Daudi cells (FIG. 2E and FIG. 6), but not CD19$^-$ U937 cells (FIG. 7). From the same co-culture experiments, cytokines were measured in supernatant collected after 24 h incubation, and CD19.CAR-T cells released IL-2 and interferon IFN-γ in response to Daudi cells (FIGS. 2F, G). Finally, CD19.CAR-T cells generated using both the scaffold and retronectin methods showed comparable proliferative capacity in response to Daudi cells (FIG. 2B). Taken together, these results demonstrate that the alginate scaffold generates highly functional CAR-T cells.

153. The antitumor activity of CAR-T cells observed in vitro results was confirmed in an in vivo tumor model. Daudi cells labeled with firefly luciferase (FfLuc) were intravenously (i.v.) injected in nonobese diabetic severe combined immunodeficiency/γc−/− (NSG) mice, and four days mice were infused i.v. with either control non-transduced (NT) cells or CD19.CAR-T cells generated by either scaffold- or retronectin-mediated transduction. CD19.CAR-T cells generated by either method controlled tumor cell growth as assessed by the measurement of tumor bioluminescence intensity (FIG. 8B, 8C, and FIG. 9). Control of the tumor was associated with an improved overall survival rate (FIG. 8E) and without significant toxicity as assessed by changes in body weight (FIG. 8D). Thus, scaffold generated CAR-T cells were equally functional in vivo as CAR-T cells generated by the conventional retronectin/spinoculation approach.

154. In conclusion, we demonstrate that a biocompatible, macroporous alginate scaffold is as effective in generating T cells engineered with retrovirus as the commercially available retronectin owing to its macroporosity and hygroscopic nature. The dry scaffold we have developed eliminates the need for spinoculation of plates coated with retronectin and seeded with the retroviral particles, thereby simplifying the manufacturing process. CAR-T cells generated through static transduction on the macroporous alginate gel fully maintained their functionality. These data support the potential for the use of an easily synthesizable and low cost transduction platform to enable generation of highly functional T cells for adoptive cell therapy. This simple platform is also likely to address the need for efficient transduction methods useful with other refractory cell types.

a) Materials and Methods (1) Preparation of Macroporous Alginate Scaffold

155. Macroporous alginate scaffold was prepared. A 2% solution ultrapure alginate (PRONOVA®, MVG) in water was vigorously stirred with 4% calcium gluconate for 15 mins. The resulting mixture (final calcium concentration 0.01M) was then cast in 24 well plates (1 mL/well), frozen at −20° C. overnight, and lyophilized. The scaffold was either used immediately or stored at 4° C. before use in in vitro or in vivo experiments.

(2) Preparation of Dry Nanoporous Alginate Scaffold

156. Calcium crosslinked alginate gel was cast in 24 well plat s and allowed to gel overnight. The gels were then subjected to multistep solvent exchange with increasing concentrations of ethanol (10, 30, 50, 70, 90, and 100% v/v), followed by drying with supercritical $CO_2$.

(3) Scanning Electron Microscopy:

157. Dry macroporous scaffold was cut with a sharp razor, coated with 70 nm AuPd (Au: 60%, Pd: 40%) for 10 minutes at 7 nm/min and analyzed on Hitachi S-3200N Variable pressure SEM. The surface morphology of the nanoporous scaffolds was analyzed by field emission scanning electron microscopy, FESEM (Verios FE1)

(4) Cell Lines and Retronectin-Mediated CAR-T Cell Generation.

158. Daudi cells expressing firefly luciferase were maintained in RPMI 1640 (Gibco) supplemented with 10% fetal bovine serum (Gibco), 2 mmol/L GLUTAMAX™ (Gibco), penicillin (100 units/mL) and streptomycin (100 mg/mL; Gibco). All cells were maintained at 37° C. with 5% C02. T cells expressing CAR were generated in accordance with standard operating procedures currently used to manufacture CAR-T cells for clinical use at UNC-CH. Peripheral blood mononuclear cells were isolated from buffy coats (Gulf Coast Regional Blood Center) using LYMPHOPREP™ medium (Accurate Chemical and Scientific Corporation) and activated on plates coated with 1 mg/mL CD3 (Miltenyi Biotec) and CD28 (BD Biosciences) monoclonal antibodies. GFP encoded or CD19.CAR encoded retro virus was prepared according to method reported previously. The viral titer was measured by standard flow cytometry assay. Serially diluted viral stock were added to HEK293T cells. 72 hours later, GFP expression was analyzed by flow cytometry. Population with 5-20% GFP+ cells were used to calculate the viral titer (transducing units/mL) using the following equation: Titer (TU/mL)=(initial cell count*% GFP+)/(volume of virus*dilution factor). MOI was calculated as the ratio of the number of transducing viral particles used to the actual number of cells. Activated T cells were transduced with GFP encoded or CD19 CAR encoded retroviral supernatants on retronectin-coated 24-well plates (Takara Bio Inc.) Two days after activation, transduced T cells were expanded in 50% Click's Medium (Irvine Scientific) and 50% RPMI-1640 supplemented with 10% HyClone fetal bovine serum (GE Healthcare), 2 mmol/L GLUTAMAX™ (Gibco). penicillin (100 units/mL), and streptomycin (100 mg/mL; Gibco) with 10 ng/mL IL7 and 5 ng/mL of IL15 (PeproTech) for 10 to 14 days before being used for functional assays (5) Scaffold-Mediated Generation of CAR-T Cells.

159. Retroviral supernatant containing GFP-encoded or human CD19.CAR-encoded gamma retrovirus was concentrated 20-fold by AMICON® centrifugation (MWCO 100 Kda, Milipore) at 4° C., 2500 g, 15-20 mins. Dry alginate scaffolds were transferred to non-tissue culture coated 24 well plates (Falcon). Concentrated retrovirus (2 mL of viral supernatant concentrated to 200 μL) and $1 \times 10^6$ human PBMCs (isolated from Buffy coats) in a total volume of 300 μl media were pipetted onto each scaffold. Control scaffolds were seeded with $1 \times 10^6$ PBMCs suspended in cell culture medium. The seeded scaffolds were incubated without any additional medium in a 5% C02 incubator at 37° C. for 1 h, after which 1 ml of complete medium was added. After 3 days of culture, cells were isolated from scaffolds by digesting with 0.125 M EDTA and analyzed for GFP expression or CD19.CAR expression by flow cytometry.

(6) Flow Cytometry and Antibodies

160. Monoclonal antibodies specific for human CD3 (APC-Cy7, 557832), CD4 (APC-Cy7, 561839), CD8 (PerCP-Cy5.5, 565310), CD20, CD45RA (PE, 555489), CD62L (BV421, 563861), LAG3 (PE, 565617), PD-1 (FITC, 561035), and TIM3 (BV421, 565563) were purchased from BD Biosciences, and CCR7 (FITC, FAB197F-100) from R&D Systems. An anti idiotype scFv monoclonal antibody was used to detect the expression of the CD19.CAR. All samples were analyzed using a BD LSRII, and a minimum of 10,000 events were acquired per sample. Results were analyzed using FLOWJO™ 9 (FlowJo LLC).

(7) Cytokine Production by CAR-T Cells.

161. CAR-T cells were cocultured with Daudi tumor cells at 1:5 effector to target [E:T] ratio for 24 hours and the culture supernatant was collected. IL-2 and IFN-gamma were quantified by ELISA using the manufacturer's protocol (R&D Systems).

(8) In Vitro Cytotoxicity.

162. Tumor cells (Daudi) were seeded at $1 \times 10^5$ cells per well in 24-well plates. CAR-T cells normalized for transduction efficiency were added at 1:5 E T ratio. On day 5 of coculture, cells were collected, and the frequency of T cells and residual tumor (CD20+) cells were measured by flow cytometry.

(9) In Vivo Antitumor Activity.

163. Eight-to-ten weeks old female, non-obese, diabetic, severe combined immunodeficiency/γc−/− (NSG) mice were infused with $1 \times 10^6$ ffLuc-expressing Daudi cells intravenously. Four days after infusion, each mouse was intravenously injected with either $4 \times 10^6$ CD19.CAR-T cells or non-transduced (NT) cells. Tumor burden was monitored using the Xenogen-IVIS™ Imaging System. Mice were monitored for signs of discomfort and euthanized upon losing more than 15% of initial body weight or the development of hind-limb paresis. All procedures involving animals were done in compliance with University's Institutional Animal Care and Use Committee.

(10) Statistical Analysis.

164. All statistical analysis was done using two-tailed Student's t-test, one way ANOVA or two-way ANOVA with Tukey post hoc analysis using graph pad prism and noted in figures as $*=p<0.05$, $=p<0.01$, $*p<0.001$.

2. Example 2: Multifunctional Biomaterial Scaffolds Fast Tracks CAR-T Cell Therapy 165. CAR T cell therapy has demonstrated unprecedented success against CD19-expressing B cell malignancies, resulting in two FDA approvals and inspiring hundreds of ongoing clinical trials. Despite the revolutionary potential of CAR-T cell therapies to treat human malignancies, the complex procedures and expense required to produce clinical grade CAR-T cells is a major obstacle to widespread clinical use. Therapeutic CAR-T cell manufacturing requires an extensive array of steps, including: (i) T cell collection via leukapheresis from the patient and shipment to the manufacturing center; (ii) labor-intensive procedures under good manufacturing practice (GMP) conditions to activate, expand and engineer the T cells using vectors; (iii) quality control of the produced cells; and (iv) shipment of the final CAR-T cell product to the hospital and re-infusion into the patient. The complete manufacturing process can cost up to half a million dollars and can take several weeks. This delay is problematic because the aggressiveness of many cancers may not allow sufficient time to complete the production. In addition, extensive ex vivo culture is linked to T cell differentiation, which impairs the potency of CAR-T cells by compromising their engraftment and persistence in vivo.

166. Faster methods to generate CAR-T cells with high therapeutic potential are sorely needed. Closed and automatic manufacturing devices have been implemented to reduce the labor needed to manufacture CAR-T cells ex vivo, but this approach still requires significant ex vivo cell manipulation. Allogeneic off-the-shelf CAR-T cells could overcome the need for CAR-T cell manufacturing for each individual patient, but may cause life-threatening graft-versus-host disease or may be rapidly eliminated by the host's immune system. Finally, systemic delivery of CAR constructs to T cells in vivo using nanoparticles or lentivirus have been proposed. However, this approach is limited by the short plasma half-life of systemically infused virus and nonspecific targeting of nanoparticles. Due to these limitations, in situ generation of CAR-T cells with minimal ex vivo manipulation remains highly attractive. Such an approach eliminate the need for extensive ex vivo culture, prevent the terminal differentiation of CAR-T cells prior to administration, and facilitate use of autologous T cells as compared to allogeneic CAR-T cell products.

167. Herein is described an all-in-one Macroporous Alginate Scaffold for T cell Engineering and Release (MASTER also referred to herein as CCI-A1g) that provides for in vivo CAR-T cell generation with minimal extracorporeal manipulation. MASTER can be directly loaded with patient-derived T cells and viral particles encoding the CAR and implanted on the same day to generate CAR-T cells in vivo (FIG. 22). MASTER is designed to: (i) host T cells and viral particles; (ii) stimulate T cell activation and proliferation, iii) promote T cell transduction and (iv) sustainably release fully functional CAR-T cells into the circulation to control tumor growth.

168. Alginate was selected as the basis for these multifunctional scaffolds (MASTER also referred to herein as CCI-A1g) due to its biocompatibility, biodegradability, mild gelation requirements and extensive application as a 3D structure for cell culture. To promote T cell activation within the scaffold cyclooctyne-conjugated anti-CD3 and anti-CD28 antibodies were immobilized on azide-modified alginate through Vild and efficient copper-free click chemistry (FIG. 10). To activate and expand T cells within the scaffold, the cytokine IL2 was physically entrapped in the scaffold. Finally, macroporosity of the alginate scaffold was achieved using mild cryogelation (FIG. 11A). Configuring the large pores throughout the scaffold is critical initially to provide an interface for efficient contact between the cells and retrovirus and subsequently for mass transfer of nutrients to the proliferating CAR-T cells. As shown in FIG. 11B, SEM images of MASTER revealed well connected, 100-200 m pores throughout the scaffold. Cell distribution within the scaffold was assessed by seeding T cells expressing GFP on AF-647 labeled MASTER. 3D confocal microscopy showed that T cells (~12 m diameter) were homogeneously distributed throughout the pores of the scaffold (FIG. 11C, FIG. 12).

169. Efficient T cells activation and transduction is crucial for CAR-T cell manufacturing. To ensure that T cells loaded in MASTER receive the appropriate activation cues necessary for retroviral-mediated gene transfer, escalating doses of agonistic anti-CD3 and anti-CD28 antibodies (0, 0.5, 1, 2, or 4 μg at 1:1 w/w per mg alginate) conjugated to MASTER were tested. Human peripheral blood mononuclear cells (PBMCs) from three different donors were seeded in MASTER and analyzed after 18 hours for the expression of the early T-cell activation marker CD69. As shown in FIG. 11D, cells seeded on MASTER demonstrated a ~10-fold increase in CD69 expression as compared to cells seeded on alginate scaffolds without antibodies. Highest CD69 expression was achieved at an antibody concentration of 1 μg/mg alginate, and this density was used for further studies. To test MASTER-mediated simultaneous activation and transduction of non-activated T cells, naive PBMCs and GFP-encoding retrovirus were added to MASTER (FIG. 11E) and to scaffold controls lacking antibodies and the resulting CAR-T cell populations compared to those produced using conventional spinoculation (centrifugation onto retronectin-coated plates).

After 72 hours of incubation, GFP expression was barely detected when non-activated PBMCs and virus were incubated on blank scaffold or spinoculated (<0.4%). In contrast, incubation of non-activated PBMCs on MASTER resulted in 20% transduction of the T cells (FIGS. 11F and 11G), indicating that MASTER functions as a platform for both T-cell activation and static transduction via retroviral gene transfer.

170. Next, the functionality of CAR-T cells generated within MASTER were assessed using retrovirus encoding a CD19-specific CAR (CD19.CAR). PBMCs and CD19.CAR gamma retroviral particles were loaded on MASTER and incubated for 3 or 10 days. As shown in FIG. 13A, CAR expression was detected in 22%±1% T cells at day 3 and remained stable at day 10 (FIG. 14). Since T cell phenotype is an important determinant for successful engraftment and persistence of CAR-T cells, MASTER-generated CAR-T cells were analyzed for phenotypic composition and compared to CAR-T cells generated using conventional clinical procedures (spinoculation of activated T cells and retrovirus on retronectin-coated plates) Both sets of CAR-T cells contained similar amounts of CD4$^+$ and CD8$^+$ T cells (FIG. 13B). However, MASTER-generated CAR-T cells contained a higher percentage of CCR7$^+$CD45RA$^+$ central memory T cells (14.8% vs 2.57%), CCR7$^+$CD45RA$^+$ stem cell-like T cells (21.5% vs 9.8%) and CCR7$^+$CD2L$^+$ T cells with lymphoid homing capacity (13.1% vs 2.98%) than conventionally generated CAR-T cells (FIG. 13C, FIG. 15). Characterization for expression of exhaustion markers, PD-1 and LAG3 on day 12 post-transduction showed less than 1% of CAR-T cells generated by either method were PD-1$^+$ LAG3$^+$ (FIG. 13D). In addition, all three cell types (non-transduced, MASTER, and conventionally produced CAR-T cells) showed comparable proliferative capacity in response to CD19$^+$ tumor cells (FIG. 13E).

171. To evaluate anti-tumor effects in vitro, control non-transduced T cells (NT-cells) and CD19.CAR-T cells generated either by MASTER or by spinoculation were co-cultured with CD19$^+$ target cells (Daudi) and CD19$^-$ target cells (U937) at 1:5 effector-to-target ratio (E:T). While NT-cells did not eliminate either of the tumor cells, both MASTER and spinoculation-generated CD19.CAR-T cells eliminated CD19$^+$ cells, but not CD19 cells (FIG. 13F, FIG. 16). In these co-culture experiments, CD19.CAR-T cells released IL-2 and interferon IFN-γ in response to CD19$^+$ cells (FIGS. 13G and 13H). Taken together, these results demonstrate that MASTER generates highly functional CAR-T cells with improved differentiation phenotypes in comparison to conventionally produced CAR-T cells.

172. We next evaluated whether MASTER releases resident T cells. MASTER with or without encapsulated IL2 were seeded with PBMCs ($1\times10^6$) and placed into transwell inserts (pore size 40 µm). At defined time points, each scaffold was transferred to a new well and the cells released into the bottom chamber were counted. MASTER efficiently released cells over five days (FIG. 17) likely owing to inherent migratory properties of activated T cells and the well connected macroporous structure of the scaffold.

173. Motivated by the above results demonstrating MASTER functions as an all-in-one platform for T-cell activation, transduction, expansion, and release, the antitumor activity of MASTER-produced CAR-T cells was tested in an in vivo xenograft tumor model. MASTER was seeded with PBMCs and CD19.CAR-encoding retroviral particles, incubated for one hour, and subcutaneously implanted in NSG mice engrafted with Ffluc-labeled Daudi cells. Tumor-bearing mice treated with conventionally generated CAR-T cells infused i.v. served as positive controls (FIG. 18A). Mice subcutaneously implanted with MASTER seeded with only PBMCs or infused i.v. with non-transduced cells serve as negative controls. Tumors grew rapidly in mice treated with control non-transduced cells, while MASTER-produced CAR-T cells and conventional i.v. infused CAR-T ells equally controlled tumor progression up to day 45, without significant changes in body weight (FIGS. 18B-18D, FIG. 19). At 100 days, i.v infusion of 4 million conventionally produced CAR-T cells led to 16.6% tumor-free survival. In contrast, implantation of MASTER with 2 million PBMCs increased tumor-free survival to 50% (p=0.15, FIG. 18E). The in vivo persistence of CAR-T cells was also examined. Mice were bled on day 14 and 22. On day 32, when control mice reached the humane endpoint, 3 mice from each of CAR-T treated group were euthanized, and blood, bone marrow (BM) and spleen were collect d. Cell suspensions were analyzed for human CD45$^+$CD3$^+$CAR$^+$ cells (FIG. 20). Remarkably, MASTER-generated CAR-T cells had nearly 30-fold higher absolute counts in the peripheral blood at 22 days (FIG. 18F) and significantly increased counts in the bone marrow and spleen at 32 days compared to conventional CAR-T cells infused i.v. (FIG. 18G & H, FIG. 21). Since bone marrow is the primary site for lymphoma in this tumor model, CAR$^+$ cells isolated from bone marrow were further analyzed for the expression of exhaustion markers PD-1 and LAG3. CAR-T cells generated and released from MASTER had significantly lower expression of PD-1 and LAG-3 as compared to CAR-T cells expanded ex vivo and infused i.v. Taken together, these results demonstrate that CAR-T cells produced using MASTER were equally functional as conventional CAR-T cells in controlling tumor growth, but had better expansion and persistence, as well as being produced with drastically reduced time, complexity, and cost.

174. In summary, we generated a multifunctional scaffold that brings together the key aspects of CAR-T cell manufacturing and delivery under one platform, reducing the entire process to just one day. The scaffold includes anchored anti-CD3 and anti-CD28 antibodies and IL2, which guarantee adequate T cell activation and proliferation, while the macroporosity facilitates homogeneous distribution of T cells, creates an interface for interaction between viral particles and T cells, and assists the in vivo release of fully functional reprogrammed CAR-T cells. The MASTER system is a major improvement on previous biomaterials because it is not limited to local release of exogenously seeded CAR-T cells, instead MASTER provides in situ reprogramming and release of highly functional CAR-T cells. Furthermore, MASTER is a modular platform technology that can be adapted to reprogram other immune cells or to deliver immunomodulatory factors to support cell function synergistically.

a) Experimental Section (1) DBCO-Modification of Antibodies

175. A 10-fold molar excess of NHS-PEG4-DBCO (A134-10, Click Chemistry Tools, USA) was added to anti-CD3 or anti-CD28 antibodies (FIG. 11) and incubated at room temperature for 1 h. Then the solution was purified by AMICON® centrifugation (MWCO 10 kDa) at 4° C., 10000 g, 10 mins until the flow through was free from NHS-PEG4-DBCO (measured by characteristic absorbance of DBCO moiety at 309 nm using NANODROP™) The degree of DBCO incorporation (i.e. the number of DBCO per antibody) was determined from the absorbance scan of the purified conjugate (235-400 nm) using the following equation.

$$\text{(Molarity of DBCO)/(Molarity of antibody)} = (A\_309DBCO \times \varepsilon\_280Ab)/(\varepsilon\_309DBCO \times A\_280c Ab)$$

A309 DBCO=DBCO-Ab conjugate's absorbance at 309 nm

ε280 Ab=210,000M-1 cm−1

A280C Ab=conjugate's corrected absorbance at 280 nm=A280−(A309×CF DBCO) ε309 DBCO=12000M-1 cm−1

A280Ab=DBCO-Ab conjugate's absorbance at 280 nm

CF DBCO=DBCO correction factor at 280 nm=1.089

(2) Preparation of CCI-A1g (MASTER)

176. Azide modified alginate was prepared. To prepare MASTER, a 2% (w/v) solution of azido alginate in molecular biology grade water was incubated with DBCO-modified CD3 and CD28 antibody (1 µg/mg alginate) at 4° C. overnight. Recombinant human IL2, at a concentration of 0.2 ug/mg alginate was next added and the solution was stirred for 15 mins. Finally, the resulting solution was vigorously stirred with equal volume of 4% calcium gluconate for 15 mins, casted in 24 well plates (1 mL/well), frozen at −20° C. overnight and lyophilized. MASTER was either used immediately or stored at 4° C. and used within a week for in vitro or in vivo experiments.

(3) Scanning Electron Microscopy (SE M):

177. Dry macroporous scaffold was cut with a sharp razor blade, coated with 70 nm AuPd (Au: 60%, Pd: 40%) for 10 minutes at 7 nm/min and analyzed on Hitachi S-3200N variable pressure SEM.

(4) Confocal Microscopy:

178. AF647 DBCO (click chemistry tools) was click conjugated to alginate modified with anti-CD3 and anti-CD28 antibody. Excess unbound dye as removed by dialysis against water for 1 day. AF647-labeled scaffolds were fabricate as described above. $1\times10^6$ GFP+ T cells were seeded on these scaffolds, incubated overnight at 37° C. and imaged using Zeiss LSM 880 confocal microscope.

(5) Cell Lines and CAR-T Cell Generation

179. Firefly Luciferase expressing Daudi cells was maintained in RPMI 1640 (Gibco) supplemented with supplemented with 10% FBS (Gibco), 2 mmol/L GLUTAMAX™ (Gibco) and penicillin (100 units/mL) and streptomycin (100 mg/mL; Gibco). All cells were maintained at 37° C. with 5% $CO_2$.

(6) Conventional CAR-T Cell Generation

180. Peripheral blood mononuclear cells were isolated from buffy coats (Gulf Coast Regional Blood Center) using LYMPHOPREP™ medium (Accurate Chemical and Scientific Corporation) and activated on plates coated with 1 mg/mL CD3 (Miltenyi Biotec) and CD28 (BD Biosciences) mAbs. Activated T cells were transduced with retroviral supernatants on retronectin-coated 24-well plates (Takara Bio Inc.) 2 days after activation. Transduced T cells were expanded in 50% Click's Medium (Irvine Scientific) and 50% RPMI-1640 supplemented with 10% HyClone FBS (GE Healthcare), 2 mmol/L GLUTAMAX™ (Gibco) and penicillin (100 units/mL) and streptomycin (100 mg/mL; Gibco) with 10 ng/mL IL7 and 5 ng/mL of IL15 (PeproTech) for 10 to 14 days of culture before being used for functional assays (7) Scaffold Mediated Generation of CAR-T Cells 181. 293T medium containing GFP encoded or human CD19.CAR encoded gamma retrovirus (RV) was concentrated 10-fold by AMICON® centrifugation (MWCO 100 Kda, Milipore) at $4°$ C., 2500 g, 15-20 mins. Dry lyophilized MASTER scaffolds were transferred to non-tissue culture coated 24 well plates (Falcon), and 200 µL of concentrated RV and $1×10^6$ PBMCs isolated from Buffy coats (total volume of virus and PBMC=300 µl) was pipetted onto each scaffold. Control scaffolds were seeded with $1×10^6$ BMCs suspended in cell culture medium. For in vitro studies only, the seeded scaffolds were incubated without any additional medium in the 5% $CO_2$ incubator at $37°$ C. for 1 h, then 1 ml of complete medium was added. Cells were isolated from scaffolds after 96 h by digesting with 0.125 M EDTA, washed twice with excess PBS and analyzed for GFP expression or CD19.CAR expression by flow cytometry. For in vivo studies, MASTER was seeded with PBMCs and CD19.CAR encoding retrovirus, incubated for ~1 h at $37°$ C. until the media was completely absorbed by the scaffolds and implanted on the same day in the subcutaneous space of NSG mice.

(8) Flow Cytometry and Antibodies

182. Monoclonal antibodies specific for human CD3 (APC-Cy7, 557832), CD4 (APC-Cy7, 561839), CD8 (PerCP-Cy5.5, 565310), CD20 (FITC, 555622), CD45RA (PE, 555489), CD62L (BV421, 563861), LAG3 (PE, 565617), PD-1 (FITC, 561035), and TIM3 (BV421, 565563) were purchased from BD Biosciences, and CCR7 (FITC, FAB197F-100) from R&D Systems. An anti-idiotype scFv monoclonal antibody was used to detect the expression of the CD19.CAR. All samples were acquired on a BD LSRII, and a minimum of 10,000 events were acquired per sample. Samples were analyzed on FLOWJO™ 9 (FlowJo LLC).

(9) Cytokine Production by CAR-T Cells

183. CAR-T cells were cocultured with Daudi tumor cells at 1:5 effector to target [E:T] ratio for 24 hours and the culture supernatant was collected. IL-2 and IFN-gamma was quantified by ELISA as per manufacturer's protocol (R&D Systems).

(10) In Vitro Cytotoxicity

184. Tumor cells (Daudi) were seeded at $1×10^5$ cells per well in 24-well plates. CAR-T cells normalized for transduction efficiency were added at 1:5 E:T ratio. On day 5 of coculture, cells were collected, and the frequency of T cells and residua tumors (CD20+) cells was measured by flow cytometry.

(11) In Vitro T Cell Release Assay:

185. Scaffolds were seeded with $1×10^6$ PBMCs and placed on 40 µm cell mesh (Corning). The mesh was used as a transwell insert and placed in 6 well plate. The bottom of the well contained complete T cell medium. At definite time points, cells in the bottom chamber were counted and the scaffold with the insert was moved to a new well containing fresh media.

(12) In Vivo Antitumor Activity

186. Ten to twelve week-old, female, immune-compromised SG mice (NOD.Cg-Prkdc$^{scid}$ Il2rg$^{tm1Wjl}$/SzJ) were infused with $1×10^6$ FFluc expressing Daudi cells intravenously. Four days after infusion, each mouse (n=9) was implanted with two MASTER in the subcutaneous space. Each scaffold was loaded with $1×10^6$ PBMCs (isolated from human buffy coats, two different donors) and CD19.CAR encoded gamma retrovirus and subcutaneously implanted on the same day. Mice intravenously injected with either $4×10^6$ non-transduced (NT) T cells or implanted with MASTER seeded with $1×10^6$ PBMCs only (no retrovirus) were used as negative control. Mice infused with $4×10^6$ D19 CAR T cells generated by conventional method as described above were used as positive control. Tumor burden was monitored using the Xenogen-IVIS™ Imaging System. Mice were monitored for signs of discomfort and euthanized upon losing more than 15% of initial body weight, the development of hind-limb paresis, or reaching humane endpoint based on tumor burden. All procedures involving animals were done in compliance with University's Institutional Animal Care and Use Committee.

187. To analyze CAR+cells in blood, bone marrow or spleen, single cell suspensions from these organs were stained with anti-human CD45, anti-human CD3, and CAR.19 antibody and analyzed by flow cytometry. Single-cell suspensions of spleen were obtained by mincing the organ through a 70 m cell mesh. Red blood cells were lysed by resuspending splenocytes in ACK lysis buffer (Lonza). Bone marrow single-cell suspensions were obtained by flushing the bones with a syringe containing PBS. The cell suspension was passed through a 70 µm cell mesh and red blood cells were lysed by resuspending cells in lysis buffer (BD PHARM LYSE™). Similarly, blood collected via cheer bleed was incubated with lysis buffer (BD PHARM LYSE™), washed with PBS and passed through 70 m cell mesh before staining with antibodies. Failure to cheek bleed on day 22 resulted in exclusion of one mice treated with MASTER scaffolds.

3. Example 3: Physical Features of MASTER

188. To get a better understanding of the physical features of MASTER, took transverse and cross-sectional CT images of MASTER (FIGS. 23A and 23B). Cross-sectional and transverse section images areas of higher density (scaffolds) as indicated by brighter values and darker areas which reveal areas of air porosity. Using the CTscan to isolate the pores and color code pores based on size, we were able to calculate porosity to be 75.8%.

Next we calculated the relative frequency of various pore dimensions (FIG. 23C). Nearly 60% of the pores had a mean diameter of 101-200 µm. The next largest group of pores were <100 µm in diameter (approximately 25%). As shown in FIG. 23D, as determined by the aspect ratio of the pores, most pores had an oblong shape. Next, we calculated the total surface area inside of MASTER (FIG. 23E). By taking surface area as a function of the volume plotted, the inside surface area of MASTER was shown to be approximately 810 mm. Looking at the connectivity of the pores, we were able to display the node of the pore as a sphere with lines moving between pores. The more connections a pores had, the larger the spherical representation (FIG. 23F). Calculating the number of connections, approximately 50% of the pores had less than 3 connections, around 28% had 4-6 connections, and 10% had 7-9 connections (FIG. 23G). A very few pores (around 6%) have more connections than 9.

a) Methods

189. The X-ray computed tomography (CT) scans were performed in a XRADIA VERSA 510 with the acquisition parameters seen in the table below.

TABLE 1

| Image acquisition parameters from the X-ray CT experiments. | |
| --- | --- |
| Scanning parameters | |
| Projections | 1600 |
| Filter | None |
| Voltage | 40 kV |
| Current | 74 µA |
| Pixel size | 2.6 µm |
| Exposure | 8 seconds |
| Optical magnification | 4× |

A cylindrical volume of 2.50×2 mm was scanned in each sample. These volumes were used to calculate the porosity of the samples and the dimensions of the pores. A smaller sub-volume of 10×1 mm was extracted to calculate and show connectivity between the cells. This was done to reduce the size of calculation and enhance the visualization of the results.

190. The CT data was analyzed using the software Dragonfly [Dragonfly 2020.1 [Computer software]. Object Research Systems (ORS) Inc, Montreal, Canada, 2018. To segment the samples a training dataset was created manually for each sample using histogram thresholding and masking techniques. Once the training data was create it was used to train a deep learning image segmentation model called U-net. The resulting model was then used to segment the full samples into scaffolds and porosity. To calculate the connectivity between the pores an open-source package called openPNM was used.

4. Example 4: MASTER has Improved Tumor Control Over i.v. Infusion Of CAR T Cells in a Tumor Rechallenge Model 191. To see the effect that MASTER exhibits on tumor control, we compared MASTER to i.v., infusion of CAR T cells using a lymphoma xenograft rechallenge model. NSG mice were engrafted with FFLuc- labeled CD19+ human Daudi tumor cells. At 4 days post graft mice were implanted with MASTER or received i.v. infusion of CAR T cells; and at 29 days post engraftment, mice were rechallenged (FIG. 24A). FIG. 24B shows in vivo tumor bioluminescence imaging (BLI) of NSG mice treated with MASTER, conventional CAR-T cells or control non-transduced (NT) cells. We then plotted individual tumor growth curves of mice treated with NT cells (FIG. 24C), MASTER (FIG. 24D) or i.v. infused with CAR T cells (FIG. 24E). Each line represents one animal. Lastly we plotted the survival of each group over time (FIG. 24F). By day 30 post engraftment 100% of the NT mice had died (ie., non survived long enough to be subject to rechallenge). By contrast, all mice receiving either MASTER or i.v., infusion of CAR T cells survived to rechallenge. However, following rechallenge, the difference in the efficacy of the two groups became evident. By day 60 (30 days post rechallenge), only 50% of the i.v. infusion group survived and less than 20% survived by day 80. The precipitous drop in survival of the mice receiving CAR T cells i.v., infusion, is in stark contrast to the MASTER group which continued to show 100% survival out to at least 80 days post engraftment (50 days post rechallenge).

5. Example 5: Biocompatibility of Master

192. We also wanted to investigate the biocompatibility of MASTER and its components in various tissues (liver, heart, kidney, lung, spleen, and skin). Tissue samples were taken and H&E-stained four weeks after subcutaneous implant of MASTER, MASTER+mouse PBMCs+GFP encoded gamma retrovirus and untreated controls in C57B16/J immunocompetent mice (FIG. 25). We further analyzed the mouse blood (FIG. 26). No differences were observed between any of the treatment groups showing compete biocompatibility.

6. Example 6: MASTER Loaded with PBMCs and Retrovirus does not Transduce Surrounding Host Cells 193. We next observed whether MASTER loaded with PBMCs and retrovirus transduces host cells (FIG. 27). Using an in vitro transwell model mimicking the in vivo system, GFP expression in fibroblast cells seeded on the bottom of transwell plate showed that virus doesn't leak out of scaffold when MASTER is co-seeded with PBMCs and virus (MOI 2). Put simply, MASTER loaded with PBMCs and retrovirus does not transduce host cells.

7. Example 7 Lentiviral Transduction of Adherent Cells

194. To investigate the ability of lentiviral transduction on adherent cells, dry scaffold was seeded with 1 million HEK293T cells and GFP encoding lentivirus (MOI 2) (FIG. 28). Cells were isolated from scaffold after 72 h and GFP expression was measured. 41.3% of the HEK293T cells expressed GFP.

E. REFERENCES

Agarwal S, Weidner T, Thalheimer F B, Buchholz C J. In vivo generated human CAR T cells eradicate tumor cells. Oncoimmunology. 2019; 8: e1671761.

Andersen T, Auk-Emblem P, Dornish M. 3D Cell Culture in Alginate Hydrogels. Microarrays (Basel). 2015; 4: 133-161.

Andreadis S T, Palsson B O. Kinetics of retrovirus mediated gene transfer: the importance of intracellular half-life of retroviruses. J Theor Biol. 1996; 182: 1-20.

Baldino L, Concilio S, Cardea S, Reverchon E. Interpenetration of Natural Polymer Aerogels by Supercritical Drying. Polymers. 2016; 8. doi:10.3390/polym8040106

Brudno Y, Desai R M, Kwee B J, Joshi N S, Aizenberg M, Mooney DJ. In vivo targeting through click chemistry. ChemMedChem. 2015; 10: 617-620.

Cheung A S, Zhang D K Y, Koshy S T, Mooney D J. Scaffolds that mimic antigen-presenting cells enable ex vivo expansion of primary T cells. Nat Biotechnol. 2018; 36: 160-169.

Chuck A S, Palsson BØ. Membrane adsorption characteristics determine the kinetics of flow-through transductions. Biotechnol Bioeng. 1996; 51: 260-270.

Diaconu I, Ballard B, Zhang M, Chen Y, West J, Dotti G, et al. Inducible Caspase-9 Selectively Modulates the Toxicities of CD19-Specific Chimeric Antigen Receptor-Modified T Cells. Mol Ther. 2017; 25: 580-592.

Fesnak A D, June C H, Levine B L. Engineered T cells: the promise and challenges of cancer immunotherapy. Nat Rev Cancer. 2016; 16: 566-581.

García A J, Vega M D, Boettiger D. Modulation of cell proliferation and differentiation through substrate-dependent changes in fibronectin conformation. Mol Biol Cell. 1999; 10: 785-798.

Grupp S A, Kalos M, Barrett D, Aplenc R, Porter D L, Rheingold S R, et al. Chimeric Antigen Receptor-Modified T Cells for Acute Lymphoid Leukemia. N Engl J Med. 2013; 368: 1509-1518.

Hanenberg H, Xiao X L, Dilloo D, Hashino K, Kato I, Williams D A. Colocalization of retrovirus and target cells on specific fibronectin fragments increases genetic transduction of mammalian cells. Nat Med. 1996; 2: 876-882.

Havenga M, Hoogerbrugge P, Valerio D, van Es H H. Retroviral stem cell gene therapy. Stem Cells. 1997; 15: 162-179.

Hollyman D, Stefanski J, Przybylowski M, Bartido S, Borquez-Ojeda O, Taylor C, et al. Manufacturing validation of biologically functional T cells targeted to CD19 antigen for autologous adoptive cell therapy. J Immunother. 2009; 32: 169-180.

Hwang C M, Sant S, Masaeli M, Kachouie N N, Zamanian B, Lee S-H, et al. Fabrication of three-dimensional porous cell-laden hydrogel for tissue engineering. Biofabrication. 2010; 2: 035003.

Jackson H J, Rafiq S, Brentjens R J. Driving CAR T-cells forward. Nat Rev Clin Oncol. 2016; 13: 370-383.

Jena B, Maiti S, Huls H, Singh H, Lee D A, Champlin R E, et al. Chimeric antigen receptor (CAR)-specific monoclonal antibody to detect CD19-specific T cells in clinical trials. PLoS One. 2013; 8: e57838.

June C H, Riddell S R, Schumacher T N. Adoptive cellular therapy: a race to the finish line. Sci Transl Med. 2015; 7: 280ps7.

Korin Y D, Zack J A. Progression to the G1b phase of the cell cycle is required for completion of human immunodeficiency virus type 1 reverse transcription in T cells. J Virol. 1998; 72: 3161-3168.

Lamers C H J, van Elzakker P, van Steenbergen S C L, Sleijfer S, Debets, Gratama J W. Retronectin-assisted retroviral transduction of primary human T lymphocytes under good manufacturing practice conditions: tissue culture bag critically determines cell yield. Cytotherapy. 2008; 10: 406-416.

Lamers C H J, Willemsen R A, Luider B A, Debets R, Bolhuis R L H. Protocol for gene transduction and expansion of human T lymphocytes for clinical immunogene therapy of cancer. Cancer Gene Ther. 2002; 9: 613-623.

Lan M A, Gersbach C A, Michael K E, Keselowsky B G, Garcia A J. Myoblast proliferation and differentiation on fibronectin-coated self assembled monolayers presenting different surface chemistries. Biomaterials. 2005. pp. 4523-4531. doi:10.1016/j.biomaterials.2004.11.028

Lee D W, Kochenderfer J N, Stetler-Stevenson M, Cui Y K, Delbrook C, Feldman S A, et al. T cells expressing CD19 chimeric antigen receptors for acute lymphoblastic leukaemia in children and young adults: a phase 1 dose-escalation trial. Lancet. 2015; 385: 517-528.

Lee K Y, Mooney D J. Alginate: properties and biomedical applications. Prog Polym Sci. 2012; 37: 106-126.

Leyfman Y. Chimeric antigen receptors: unleashing a new age of anti-cancer therapy. Cancer Cell Int. 2018; 18: 182.

Lichtman E I, Dotti G. Chimeric antigen receptor T-cells for B-cell malignancies. Transl Res. 2017; 187: 59-82.

Lin P, Correa D, Lin Y, Caplan A I. Polybrene inhibits human mesenchymal stem cell proliferation during lentiviral transduction. PLoS One. 2011; 6: e23891.

Ma Q, Safar M, Holmes E, Wang Y, Boynton A L, Junghans R P. Anti-prostate specific membrane antigen designer T cells for prostate cancer therapy. Prostate. 2004; 61: 12-25.

Maiti S N, Huls H, Singh H, Dawson M, Figliola M, Olivares S, et al. Sleeping beauty system to redirect T-cell specificity for human applications. J Immunother. 201; 36: 112-123.

Maude S L, Frey N, Shaw P A, Aplenc R, Barrett D M, Bunin N J, et al. Chimeric antigen receptor T cells for sustained remissions in leukemia. N Engl J Med. 2014; 371: 1507-1517.

Maus M V, June C H. Making Better Chimeric Antigen Receptors for Adoptive T-cell Therapy. Clin Cancer Res. 2016; 22: 1875-1884.

Morgan R A, Boyerinas B. Genetic Modification of T Cells. Biomedicin s. 2016; 4. doi:10.3390/biomedicines4020009

Nakazawa Y, Huye L E, Dotti G, Foster A E, Vera J F, Manuri P R, et al. Optimization of the PiggyBac transposon system for the sustained genetic modification of human T lymphocytes. J Immunother. 2009; 32: 826-836.

Nakazawa Y, Saha S, Galvan D L, Huye L, Rollins L, Rooney C M, et al. Evaluation of long-term transgene expression in piggyBac-modified human T lymphocytes. J Immunother. 2013; 36: 3-10.

Neelapu S S, Locke F L, Bartlett N L, Lekakis L, Miklos D, Jacobson C A, et al. Kte-C19 (anti-CD19 CAR T Cells) Induces Complete Remissions in Patients with Refractory Diffuse Large B-Cell Lymphoma (DLBCL): Results from the Pivotal Phase 2 Zuma-1. Blood. 2016. p. LBA-6. doi:10.1182/blood.v128.22.1ba-6.1ba-6

Newick K, O'Brien S, Moon E, Albelda S M. CAR T Cell Therapy for Solid Tumors. Annu Rev Med. 2017; 68: 139-152.

Parker L L, Do M T, Westwood J A, Wunderlich J R, Dudley M E, Rosenberg S A, et al. Expansion and characterization of T cells transduced with a chimeric receptor against ovarian cancer. Hum Gene Ther. 2000; 11: 2377-2387.

Patel S, Jones R B, Nixon D F, Bollard C M. T-cell therapies for HIV: Preclinical successes and current clinical strategies. Cytotherapy. 2016; 18: 931-942.

Pettitt D, Arshad Z, Smith J, Stanic T, Hollsnder G, Brindley D. CAR-T Cells: A Systematic Review and Mixed Methods Analysis of the Clinical Trial Landscape. Mol Ther. 2018; 26: 342-353.

Plumridge H. New costly cancer treatments face hurdles getting to patients. Wall St J. 2014; 6.

Pollok K E, Hanenberg H, Noblitt T W, Schroeder W L, Kato I, Emanuel, et al. High-efficiency gene transfer into normal and adenosine deaminase-deficient lymphocytes is mediated by transduction on recombinant fibronectin fragments. J Virol. 1998; 72: 4882-4892.

Prasad V. Immunotherapy: Tisagenlecleucel—the first approved CAR-T-cell therapy: implications for payers and policy makers. Nat Rev Clin Oncol. 2018; 15: 11-12.

Prasad V. Tisagenlecleucel—the first approved CAR-T-cell therapy: implications for payers and policy makers. Nature Reviews Clinical Oncology. 2018. pp. 11-12 doi: 10.1038/nrclinonc.2017.156

Qin Y. Gel swelling properties of alginate fibers. J Appl Polym Sci. 2004; 91: 1641-1645.

Quintas-Cardama A, Yeh R K, Hollyman D, Stefanski J, Taylor C, Nikhamin Y, et al. Multifactorial optimization of gammaretroviral gene transfer into human T lymphocytes for clinical application. Hum Gene Ther. 2007; 18: 1253-1260.

Ramanayake S, Bilmon I, Bishop D, Dubosq M-C, Blyth E, Clancy L, et al. Low-cost generation of Good Manufacturing Practice-grade CD19-specific chimeric antigen receptor-expressing T cells using piggyBac gene transfer and patient-derived materials. Cytotherapy. 2015. pp. 1251-1267. doi:10.1016/j.jcyt.2015.05.013

Ramos C A, Ballard B, Zhang H, Dakhova O, Gee A P, Mei Z, et al. Clinical and immunological responses after CD30-specific chimeric antigen receptor—redirected lymphocytes. J Clin Invest. 2017; 127: 3462-3471.

Ramos C A, Savoldo B, Dotti G. CD19-CAR trials. Cancer J. 2014; 20: 112-118.

Robinet E, Certoux J M, Ferrand C, Maples P, Hardwick A, Cahn J Y, et al. A closed culture system for the ex vivo transduction and expansion of human T lymphocytes. J Hematother. 1998; 7: 205-215.

Rosenberg S A, Restifo N P. Adoptive cell transfer as personalized immunotherapy for human cancer. Science. 2015; 348: 62-68.

Salter A I, Pont M J, Riddell S R. Chimeric antigen receptor—modified T cells: CD19 and the road beyond. Blood. 2018; 131: 2621-2629.

Savoldo B, Dotti G. Chimeric antigen receptors (CARs) from bench-to-bedside. Immunol Lett. 2013; 155: 40-42.

Savoldo B, Ramos C A, Liu E, Mims M P, Keating M J, Carrum G, et al. CD28 costimulation improves expansion and persistence of chimeric antigen receptor-modified T cells in lymphoma patients. J Clin Invest. 2011; 121: 1822-1826.

Seo S, Smith C, Fraser C, Patheja R, Shah S P, Rehan S, et al. Adoptive T-cell therapy for pediatric cytomegalovirus-associated retinitis. Blood Adv. 2019; 3: 1774-1777.

Shapiro L, Cohen S. Novel alginate sponges for cell culture and transplantation. Biomaterials. 1997; 18: 583-590.

Sharma P, King G T, Shinde S S, Purev E, Jimeno A. Axicabtagene ciloleucel for the treatment of relapsed/refractory B-cell non-Hodgkin's lymphomas. Drug s Today. 2018; 54: 187-198.

Smith T T, Stephan S B, Moffett H F, McKnight L E, Ji W, Reiman D, et al. In situ programming of leukaemia-specific T cells using synthetic DNA nanocarriers. Nat Nanotechnol. 2017; 12: 813-820.

Tonks A, Tonks A J, Pearn L, Mohamad Z, Burnett A K, Darley R L. Optimized retroviral transduction protocol which preserves the primitive subpopulation of h man hematopoietic cells. Biotechnol Prog. 2005; 21: 953-958.

Turtle C J, Hanafi L-A, Berger C, Gooley T A, Cherian S, Hudecek M, et al. CD19 CAR-T cells of defined CD4+: CD8+ composition in adult B cell ALL patients. Clin Invest. 2016; 126: 2123-2138.

Verhoeyen E, Costa C, Cosset F-L. Lentiviral Vector Gene Transfer into Human T Cells. Genetic Modification of Hematopoietic Stem Cells. 2009. pp. 97-114. doi: 10.1007/978-1-59745-409-4_8

Watanabe K, Kuramitsu S, Posey A D Jr, June C H. Expanding the Therapeutic Window for CAR T Cell Therapy in Solid Tumors: The Knowns and Unknowns of AR T Cell Biology. Front Immunol. 2018; 9: 2486.

Xu Y, Zhang M, Ramos C A, Durett A, Liu E, Dakhova O, et al. Closely related T-memory stem cells correlate with in vivo expansion of CAR.CD19-T cells and are preserved by IL-7 and IL-15. Blood. 2014; 123: 3750-3759.

Zhao Y, Moon E, Carpenito C, Paulos C M, Liu X, Brennan A L, et al. Multiple injections of electroporated autologous T cells expressing a chimeric antigen receptor mediate regression of human disseminated tumor. Cancer Res. 2010; 70: 9053-9061.

Zhou P, Lee J, Moore P, Brasky K M. High-Efficiency Gene Transfer into Rhesus Macaque Primary T Lymphocytes by Combining 32° C. Centrifugation and CH-296-Coated Plates: Effect of Gene Transfer Protocol on T Cell Homing Receptor Expression. Human Gene Therapy. 2001. pp. 1843-1855. doi:10.1089/104303401753153901

Bach, P. B. National Coverage Analysis of CAR-T Therapies—Policy, Evidence, and Payment. *New England Journal of Medicine vol.* 379 1396-1398 (2018).

Caffrey, M. With approval of CAR T-cell therapy comes the next challenge: payer coverage. *Am. J. Manag. Care* 24, SP35-SP36 (2018).

Coon, M. E., Stephan, S. B., Gupta, V., Kealey, C. P. & Stephan, M T. Nitinol thin films functionalized with CAR-T cells for the treatment of solid tumours. *Nat Biomed Eng* 4, 195-206 (2020).

Depil, S., Duchateau, P., Grupp, S. A., Mufti, G. & Poirot, L. 'Off-the-shelf' allogeneic CAR T cells: development and challenges. *Nat. Rev. Drug Discov.* 1-15 (2020).

Enblad, G. et al. A phase I/IIa trial using CD19-targeted third-generation CAR T cells for lymphoma and leukemia. *Clin. Cancer Res.* 24, 6185-6194 (2018).

Gattinoni, L., Klebanoff, C. A. & Restifo, N. P. Paths to sternness: building the ultimate antitumour T cell. *Nat. Rev. Cancer* 12, 671-684 (2012).

Ghassemi, S. et al. Reducing Ex Vivo Culture Improves the Antileukemic Activity of Chimeric Antigen Receptor (CAR) T Cells. *Cancer Immunol Res* 6, 1100-1109 (2018).

Hernandez, I. Analysis determines true cost for CAR T-cell therapy. *Helio-In the Journals Plus*. Accessed December 3, (2018).

Hori, Y., Winans, A. M. & Irvine, D. J. Modular injectable matric-s based on alginate solution/microsphere mixtures that gel in situ and co-deliver immunomodulatory factors. *Acta Biomater.* 5, 969-982 (2009).

Maude, S. L. et al. Tisagenlecleucel in Children and Young Adults with B-Cell Lymphoblastic Leukemia. *N. Engl. J. Med.* 378, 439-448 (2018).

Mock, U. et al. Automated manufacturing of chimeric antigen receptor T cells for adoptive immunotherapy using CliniMACS prodigy. *Cytotherapy* 18, 1002-1011 (2016).

Park, J. H. et al. Long-Term Follow-up of CD19 CAR Therapy in Acute Lymphoblastic Leukemia. *N. Engl. J. Med.* 378, 449-459 (2018).

Pettitt, D. et al. CAR-T Cells: A Systematic Review and Mixed Methods Analysis of the Clinical Trial Landscape. *Mol. Ther.* 26, 342-353 (2018).

Plumridge, H. New costly cancer treatments face hurdles getting to patients. *Wall St. J.* 6, (2014).

Ramos, C. A. et al. Clinical responses with T lymphocytes targeting malignancy-associated κ light chains. *J. Clin. Invest.* 126, 2588-2596 (2016).

Rosenblum, D., Joshi, N., Tao, W., Karp, J. M. & Peer, D. Progress and challenges towards targeted delivery of cancer therapeutics. *Nat. Commun.* 9, 1410 (2018).

Savina, I. N., Ingavle, G. C., Cundy, A. B. & Mikhalovsky, S. V. A simple method for the production of large volume 3D macroporous hydrogels for advanced biotechnological, medical and enviromnental applications. *Sci. Rep.* 6, 21154 (2016).

Shah, N. N. & Fry, T. J. Mechanisms of resistance to CAR T cell therapy. *Nat. Rev. Clin. Oncol.* 16, 372-385 (2019).

Simmons, A. & Alberola-Ila, J. Retroviral Transduction of T Cells a d T Cell Precursors. *Methods Mol. Biol.* 1323, 99-108 (2016).

Smith, T. T. et al. Biopolymers codelivering engineered T cells and STING agonists can eliminate heterogeneous tumors. *J. Clin. Invest.* 127, 2176-2191 (2017).

Stock, S. et al. Influence of Retronectin-Mediated T-Cell Activation on Expansion and Phenotype of CD19-Specific Chimeric Antigen Receptor T Cells. *Hum. Gene Ther.* 29, 1167-1182 (2018).

Tang, J., Hubbard-Lucey, V. M., Pearce, L., O'Donnell-Tormey, J. & Shalabi, A. The global landscape of cancer cell therapy. *Nat. Rev. Drug Discov.* 17, 465-466 (2018).

Vera, J. et al. T lymphocytes redirected against the kappa light chain of human immunoglobulin efficiently kill mature B lymphocyte-derived malignant cells. *Blood* 108, 3890-3897 (2006).

Xu, Y. & Dotti, G. Selection bias: maintaining less-differentiated cells for adoptive immunotherapy. *The Journal of clinical investigation vol.* 126 35-37 (2016).

What is claimed is:

1. A method of transducing an immune cell, the method comprising a) obtaining a non-transduced immune cell and a viral vector encoding an exogenous gene, siRNA, tasiRNA, lncRNA, shRNA, mRNA, gRNA, or miRNA, and b) applying the non-transduced immune cell and the viral vector to a dry macroporous scaffold comprising pores sized to permit substantially homogenous distribution of immune cells throughout the scaffold, wherein application of the non-transduced immune cell and the viral vector to the dry macroporous scaffold results in conversion of the non-transduced immune cell to a transduced immune cell.

2. The method of transducing the immune cell of claim 1, further comprising incubating the scaffold and the cell for at least 1 hour.

3. The method of transducing the immune cell of claim 1, wherein the scaffold further comprises a ligand or antibody for an immune cell receptor.

4. The method of claim 3, wherein the ligand or antibody is an anti-CD3 antibody.

5. The method of transducing the immune cell of claim 1, wherein the viral vector encodes the exogenous gene, wherein the exogenous gene encodes a chimeric antigen receptor.

6. A method of making a chimeric antigen receptor (CAR) immune cell, the method comprising a) obtaining an immune cell that lacks a chimeric antigen receptor, b) applying the immune cell to a dry, macroporous scaffold comprising pores sized to permit substantially homogenous distribution of immune cells throughout the scaffold; wherein the scaffold comprises i) a ligand or antibody for a T cell receptor or NK cell receptor and ii) a viral vector encoding a chimeric antigen receptor, wherein application of the immune cell to the dry, macroporous scaffold results in conversion of the immune cell that lacks the chimeric antigen receptor to the chimeric antigen receptor immune cell.

7. The method of claim 1, wherein the method does not comprise use of a recombinant fibronectin fragment.

8. The method of claim 1, wherein the immune cell is a T cell or a natural killer cell.

9. The method of claim 1, wherein the immune cell is a peripheral blood mononuclear cell (PBMC).

10. The method of claim 1, wherein the immune cell is transduced in the presence of IL-2.

11. The method of claim 1, wherein 60% of the pores in the macroporous scaffold have a mean diameter of between 100 and 200 microns.

12. A method of treating cancer or metastasis in a subject comprising a)transducing the immune cell using the method of claim 1; and b) administering the scaffold with the immune cell to the subject.

13. The method of making the CAR immune cell of claim 6, wherein the scaffold further comprises a cytokine, and wherein the cytokine comprises IL-2, IL-15, IL-7, IL-23, TNF-α, or IFN-γ.

14. The method of making the CAR immune cell of claim 6, wherein the ligand or antibody comprises anti-CD3, anti-CD28, CD1d, an Fc fragment of an immunoglobulin, or anti-Fc gamma receptor (FcγRIII).

15. The method of making the CAR immune cell of claim 6, wherein the immune cell is a naïve immune cell, and wherein the scaffold further comprises a ligand or antibody that induces signaling through a T cell, NK cell, or NK T cell co-stimulatory receptor.

16. The method of claim 13, wherein the method does not comprise use of a recombinant fibronectin fragment.

17. The method of claim 13, wherein the immune cell is a T cell or a natural killer cell.

18. The method of claim 13, wherein the immune cell is a peripheral blood mononuclear cell (PBMC).

19. The method of claim 13, wherein the ligand or antibody is an anti-CD3 antibody.

20. The method of claim 13, wherein the immune cell is transduced in the presence of IL-2.

21. The method of claim 13, wherein 60% of the pores in the macroporous scaffold have a mean diameter of between 100 and 200 microns.

22. A method of treating a cancer or metastasis in a subject comprising a) making the CAR immune cell via the method of claim 6; and b) administering the scaffold with the immune cell to the subject.

* * * * *